US011945841B2

(12) United States Patent
Wang et al.

(10) Patent No.: US 11,945,841 B2
(45) Date of Patent: Apr. 2, 2024

(54) HEADLESS HEMAGGLUTIN INFLUENZA VACCINE

(71) Applicant: Georgia State University Research Foundation, Inc., Atlanta, GA (US)

(72) Inventors: Baozhong Wang, Duluth, GA (US); Lei Deng, Atlanta, GA (US)

(73) Assignee: Gerogia State University Research Foundation, Inc., Atlanta, GA (US)

( * ) Notice: Subject to any disclaimer, the term of this patent is extended or adjusted under 35 U.S.C. 154(b) by 397 days.

(21) Appl. No.: 16/649,905

(22) PCT Filed: Oct. 4, 2018

(86) PCT No.: PCT/US2018/054335
§ 371 (c)(1),
(2) Date: Mar. 23, 2020

(87) PCT Pub. No.: WO2019/070955
PCT Pub. Date: Apr. 11, 2019

(65) Prior Publication Data
US 2020/0247852 A1 Aug. 6, 2020

Related U.S. Application Data

(60) Provisional application No. 62/567,936, filed on Oct. 4, 2017.

(51) Int. Cl.
C07K 14/005 (2006.01)
A61K 9/51 (2006.01)
A61K 39/145 (2006.01)
C12N 7/00 (2006.01)

(52) U.S. Cl.
CPC .............. C07K 14/005 (2013.01); A61K 9/51 (2013.01); A61K 39/145 (2013.01); C12N 7/00 (2013.01); C07K 2319/02 (2013.01); C12N 2760/16122 (2013.01); C12N 2760/16123 (2013.01); C12N 2760/16134 (2013.01);
(Continued)

(58) Field of Classification Search
None
See application file for complete search history.

(56) References Cited

U.S. PATENT DOCUMENTS

2015/0273048 A1 10/2015 Kang et al.
2016/0361411 A1 12/2016 Gindy et al.

FOREIGN PATENT DOCUMENTS

WO    2010117786 A1    10/2010
WO    2013116656 A1    8/2013
(Continued)

OTHER PUBLICATIONS

Complete Search Report issued by the European Patent Office for application 18864814.1, dated Sep. 20, 2021.
(Continued)

Primary Examiner — Michelle S Horning
(74) Attorney, Agent, or Firm — Thomas | Horstemeyer, LLP

(57) ABSTRACT

Disclosed are universal influenza based on a truncated influenza hemagglutin (HA) protein lacking a head domain (hrHA). Also disclosed is a composition comprising a nanoparticle coated with a disclosed hrHA polypeptide. Also disclosed is a composition comprising a virus like particle (VLP) expressing on its surface a disclosed hrHA polypeptide.

12 Claims, 44 Drawing Sheets
Specification includes a Sequence Listing.

(52) U.S. Cl.
CPC ............ *C12N 2760/16222* (2013.01); *C12N 2760/16223* (2013.01); *C12N 2760/16234* (2013.01)

(56) References Cited

FOREIGN PATENT DOCUMENTS

| WO | 2014070848 A1 | 5/2014 |
| WO | 2014191435 A1 | 12/2014 |

OTHER PUBLICATIONS

Deng et al., Protein Nanoparticle Vaccine Based on Flagellin Carrier Fused to Influenza Conserved Epitopes Confers Full Protection Against Influenza A Virus Challenge, Virol., vol. 509, p. 82-89, 2017.

Wang et al., Coated Protein Nanoclusters From Influenza H7N9 HA are Highly Immunogenic and Induce Robust Protective Immunity, Nanomedicine: NBM, vol. 13, p. 253-262, 2017.

Wang et al., Double-Layered M2e-NA Protein Nanoparticle Immunization Induces Broad Cross-Protection against Different Influenza Viruses in Mice, Advanced Healthcare Materials, vol. 9, No. 2, p. 1901176, 2019.

Yassine et al., Hemagglutinin-stem nanoparticles generate heterosubtpic influenza protection, Nature Medicine, vol. 21, No. 9, 1065-1070, 2015.

Deng et al., Double-layered protein nanoparticles induce broad protection against divergent influenza A viruses, Nature Communications, vol. 9, No. 1, 2018.

Wang et al., Nanoclusters self-assembled from confromation-stabilized influenza M2e as broadly cross-protective influenza vaccines, Nanomedicine, Nanotechnology, Biology and Medicine, vol. 10, No. 2, 473-482, 2014.

Partial Search Report issued by the European Patent Office for application 18864814.1, dated Apr. 14, 2021.

International Search Report issued for PCT/US2018/054335, dated Feb. 27, 2019.

Steel et al., Influenza virus vaccine based on the conserved hemagglutinin stalk domain, MBio., vol. 1, No. 1, 2010.

UniProtKB Accession No. HEMA_I68A0 "Pre-mRNA-splicing factor 38A", https://www.uniprot.org/uniprot/P03437, 1986.

Chen et al., Fusion protein linkers: property, design and functionality, Advanced drug delivery reviews, vol. 65, No. 10, p. 1357-1369, 2013.

4M2e-GCN4 amino acids sequence:

MSLLTEVETPIRNEWGSRSNDSSDPGGSSGGSSLLTEVETPTRSEWESRSSD
SSDPGGSSGGSSLLTEVETPTRNGWESKSSGSSDPGGSSGGSSLLTEVETPT
RNGWESNSSDSSDPGGGGSSSSLELKQIEDKLEEILSKLYHIENELARIKKLLGE

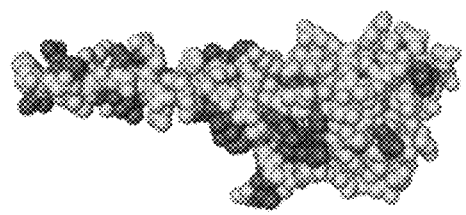
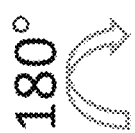
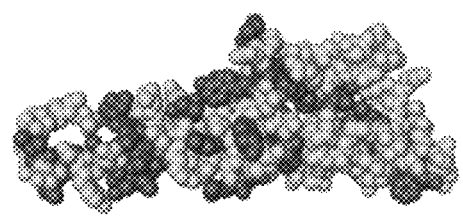
hrH3
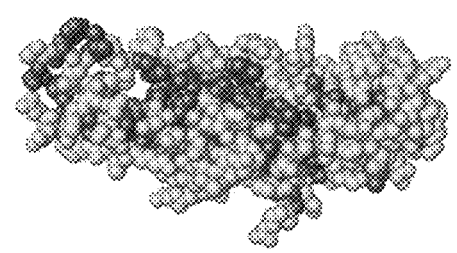
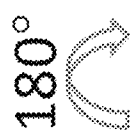
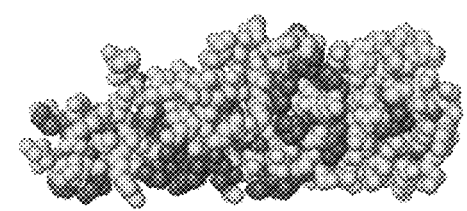
hrH1
FIG. 4B

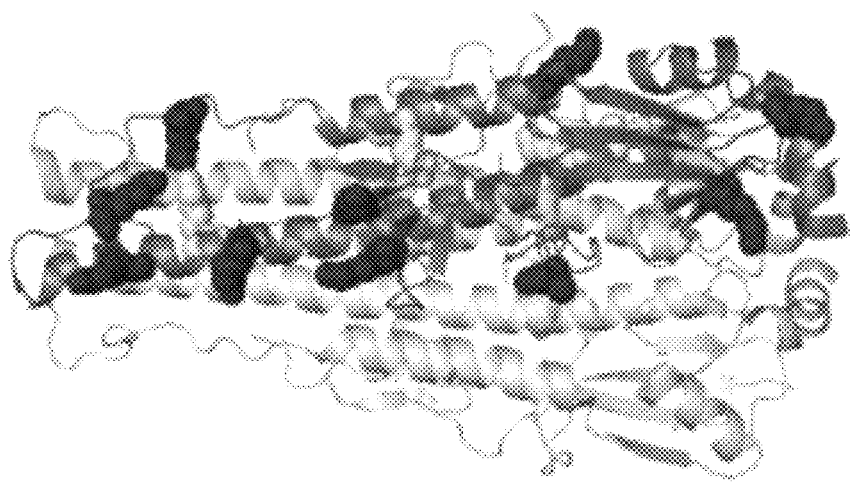
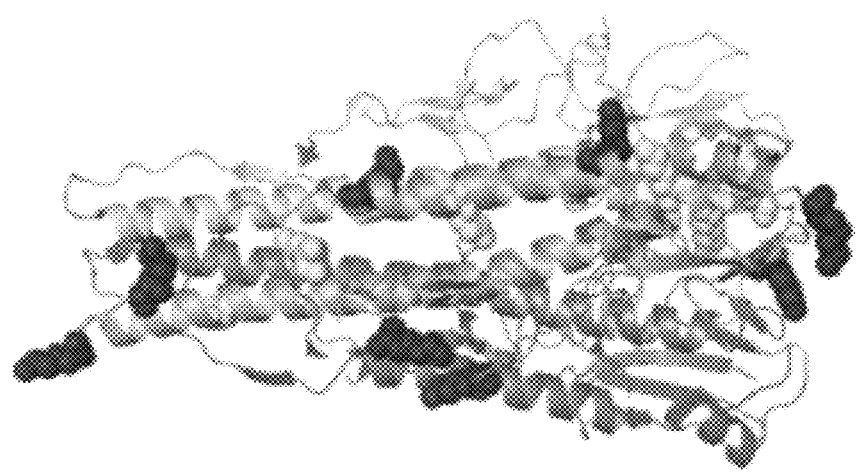
FIG. 4C

Uni4C1
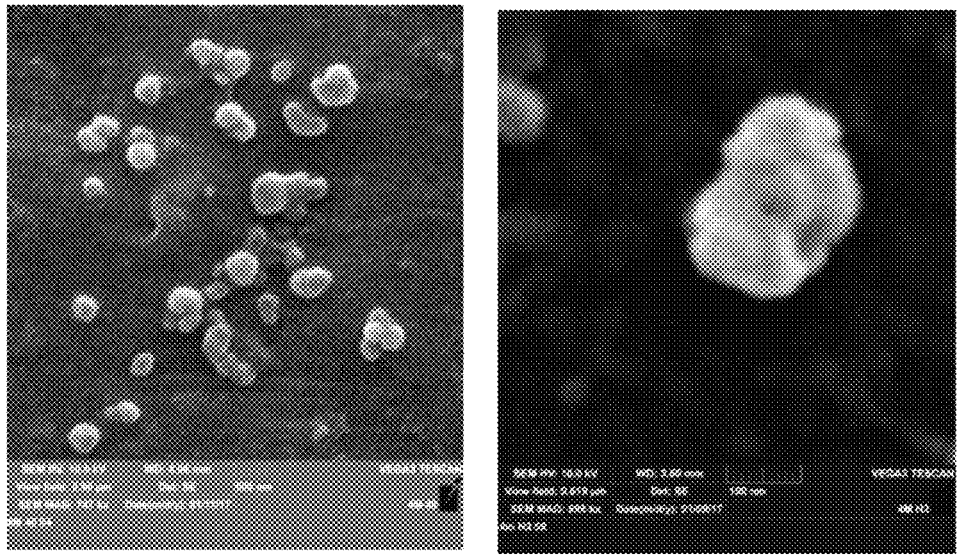
Uni4C3
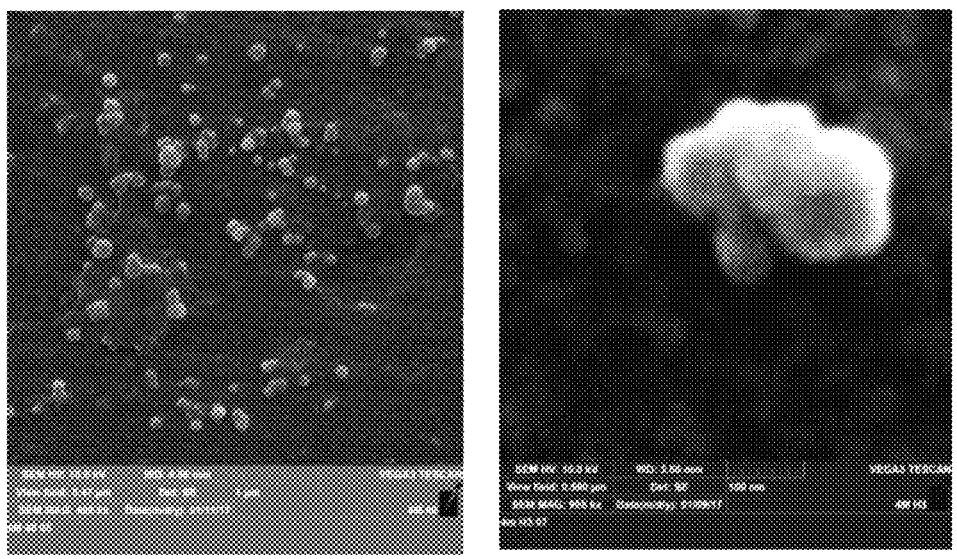
FIG. 5D

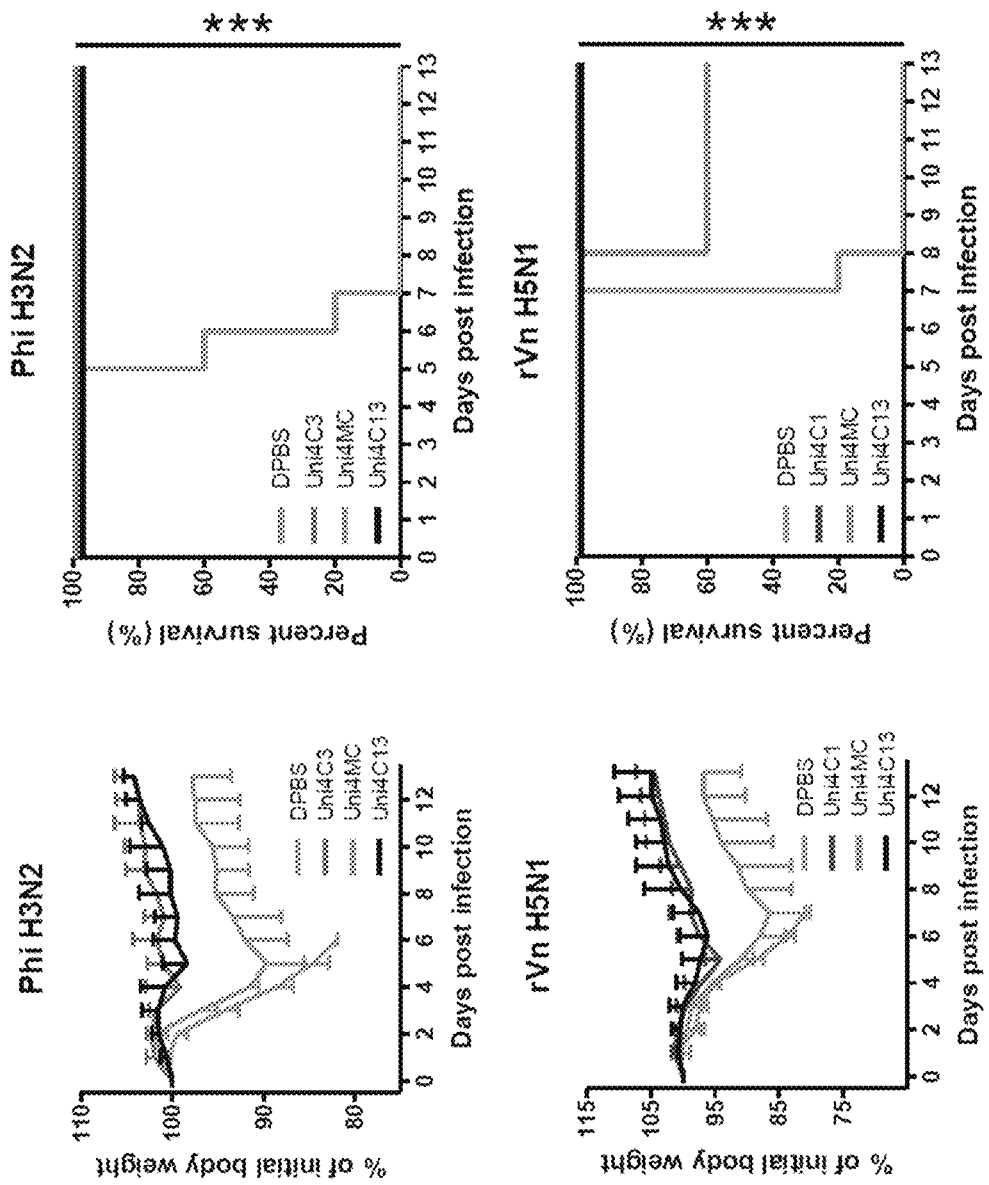
FIG. 7A (cont...)

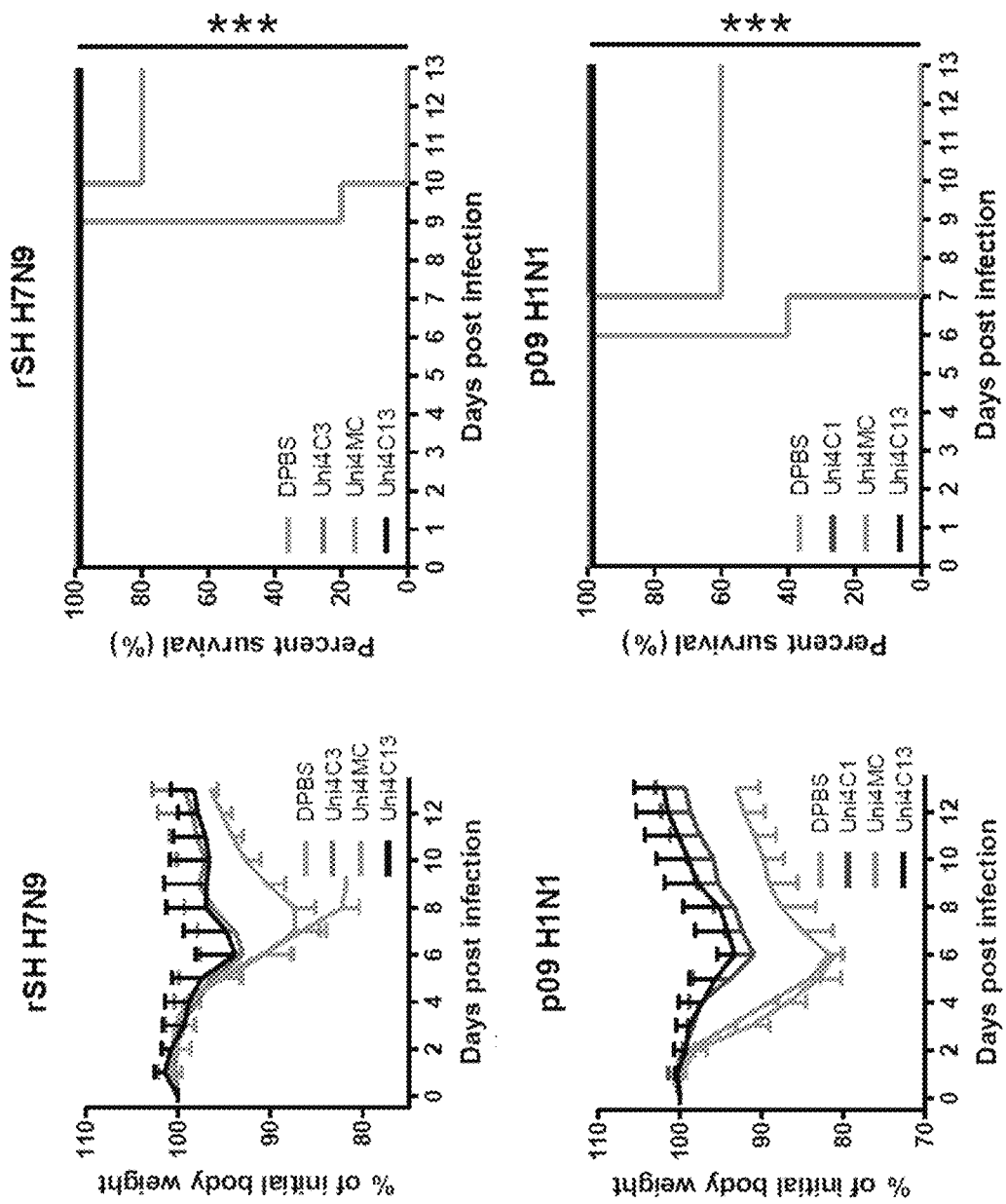
FIG. 7A (cont...)

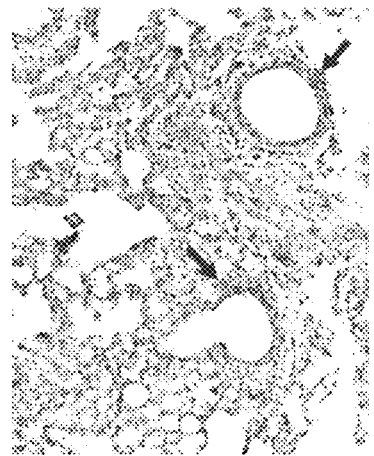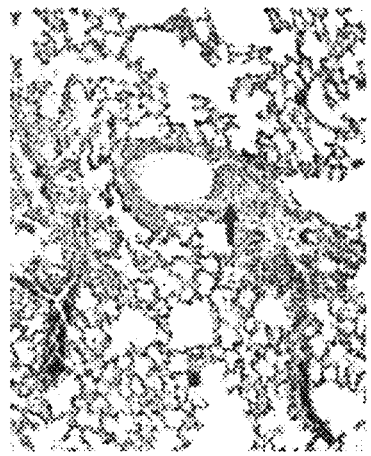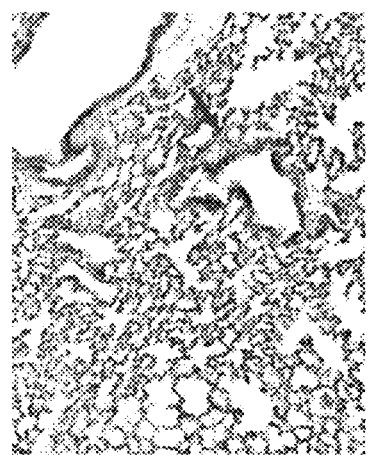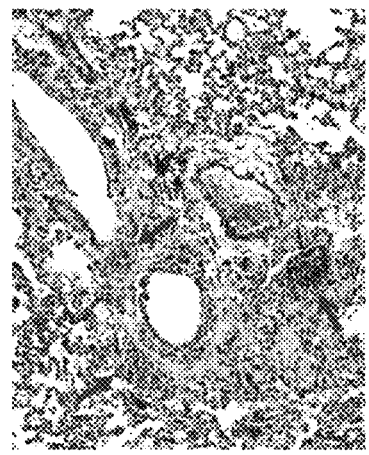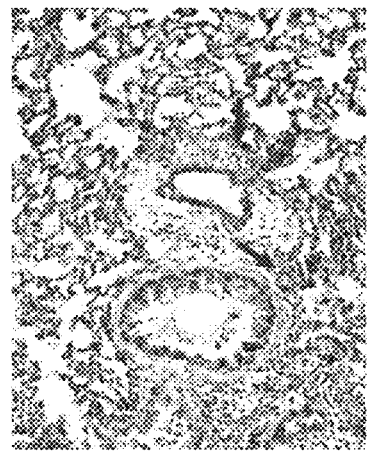
FIG. 8

| Virus subtypes | Pre-challenge sera three weeks post boost | | | | | | | Subunit protein sera or convalescent sera | | | |
|---|---|---|---|---|---|---|---|---|---|---|---|
| | Pre-immune | DPBS | Uni4MC | Uni4C1 | Uni4C3 | Uni4C13 | PR8 H1 | Aic H3 | rVn H5N1 | rSH H7 |
| PR8 H1N1 | <10 | <10 | <10 | <10 | <10 | <10 | 160 | <10 | 40 | <10 |
| Aic H3N2 | <10 | <10 | <10 | <10 | <10 | <10 | <10 | 640 | <10 | <10 |
| rVn H5N1 | <10 | <10 | <10 | <10 | <10 | <10 | <10 | <10 | 160 | <10 |
| rSH H7N9 | <10 | <10 | <10 | <10 | <10 | <10 | <10 | <10 | <10 | 80 |
| p68 H3N2 | <10 | <10 | <10 | <10 | <10 | <10 | <10 | 640 | <10 | <10 |

Low titer ▨ High titer

```
B/Brisbane/60/2008:     1      CTGITSSNSPHVVKTATQGEVNVTGVIPLTTTPTKSHFANLKGTETRGKLCPKCLNCTDL    60
                               |||||||||||||||||||||||||||||
B/hrHA:                 1      CTGITSSNSPHVVKTATQGEVNVTGVIPLTT TGGGGC-----------------------   37

B/Brisbane/60/2008:    61      DVALGRPKCTGKIPSARVSILHEVRPVTSGCFPIMHDRTKIRQLPNLLRGYEHIRLSTHN   120
B/hrHA:                37      ------------------------------------------------------------   37

B/Brisbane/60/2008:   121      VINAENAPGGPYKIGTSGSCPNITNGNGFFATMAWAVPKNDKNKTATNPLTIEVPYICTE   180
B/hrHA:                37      ------------------------------------------------------------   37

B/Brisbane/60/2008:   181      GEDQITVWGFHSDNETQMAKLYGDSKPQKFTSSANGVTTHYVSQIGGFPNQTEDGGLPQS   240
B/hrHA:                37      ------------------------------------------------------------   37

B/Brisbane/60/2008:   241      GRIVVDYMVQKSGKTGTITYQRGILLPQKVWCASGRSKVIKGSLPLIGEADCLHEKYGGL   300
B/hrHA:                37      ------------------------------------------------------------   37

B/Brisbane/60/2008:   301      NKSKPYYTGEHAKAIGNCPIWVKTPLKLANGTKYRPPAKLLKERGFFGAIAGFLEGGWEG   360
                                                    ||||||||||||||||||| ||||||||||||||||||
B/hrHA:                38      ---------------------VKTPLKLANGTKYRPPAKLLTEQGFFGAIAGFLEGGWEG    76

B/Brisbane/60/2008:   36       MIAGWHGYTSHGAHGVAVAADLKSTQEAINKITKNLNSLSELEVKNLQRLSGAMDELHNE   420
                               |||||||||||||||||||||||||||||||||||||||||
B/hrHA:                77      MIAGWHGYTSHGAHGVAVAADLKSTQEAINKITKNLNSLSEL EGGGSS------------   124

B/Brisbane/60/2008:   421      ILELDEKVDDLRADTISSQIELAVLLSNEGIINSEDEHLLALERKLKKMGPSAVEIGNG   480
                               ||||||||||||||| |||||||||||||||||||||||||||||||||||||||||
B/hrHA:               125      ------------ADTICSQIELAVLLSNEGIINSEDEHLLALERKLKKMGPSAVEIGNG   172

B/Brisbane/60/2008:   481      CFETKHKCNQTCLDRIAAGTFDAGEFSLPTFDSLNITAASLNDDGLDNHTILLYYSTAAS   540
                               |||||||||||||||||||||||||||||
B/hrHA:               173      CFETKHKCNQTCLDRIAAGTFDAGEFSLPT PGSSGGSSGMKQIEDKIEEILSKIYHIENE   231

B/Brisbane/60/2008:   541      S------   541
B/hrHA:               232      IARIKKL   239
```

FIG. 18

HEADLESS HEMAGGLUTIN INFLUENZA VACCINE

CROSS-REFERENCE TO RELATED APPLICATIONS

This application is a National Stage of International Application No. PCT/US2018/054335, filed Oct. 4, 2018, which claims benefit of U.S. Provisional Application No. 62/567,936, filed Oct. 4, 2017, which is hereby incorporated herein by reference in its entirety.

STATEMENT REGARDING FEDERALLY SPONSORED RESEARCH OR DEVELOPMENT

This invention was made with Government Support under Grant No. AI101047 awarded by the National Institutes of Health. The Government has certain rights in the invention.

SEQUENCE LISTING

This application contains a sequence listing filed in electronic form as an ASCII.txt file entitled "220702-2450 Sequence Listing_ST25" created on Mar. 31, 2022, having 41,502 bytes. The content of the sequence listing is incorporated herein in its entirety.

BACKGROUND

Seasonal influenza epidemics cause an estimated 250,000 deaths worldwide each year. The global burden of human influenza infection is huge. It was estimated that in 2008 seasonal influenza viruses cause 90 million new infections worldwide in children below 5 years of age and were responsible for up to 20% of all pediatric acute lower respiratory infections. The adaptive immune response that is built up in the human population due to influenza infection creates immune selection pressure on the circulating viruses. Mutant viruses acquire ability to escape from prevailing herd immunity by antigenic drift and shift, which necessitates the yearly update of composition of human influenza vaccines to match the newly circulating viruses. However, the protection efficacy of updated vaccines does not always live up to expectation, for instance the outbreak of pandemic Mexican flu H1N1 in 2009 caused 200,000 deaths during the first 12 months of its circulation. Low vaccine effectiveness was also observed recently during 2012-2013 and 2014-2015 epidemic. In addition, the threat from fatal zoonotic influenza viruses like H5N1 and H7N9 adds further necessity for the development of universal influenza vaccines with broad and long-term protection.

SUMMARY

Disclosed herein are influenza vaccines capable of providing broad cross-protection. Conserved epitopes from influenza virus are promising targets to develop universal vaccines. Notably, the membrane proximal stalk domain of hemagglutinin (HA) is more conserved than the highly variable head domain. Disclosed herein are vaccine compositions and methods based on a truncated influenza HA protein lacking a head domain. For example, disclosed herein is a polypeptide comprising a truncated influenza HA protein lacking at least a portion of the HA head domain, also referred to herein as a head-removed HA (hrHA). Also disclosed is a nanoparticle coated with a hrHA polypeptide. Also disclosed is a virus like particle (VLP) expressing on its surface a hrHA polypeptide.

Also disclosed is a nanoparticle formed by desolvating the fusion protein with a desolvating agent and/or crosslinking a fusion protein with a crosslinking agent, wherein the fusion protein comprises a series of 2 to 8 influenza virus matrix protein 2 extracellular (M2e) domains linked to a multimerization domain. This nanoparticle can in some embodiments be coated with an antigen, such as the disclosed hrHA polypeptide.

Also disclosed are pharmaceutical compositions comprising a polypeptide or nanoparticle disclosed herein and an adjuvant.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A schematically illustrates the PNP formation process by ethanol desolvation with or without DTSSP crosslinking. FIG. 3B illustrates the effect of differing doses of DTSSP crosslinker on PNP size by zeta-sizer with FIG. 3C showing a peak size of 141 nm in the absence of DTSSP altogether. FIG. 3D shows well-maintained primary structure of the fusion protein even after PNP formation and the ability to completely denature the PNP back into monomers. FIG. 3E shows the particulate and nearly-spherical spatial displacement of the PNP by scanning electron microscopy (SEM).

FIGS. 4A to 4C show design of head-removed HA coated PNPs, Uni4C1 and Uni4C3. FIG. 4A schematically illustrates the fabrication process while FIGS. 4B and 4C show hydrophobic and amine-reactive groups present in the hrHA proteins.

FIGS. 5A to 5D show fabrication and characterization of example head-removed HA coated PNPs, Uni4C1 and Uni4C3. Uni3C1 has a peak size of 181 nm (FIG. 5A) while Uni4C3 has a peak size of 211 nm (FIG. 5B). FIG. 5C demonstrates that the hrHA proteins successfully coated the core PNP while FIG. 5D demonstrated PNP spatial characteristics by SEM.

FIG. 6E summarizes these data in a five-axis radar chart.

FIG. 8 shows results of histological analysis of lung sections after viral challenge in either vaccinated or mock-vaccinated mice.

FIG. 9 shows the results of HAI assays of sera from the various immunization regimens either before or after challenge, using numerous influenza virus strains for the inhibition assays.

FIG. 11B shows sequence alignment of hrH1 (SEQ ID NO:43) with A/Puerto Rico/8/1934 H1 (SEQ ID NO:44).

FIGS. 15A and 15B shows example structure of 4M2e-NA nanoparticles. FIG. 15A shows combination of 4M2e and 4M2e-NA fusion proteins. GS linker: glycine and serine GGSGGG (SEQ ID NO:20); M2e: combined M2e sequence from human, swine, wild bird, and domestic fowl with tetrabrachion together; M2e+NA: combined stalk and head of neuraminidase 1 (from A/Vietnam/1203/2004/) with M2e above. FIG. 15B shows schematic formation of M2e-NA nano-particle. 4M2e-NA was covered on the 4M2e core.

FIGS. 16A to 16F show the formation of M2e-NA nanoparticle. FIG. 16A shows M2e-NA fusion protein cross-linked by 12.5, 7.5, 2.5, and 1 mM of BS3, as in line 1, 2, 3, 4, respectively. Line 5: soluble M2e+NA fusion protein. FIG. 16B shows Coomassie blue staining of M2e-NA nanoparticle. FIGS. 16C and 16D show Western blot assay of M2e-NA nanoparticle. C: M2e antibody; D: NA antibody. FIG. 16E shows the size of formed M2e+NA nanoparticle: 198.2+/−62.41 nm. FIG. 16F shows results of a neuraminidase activity test. The concentration of each protein: M2e+ NA nano particle: 1 mg/ml; soluble M2e+NA: 1 mg/ml; H5N1 virus: 2.5 mg/ml; BSA: 2 mg/ml.

FIG. 18 displays the sequence alignment of B/hrHA (SEQ ID NO:40) with the HA sequence from Influenza B strain B/Brisbane/60/2008 (SEQ ID NO:39). The glycine-rich linkers are marked in bold letters and the GCN4 trimerization domain in the C terminal tail is marked in italics.

DETAILED DESCRIPTION

Figure 1A:
FIGS. 1A to 1C show schematic and sequence designs of recombinant 4M2e-GCN4 (SEQ ID NO:38) and structural designs of original the H1 and H3 HA proteins as well as the head-removed H1 and head-removed H3 that have been engineered using the originals as a starting structure.
Figure 1B:
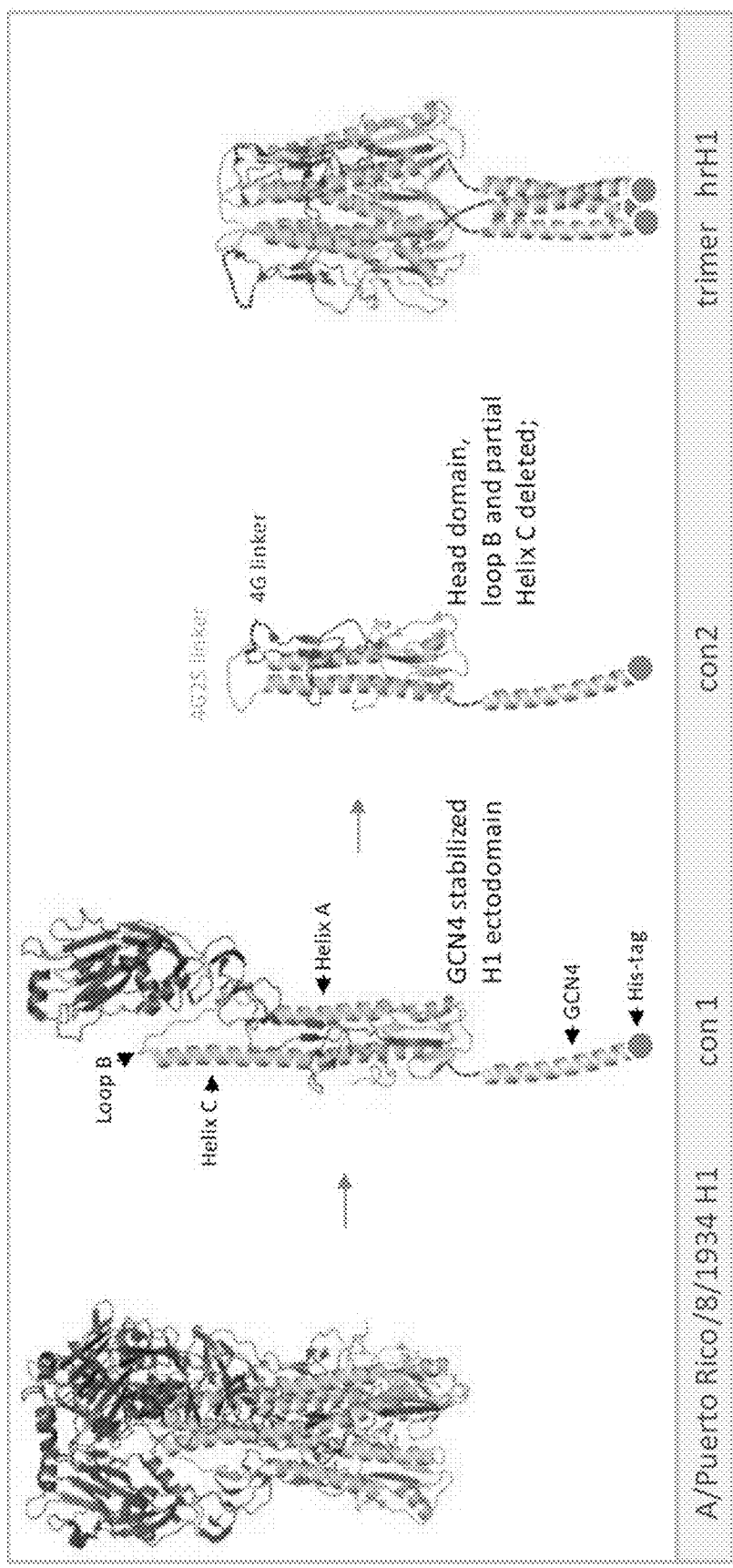
Figure 1C:
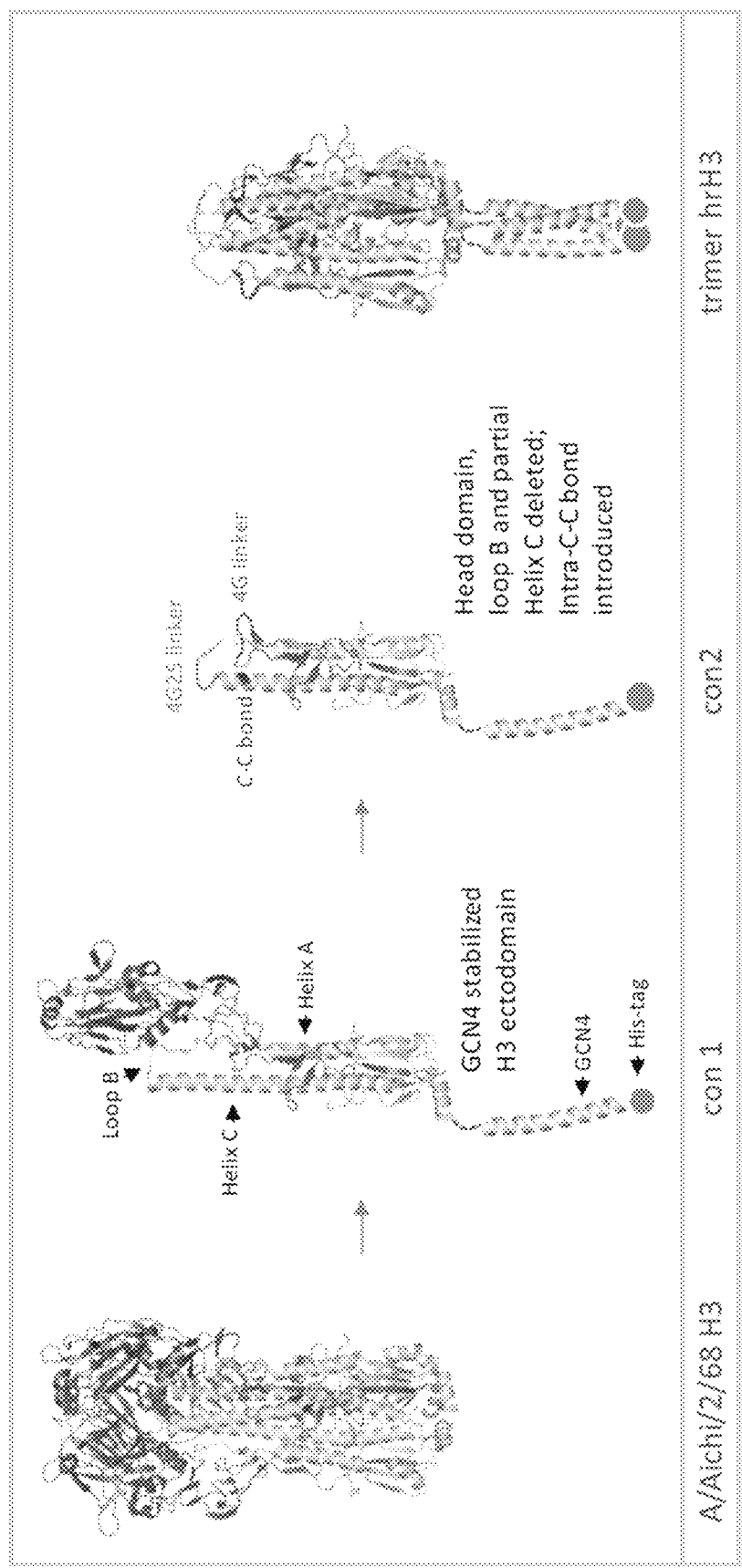

Current influenza vaccines provide limited protection against seasonal strains of influenza A viruses owing to the ability to escape from immune pressure through rapid antigenic drift and re-assortment. The conserved epitopes from influenza virus are promising targets to develop universal vaccine. Hemagglutinin (HA) is the predominant protein on the surface of influenza viruses, is highly antigenic, and is the dominant target for humoral immune responses that give rise to anti-influenza antibodies. On the exterior of the virus, HA is divided into two domains: the head domain, which is highly variable in sequence, and the membrane proximal stalk domain that is more conserved. Antibodies formed against the head domain can often neutralize the virus while antibodies against the stalk domain typically do not. The humoral immune response to influenza is therefore commonly dominated by antibodies against the head domain, potentially resulting in neutralization of that strain of virus, but providing very narrowly-limited or no immunity against other strains. An immune response against a more conserved domain of HA could provide immunity against numerous strains and variants of the virus. Given these considerations, a vaccine was designed and produced using an HA that has had the variable head removed while keeping the conserved stalk domain. To increase immunogenicity of this head-removed HA (hrHA), a nanotechnology approach was used to produce a nanocluster protein nanoparticle (PNP) vaccine displaying the hrHA protein as a coat on the surface of the PNP. These vaccines can fully protect against influenza viruses expressing divergent HA.

Definitions

It must be noted that as used herein and in the appended claims, the singular forms "a," "an," and "the" include plural referents unless the context clearly dictates otherwise. Thus, for example, reference to "a peptide" includes a plurality of such peptides, reference to "the peptide" is a reference to one or more peptides and equivalents thereof known to those skilled in the art, and so forth.

In this specification and in the claims that follow, reference will be made to a number of terms that shall be defined to have the following meanings:

"Optional" or "optionally" means that the subsequently described event or circumstance can or cannot occur, and that the description includes instances where the event or circumstance occurs and instances where it does not. For example, the phrase "optionally a signal peptide" means that the signal peptide may or may not be included.

The term "universal influenza vaccine" refers to vaccine capable of providing cross-protection against at least two, including three, four, five or more, strains or subtypes of influenza.

The term "individual," "host," "subject," and "patient" are used interchangeably to refer to any individual who is the target of administration, treatment, or vaccination. The subject can be a vertebrate, for example, a mammal. Thus, the subject can be a human or veterinary patient.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The terms "peptide," "protein," and "polypeptide" are used interchangeably to refer to a natural or synthetic molecule comprising two or more amino acids linked by the carboxyl group of one amino acid to the alpha amino group of another.

The term "protein domain" refers to a portion of a protein, portions of a protein, or an entire protein showing structural integrity; this determination may be based on amino acid composition of a portion of a protein, portions of a protein, or the entire protein.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and the nucleic acid can include deoxyribonucleic acid (DNA) or ribonucleic acid (RNA).

The term "variant" refers to an amino acid sequence having conservative amino acid substitutions, non-conservative amino acid substitutions (i.e. a degenerate variant), or a peptide having 60%, 65%, 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence identity to the recited sequence.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods. For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

"Homolog" and "homologous" as used herein refer to sequences that derive from a recent common ancestor and therefore maintain a level of percent sequence identity that is commonly understood in the art.

"Heterologous" refers to sequences that encode for the same protein (in the case of nucleic acids) or that are demonstrably the same protein (in the case of polypeptides), yet in which such sequences are not derived from a recent common ancestor and maintain a level of percent sequence identity that is less than 100%.

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

A "spacer" as used herein refers to a peptide that joins the proteins of a fusion protein. Generally a spacer has no specific biological activity other than to join the proteins or to preserve some minimum distance or other spatial relationship between them. However, the constituent amino acids of a spacer may be selected to influence some property of the molecule, such as the folding, net charge, or hydrophobicity of the molecule.

An "antigen" refers to a substance that can act as the target of an immune response. As used herein, "antigen" refers to a biological substance, and may consist of a peptide, a polypeptide or protein, a glycoprotein, a saccharide or polysaccharide, a lipid, a nucleic acid, or another biological or bioactive compound, amongst other biological substances.

The "ectodomain" of a protein refers to the domain of a membrane protein that extends into the extracellular space or is found on the exterior surface of a viral particle.

The "transmembrane" domain of a protein refers to the domain of a membrane protein that passes through the biological membrane and directly interfaces laterally with the phospholipid bilayer of the membrane.

The "cytoplasmic" domain, also known as an "intracellular" domain, is the domain of an integral membrane protein that extends into the intracellular space or is found in the interior space of a virus.

A "strain" of influenza as used herein refers to a lineage of the virus with defined and durable antigenic parameters. Each type of influenza (Influenza A, B, C, and D) consists of numerous strains that differ from one another in their antigen sequences.

A "subtype" of influenza A virus refers to the division of influenza A into categories based on the sequence of the viral HA and neuraminidase (NA) proteins. For example, an influenza A virus can have an H1 sequence of its HA protein and an N1 sequence of its NA protein and would therefore be categorized as an H1N1 subtype of influenza. Other subtype examples include H3N2, H5N1, H7N9, and H9N2.

Headless HA Polypeptide

Disclosed herein is a polypeptide comprising a truncated influenza hemagglutinin (HA) protein lacking a head domain (a head-removed HA (hrHA) polypeptide). The HA protein can be of any subtype and from any strain. The following is the amino acid sequence for the influenza A H3 stalk ectodomain: MKTIIALSYIFCLPLGQDLPGNDN-
STATLCLGHHAVPNGTLVKTITDDQIEVT-
NATELVQSSST GKICNNPHRILDGIDCTL-
IDALLGDPHCDVFQNETWDLFVERSKAFSNCYPYD-
VPDYASLRS LVASSGTLEFITEGFTWTGVTQNGG-
SNACKRGPGSGFFSRLNWLTKSGSTYPVLNVTMPN
NDNFDKLYIWGIHHPSTNQEQTSLYVQAS-
GRVTVSTRRSQQTIIPNIGSRPWVRGLSSRISIY
WTIVKPGDVLVINSNGNLIAPRGYFKMRTGKS-
SIMRSDAPIDTCISECITPNGSIPNDKPFQN VNKI-
TYGACPKYVKQNTLKLATGMRNVPEKQTRGLFGA-
IAGFIENGWEGMIDGWYGFRHQ
NSEGTGQAADLKSTQAAIDQINGKLNRVIEKT-
NEKFHQIEKEFSEVEGRIQDLEKYVEDTKID LWSYN- AELLVALENQHTIDLTDSEMNKLFEKTRRQLRE-
NAEEMGNGCFKIYHKCDNACIESI
RNGTYDHDVVYRDEALNNRFQIKGVELKSGYK (SEQ ID NO:15). The corresponding amino acid sequences for other HA subtypes are known. Therefore, reference to specific amino acids within SEQ ID NO:15 is also a reference to the corresponding amino acids in the known amino acid sequences for the other subtypes.

In some embodiments, the disclosed polypeptide lacks at least the HA amino acids corresponding to residues 65 to 320 of SEQ ID NO:15. In some embodiments, the disclosed polypeptide lacks at least the HA amino acids corresponding to residues 62 to 322 of SEQ ID NO:15. In some embodiments, the disclosed polypeptide lacks at least the HA amino acids corresponding to residues 62 to 320 of SEQ ID NO:15. In some embodiments, the disclosed polypeptide lacks at least the HA amino acids corresponding to residues 62 to 321 of SEQ ID NO:15. In some embodiments, the disclosed polypeptide lacks at least the HA amino acids corresponding to residues 63 to 320 of SEQ ID NO:15. In some embodiments, the disclosed polypeptide lacks at least the HA amino acids corresponding to residues 63 to 321 of SEQ ID NO:15. In some embodiments, the disclosed polypeptide lacks at least the HA amino acids corresponding to residues 63 to 322 of SEQ ID NO:15. In some embodiments, the disclosed polypeptide lacks at least the HA amino acids corresponding to residues 64 to 320 of SEQ ID NO:15. In some embodiments, the disclosed polypeptide lacks at least the HA amino acids corresponding to residues 64 to 321 of SEQ ID NO:15. In some embodiments, the disclosed polypeptide lacks at least the HA amino acids corresponding to residues 64 to 322 of SEQ ID NO:15. In some embodiments, the disclosed polypeptide lacks at least the HA amino acids corresponding to residues 65 to 321 of SEQ ID NO:15. In some embodiments, the disclosed polypeptide lacks at least the HA amino acids corresponding to residues 65 to 322 of SEQ ID NO:15.

Methods and compositions disclosed herein for the sequence of any particular HA are applicable to the sequences of other HA. Methods and compositions from any of the particular HA delineated in this specification may be adapted routinely to another HA for those skilled in the art. Thus, in one embodiment, a sequence for influenza A HA is used for production of hrHA. In one embodiment, a sequence for influenza B HA is used for production of hrHA. In one embodiment, a sequence for influenza A H1 HA is used for production of hrHA. In one embodiment, a sequence for influenza A H1, H3, H5, H7 or H9 HA is used for production of hrHA.

In some embodiments, the disclosed polypeptide is a fusion protein. Fusion proteins, also known as chimeric proteins, are proteins created through the joining of two or more genes which originally coded for separate proteins. Translation of this fusion gene results in a single polypeptide with functional properties derived from each of the original proteins. Recombinant fusion proteins can be created artificially by recombinant DNA technology for use in biological research or therapeutics.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein. For example, the head domain of HA has a function in the binding to proteins on a cell's surface and in fusion of the viral particle with the cell, while the stalk domain of HA has a structural role in placing the head domain in space away from the viral membrane.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either, or only a portion of both.

To create an antigenic HA that consists of the conserved stalk domain in the absence of the variable head domain, the head domain is removed from the HA sequence, resulting in hrHA. In order to maintain the overall structural integrity of HA in the absence of the head domain, the head domains in HA are preferably replaced with linkers (or "spacers") that do not affect the secondary structure of the HA protein. For example, the head domain can be replaced by a linker 3 to 5 amino acids in length that do not form a fixed secondary structure. In some embodiments, the linker comprises 3 to 5 amino acids selected from glycine, alanine, and serine. In particular embodiments, the linker is selected from the group consisting of GGG, GGGG (SEQ ID NO:16), GGGGG (SEQ ID NO:17), and GGGGC (SEQ ID NO:18), GGGSS (SEQ ID NO:19).

In some embodiments, the hrHA polypeptide comprises the transmembrane and cytoplasmic domains of HA. In some embodiments, the polypeptide lacks the HA transmembrane and/or cytoplasmic domains of HA, and instead the polypeptide comprises a heterologous membrane-anchoring sequence. For example, the heterologous membrane-anchoring sequence can be a glycosylphosphatidylinositol (GPI) membrane-anchoring sequence. In some embodiments, the hrHA polypeptide lacks the HA transmembrane and/or cytoplasmic domain and consists only of the ectodomain or some proportion of the ectodomain.

In some embodiments, the hrHA polypeptide is a stand-alone protein. In some embodiments, the hrHA polypeptide is a stand-alone protein that is not fused to another protein or protein domain. In some embodiments, the hrHA polypeptide is a domain that is fused together with another protein or protein domain to form a fusion protein. In some embodiments, the hrHA polypeptide forms a fusion protein with an oligomerization domain. In some embodiments, the hrHA polypeptide forms a fusion protein with a GCN4 oligomerization domain. In some embodiments, the hrHA polypeptide forms a fusion protein with a GCN4 oligomerization domain that forms trimers. In some embodiments, the hrHA polypeptide forms a fusion protein with a GCN4 oligomerization domain that forms dimers or tetramers.

Also disclosed is a nanoparticle that is coated with a disclosed hrHA polypeptide. In some cases, the hrHA polypeptide is crosslinked to a polymer nanoparticle surface. In embodiments, the hrHA polypeptide is absorbed onto the nanoparticle surface. In some embodiments, the hrHA polypeptide is absorbed onto the nanoparticle surface and then crosslinked to the nanoparticle surface. In some embodiments, the hrHA polypeptide is encapsulated into the nanoparticle. In particular embodiments, the nanoparticle is formed from a biocompatible polymer. Examples of biocompatible polymers include polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, or combinations thereof. In some cases, the nanoparticle is formed from a polyethylene glycol (PEG), poly(lactide-co-glycolide) (PLGA), polyglycolic acid, poly-beta-hydroxybutyrate, polyacrylic acid ester, or a combination thereof. In embodiments, the nanoparticle is formed from polypeptides. In some embodiments, the nanoparticle is formed by desolvation of polypeptides. In some embodiments, the nanoparticle is formed by desolvation of polypeptides into protein aggregates. In some embodiments, the nanoparticle is formed by desolvation of polypeptides into protein aggregates with defined physicochemical characteristics that are directly determined by the parameters of the treatment methods used for desolvation.

Virus Like Particles (VLPs)

Also disclosed is a composition comprising a virus like particle (VLP) expressing on its surface a disclosed hrHA polypeptide. For example, the disclosed fusion proteins may be incorporated into virus-like particles (VLPs) by including within the fusion protein a membrane anchor domain, such as a transmembrane domain and optional cytoplasmic domain of a viral envelope protein.

Non-replicating VLPs resemble infectious virus particles in structure and morphology, and contain immunologically relevant viral structural proteins. VLPs have been produced from both non-enveloped and enveloped viruses. Envelopes of VLPs are derived from the host cells similar to the way as enveloped viruses such as influenza A virus obtain their lipid envelopes from their host cells. Therefore, membrane-anchored proteins on the surfaces of enveloped viruses will be expressed in a native-like conformation if they are expressed in a membrane-anchored form.

Influenza VLPs involve lipid bilayers and host cell membrane proteins (Song, J. M., et al. J Proteome Res 2011 10:3450-3459). For example, Influenza VLPs containing the wild type M2 protein have been described (Song, J. M., et al. Proc Natl Acad Sci USA 2011 108:757-761; Song, J. M., et al. PLoS One 2011 6:e14538). Enveloped VLPs may be composed of influenza matrix 1 (M1) protein as a particle forming core. These VLPs are produced, for example, by coinfecting insect cells with one or more recombinant baculoviruses co-expressing M1 proteins and the disclosed fusion proteins, culturing the insect cells under physiological conditions, and purifying the VLPs from insect cell culture supernatants.

Nanoparticle

A nanoparticle is a particle between 1 and 100s of nanometers in size. A nanoparticle can be natural or synthetic. A nanoparticle can be created from biological molecules or from abiological molecules. A nanoparticle has a core containing the material of which the nanoparticle consists. A nanoparticle has a surface that is the interface between the core and the space and/or solution outside of the core. A protein nanoparticle (PNP) is a particle in which the core material consists of protein. PNP can be synthesized in numerous ways. For example, PNP can be synthesized by desolvation of a solution of soluble protein, resulting in precipitation of particulate PNP. PNP can be synthesized by crosslinking proteins to form the particle. PNP can be synthesized by biochemical aggregation based on autonomouns protein-protein interactions. PNP can be formed by a combination of any of these PNP synthesis methods.

Disclosed herein is a nanotechnology approach to produce a nanocluster PNP. In one embodiment, the PNP consists of a protein antigen that can act as a target of an immune response. In one embodiment, the PNP can be used as an active pharmaceutical ingredient in a vaccine. In one embodiment, the PNP is an uncoated particle. In one embodiment, the PNP is coated with another protein antigen on its surface. In one embodiment, the PNP formed by desolvating the core protein with a desolvating agent and/or crosslinking a core protein with a crosslinking agent. Both or either of these procedures can be used to make double-layered nanoparticles. In some cases, the nanoparticle contains a core structure formed by desolvation and a coating formed by crosslinking of a surface antigen. Suitable desolvating agents include, for example, ethanol, acetone, or combinations thereof.

A humoral immune response is preferentially mounted against proteins, domains, and epitopes that are displayed in a repetitive and/or iterative fashion. Forming a PNP from a protein results in a particle with many repetitive epitopes on the surface of the PNP. In this way, formation of a PNP from a soluble protein results in a substance that is much more highly antigenic for initiating and/or promoting an immune response than the soluble protein alone and yet consists of biological substituents that are identical or nearly-identical to the soluble protein alone. Thus formation of PNP from a soluble protein results in a composition that much more readily promotes humoral immune responses to that protein.

It is possible to modify a PNP consisting of a core protein by adding a coat of a second protein onto the surface of the PNP. This method leverages the same principle of promoting effective humoral immune responses toward repetitive epitopes yet has the benefit of directing an additional humoral immune response against the second protein that coats the PNP.

The core protein is preferably a protein with a strong T cell epitope. In some embodiments, the core protein comprises conserved T cell epitopes from influenza NP, M1, or a combination thereof. In some embodiments, the core protein comprises one or more influenza virus matrix protein 2 (M2) domains. In some embodiments, the core protein comprises one or more influenza virus matrix protein 2 extracellular (M2e) domains. In some embodiments, the core protein is a fusion protein comprising a series of 2, 3, 4, 5, 6, 7, or 8 M2e domains, optionally linked to a multimerization domain.

In some embodiments, the core protein comprises two or more (e.g., 2, 3, 4, 5, 6, 7, 8, 9, 10 or more) different influenza M2e domains (i.e., heterologous M2e domains). In some embodiments, the core protein comprises two or more homologous influenza M2e domains. In some embodiments, the core protein comprises a mixture of two or more homologous and/or heterologous influenza M2e domains. The core protein can contain heterologous M2e domains to increase antigenicity and cross-protection. By taking into account the mechanisms of effective T cell responses against immunologically active antigens, the use of heterologous M2e is herein purposely designed to increase immune cross-protection. In one embodiment, the core protein can contain one or more M2e domains from a human influenza, one or more M2e domains from a swine influenza, and one or more M2e domains from an avian influenza. As an example, the core protein can contain the following five influenza M2e sequences: 2×Human, 1×Swine, 1× Avian Type I, and 1× Avian Type II.

In one embodiment, the core protein can contain one or more M2e domains from a human influenza A subtype, one or more M2e domains from a swine influenza A subtype, and one or more M2e domains from an avian influenza A subtype. As an example, the core protein can contain the following five influenza A virus subtype M2e sequences: 2× Human, 1× Swine, 1× Avian Type I, and 1× Avian Type II.

In one embodiment, the core protein can contain one or more M2e domains from a human influenza B subtype, one or more M2e domains from a swine influenza B subtype, and one or more M2e domains from an avian influenza B subtype. As an example, the core protein can contain the following five influenza B virus subtype M2e sequences: 2× Human, 1× Swine, 1× Avian Type I, and 1× Avian Type II.

Methods and compositions disclosed herein for the sequence of any particular M2e are applicable to the sequences of other M2e. Methods and compositions from any of the particular M2e delineated in this specification may be adapted routinely to another M2e for those skilled in the art. Thus, in one embodiment, a sequence for influenza A M2e is used. In one embodiment, a sequence for influenza B M2e is used. In one embodiment, a combination of sequences for influenza A M2e and influenza B M2e are used.

In some embodiments, the human M2e sequence comprises the amino acid sequence PIRNEWGSRSN (SEQ ID NO:21), or a conservative variant thereof having at least about 70%, 80%, or 90% sequence identity to SEQ ID NO:21 (i.e., one, two, or three conservative amino acid substitutions). For example, human M2e isolates H1N1 (A/PR8, A/NC/99) and H3N2 (A/Phil/82) have the amino acid sequence SLLTEVET PIRNEWGSRSN DSSD (SEQ ID NO:22).

In some embodiments, the swine M2e sequence comprises the amino acid sequence PTRSEWESRSS (SEQ ID NO:23), or a conservative variant thereof having at least 70%, 80%, or 90% sequence identity to SEQ ID NO:23. For example, swine M2e isolates from the 2009 H1N1 pandemic (A/California/4/2009) have the amino acid sequence SLLTEVET PTRSEWESRSS DSSD (SEQ ID NO:24).

In some embodiments, the avian M2e sequence (referred to herein as "avian type I") comprises the amino acid sequence PTRX$_1$X$_2$WESRSS (SEQ ID NO:25), wherein X$_1$ is N, H, or K, wherein X$_2$ is E or G, or a conservative variant thereof having at least 70%, 80%, or 90% sequence identity to SEQ ID NO:25. For example, avian type I M2e isolates from H5N1 (A/Vietnam/1203/04, A/Indonesia/05, A/mandarin/kr/2010, A/ck/kr/2006) have the amino acid sequence SLLTEVET PTRNEWESRSS DSSD (SEQ ID NO:26). Avian type I M2e isolates from H7N3 (A/dk/Kr/2007), H9N2 (A/ck/Kr/2012) have the amino acid sequence SLLTEVET PTRNGWECRCS DSSD (SEQ ID NO:27). Avian type I M2e isolates from H5N1 (A/ck/Kr/Gimje/2008) have the amino acid sequence SLLTEVET PTRHEWECRCS DSSD (SEQ ID NO:28). Avian type I M2e isolates from H5N1 (A/ck/Vietnam/2011) have the amino acid sequence SLLTEVET PTRKEWECRCS DSSD (SEQ ID NO:29).

In some embodiments, the avian M2e sequence (referred to herein as "avian type II") comprises the amino acid sequence LTRNGWGCRCS (SEQ ID NO:30), or a conservative variant thereof having at least 70%, 80%, or 90% sequence identity to SEQ ID NO:30. For example, avian type II M2e isolates from H5N1 (A/HK/156/97), H9N2 (A/HK/1073/99) have the amino acid sequence SLLTEVET LTRNGWGCRCS DSSD (SEQ ID NO:31).

The core protein may further comprise a signal peptide at the N-terminus to facilitate secretion. For example, the core protein may contain a mellitin signal peptide. In some embodiments, the melittin signal peptide has the amino acid sequence MKFLVNVALVFMVVYISYIYADPINMT (SEQ ID NO:32), or a conservative variant thereof having at least 72%, 76%, 80%, 84%, 88%, 92%, or 96% sequence identity to SEQ ID NO:32. Alternatively, the fusion protein may contain a baculovirus gp64 signal peptide (MVSAIVLYVL-LAAAAHSAFA, SEQ ID NO:33) or a chitinase signal peptide (MPLYKLLNVLWLVAVSNAIP, SEQ ID NO:34) (Wang, B., et al. J Virol 2007 81: 10869-10878), or a conservative variant thereof having at least 70%, 75%, 80%, 85%, 90%, or 95% sequence identity to SEQ ID NO:33 or SEQ ID NO:34.

Influenza M2 is naturally a homotetramer. The M2e domain itself lacks the sequences for naturally forming a homotetramer. Therefore, in some embodiments, the fusion protein containing M2e also contains a multimerization domain, such as a tetramerization domain. An example of a suitable tetramerization domain includes a GCN4 (a leucine zipper tetramerization motif found in yeast proteins). For example, the GCN4 domain can have the amino acid sequence GGLKQIEDKLEEILSKLYHIENELARIK-KLLGE (SEQ ID NO:35), or a conservative variant thereof having at least 70%, 73%, 76%, 79%, 82%, 85%, 88%, 91%, 94%, or 97% sequence identity to SEQ ID NO:36. In particular embodiments, the M2e fusion protein contains a GCN4 tetramerization domain. Other identified tetramerization domains include tetrabrachion protein, tumor suppressor p53 tetramerization domain, C-terminal 40-residue peptide of the AChE (tryptophan amphiphilic tetramerization (WAT) domain), erythrocyte spectrin tetramerization domain, and Mnt repressor tetramerization domain. In some embodiments, the M2e fusion protein contains one or more of these other identified tetramerization domains.

In some embodiments, the series of M2e domains are linked to the N-terminus of the multimerization domain. In some embodiments, the series of M2e domains are linked to the C-terminus of the multimerization domain. In some embodiments, the core protein comprises a series of 2 to 8 M2e domains linked to the N-terminus of the multimerization domain and/or a series of 2 to 8 M2e domains linked to the C-terminus of the multimerization domain.

In some embodiments, the core protein further comprises influenza neuraminidase (NA) protein linked to the multimerization domain. In some embodiments, the series of 2 to 8 M2e domains are linked to the N-terminus of the multimerization domain and/or the NA protein is linked to the C-terminus of the multimerization domain.

The M2e domains can be linked to each other by a flexible linker. Likewise, in some embodiments, the multimerization domain is linked to the M2e domains, the NA protein, or any combination thereof, by a flexible linker. Suitable flexible linkers can be, for example, a peptide having 3, 4, 5, 6, 7, 8, or 9 amino acid selected from glycine, alanine, and serine. For example, the flexible linker can have the amino acid sequence GGSGGG (SEQ ID NO:20).

The disclosed nanoparticle can be used by itself, or it can be coated with another antigen, such as an influenza antigen. This nanoparticle can in some embodiments be coated with the disclosed hrHA polypeptide. In some embodiments, the antigen is coated on the nanoparticle using a crosslinking agent. In some embodiments, the antigen is absorbed onto the nanoparticle surface. In some embodiments, the antigen is absorbed onto the nanoparticle surface followed by covalent crosslinking of the antigen to the nanoparticle surface using a crosslinking agent.

Crosslinking agents suitable for crosslinking the core protein to produce the nanoparticle, or to coat an antigen on the nanoparticle are known in the art, and include those selected from the group consisting of formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfydryl addition or disulfide reduction, carbohydrate reactive crosslinkers, carboxyl reactive crosslinkers, photoreactive crosslinkers, cleavable crosslinkers, AEDP, APG, BASED, BM(PEO)3, BM(PEO)4, BMB, BMDB, BMH, BMOE, BS3, BSOCOES, DFDNB, DMA, DMP, DMS, DPDPB, DSG, DSP, DSS, DST, DTBP, DTME, DTSSP, EGS, HBVS, sulfo-BSOCOES, Sulfo-DST, and Sulfo-EGS.

Vaccine Compositions

Disclosed are vaccine compositions that comprise one or more of the polypeptides or nanoparticles described above. Although not required, the vaccine compositions optionally contain one or more immunostimulants. An immunostimulant refers to essentially any substance that enhances or potentiates an immune response (antibody or cell-mediated) to an exogenous antigen. One preferred type of immunostimulant is an adjuvant.

Many adjuvants contain a substance designed to protect the antigen from rapid catabolism, such as aluminum hydroxide or mineral oil, and a stimulator of immune responses, such as lipid A, Bortadella pertussis- or Mycobacterium tuberculosis-derived proteins. The adjuvant may be a submicron oil-in-water emulsion of a metabolizable oil and an emulsifying agent. For example, the adjuvant may comprise MF59™, which is a submicron oil-in-water emulsion of a squalene, polyoxyethylene sorbitan monooleate (Tween™ 80) and sorbitan trioleate. The adjuvant may also be a combination of the TLR4 agonist MPL (3-O-desacyl-4'-monophosphoryl lipid A) and aluminum salt, e.g., AS04 (GlaxoSmithKline, Philadelphia, Pa.).

Certain adjuvants are commercially available as, for example, Freund's Incomplete Adjuvant and Complete Adjuvant (Difco Laboratories, Detroit, Mich.); Merck Adjuvant 65 (Merck and Company, Rahway, N.J.); AS01, AS02, AS03, and AS04 (GlaxoSmithKline, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

The adjuvant composition can be a composition that induces an anti-inflammatory immune response (antibody or cell-mediated). Accordingly, high levels of anti-inflammatory cytokines are produced as a result of adjuvant administration. Anti-inflammatory cytokines may include, but are not limited to, interleukin 4 (IL-4), interleukin 5 (IL-5), interleukin 10 (IL-10), and transforming growth factor beta (TGFβ).

The adjuvant composition can be a composition that induces an inflammatory immune response (antibody or cell-mediate). Accordingly, high levels of inflammatory cytokines are produced as a result of adjuvant administration. Inflammatory cytokines may include, but are not limited to, interleukin 1 alpha (IL-α), interleukin 1 beta (IL-ß), interferon gamma (IFNγ), and tumor necrosis factor alpha (TNFα). Optionally, an inflammatory response would be mediated by CD4+ T helper cells. Bacterial flagellin has been shown to have adjuvant activity (McSorley et al., J. Immunol. 169:3914-19, 2002). Also disclosed are polypeptide sequences that encode flagellin proteins that can be used in adjuvant compositions.

Optionally, the adjuvants increase lipopolysaccharide (LPS) responsiveness. Illustrative adjuvants include but are not limited to, monophosphoryl lipid A (MPL), aminoalkyl glucosaminide 4-phosphates (AGPs), including, but not limited to RC-512, RC-522, RC-527, RC-529, RC-544, and RC-560 (Corixa, Hamilton, Mont.).

In addition, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a subject will support an immune response that includes Th1- and Th2-type responses. Optionally, the level of Th1-type cytokines will increase to a greater extent than the level of Th2-type cytokines. The levels of these cytokines may be readily assessed using standard assays. Certain adjuvants for eliciting a predominantly Th1-type response include, for example, a combination of monophosphoryl lipid A, preferably 3-de-O-acylated monophosphoryl lipid A, together with an aluminum salt adjuvants are available from Corixa Corporation (Seattle, Wash.). CpG-containing oligonucleotides (in which the CpG dinucleotide is unmethylated) also induce a predominantly Th1 response. Another adjuvant comprises a saponin, such as Quil A, or derivatives thereof, including QS21 and QS7 (Aquila Biopharmaceuticals Inc., Framingham, Mass.); Escin; Digitonin; or Gypsophila or Chenopodium quinoa saponins.

Additional illustrative adjuvants for use in the disclosed vaccine compositions include Montamide ISA 720 (Seppic, France), SAF (Chiron, Calif., United States), ISCOMS (CSL), MF-59 (Chiron), the SBAS series of adjuvants (e.g., SBAS-2 or SBAS-4, available from GlaxoSmithKline, Philadelphia, Pa.), Detox (Enhanzyn™) (Corixa, Hamilton, Mont.), RC-529 (Corixa, Hamilton, Mont.) and other aminoalkyl glucosaminide 4-phosphates (AGPs).

In some embodiments, the adjuvant is a virosome (e.g. Berna Biotech). In some embodiments, the adjuvant comprises a CpG 1018 and/or CpG 7909 oligonucleotide. In some embodiments, the adjuvant comprises a Imidazoquinoline. In some embodiments, the adjuvant comprises a Polyinosinic:polycytidylic acid (PolyI:C). In some embodiments, the adjuvant comprises a Pam3Cys. In some embodiments, the adjuvant comprises a ISCOMATRIX adjuvant. In some embodiments, the adjuvant comprises a CAF01 and/or IC31 adjuvant. In some embodiments, the adjuvant comprises a Sigma adjuvant system (MPL from Salmonella minnesota, synthetic trehalose dicorynomycolate and squalene oil). In some embodiments, the adjuvant comprises TITERMAX (water-in-oil emulsion, consisting of squalene, sorbitan monooleate 80, a block copolymer and microparticulate silica).

In some embodiments, the adjuvant is incorporated into the VLP in a membrane-anchored form. For example, GM-CSF or a bacterial flagellin protein containing a membrane anchor can be incorporated into the disclosed VLPs.

Pharmaceutical Compositions

The disclosed vaccines can be used therapeutically in combination with a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The materials may be in solution, suspension (for example, incorporated into microparticles, liposomes, or cells). Suitable carriers and their formulations are described in Remington: The Science and Practice of Pharmacy (22nd ed.) eds. Loyd V. Allen, Jr., et al., Pharmaceutical Press, 2012. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of vaccines to humans, including solutions such as sterile water, saline, and buffered solutions at physiological pH. Pharmaceutical compositions may include carriers, thickeners, diluents, buffers, preservatives, surface active agents and the like in addition to the vaccine. Pharmaceutical compositions may also include one or more active ingredients such as antimicrobial agents, anti-inflammatory agents, anesthetics, and the like.

The disclosed vaccines are preferably formulated for delivery via intranasal, intramuscular, subcutaneous, transdermal or sublingual administration.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Combinations

The disclosed vaccine can be used to supplement existing human vaccines to improve cross protection. Therefore, the disclosed vaccine can further include (or be administered in combination with) a whole inactivated virus, split viral vaccine, live attenuated influenza vaccine, or an influenza virus-like particle (VLP) vaccine. For example, the disclosed vaccine can be combined with a trivalent inactivated vaccine (TIV) (e.g., containing killed A/H1N1, A/H3N2, and B), trivalent live attenuated influenza vaccine, trivalent split vaccine, trivalent subunit influenza vaccine, trivalent recombinant protein vaccine, or trivalent VLP vaccine. The disclosed vaccine can be combined with a bivalent inactivated vaccine, bivalent live attenuated influenza vaccine, bivalent split vaccine, or bivalent subunit influenza vaccine, bivalent recombinant protein vaccine, or bivalent VLP vaccine. The disclosed vaccine can be combined with a monovalent inactivated vaccine, monovalent live attenuated influenza vaccine, monovalent split vaccine, or monovalent subunit influenza vaccine, monovalent recombinant protein vaccine, or monovalent VLP vaccine. The disclosed vaccine can be combined with a monovalent, bivalent, or trivalent vaccine directed against Influenza A. The disclosed vaccine can be combined with a monovalent, bivalent, or trivalent vaccine directed against Influenza B. The disclosed vaccine can be combined with a monovalent, bivalent, or trivalent vaccine directed against a combination of Influenza A and Influenza B.

The disclosed vaccine can include a PNP that incorporates sequences from a particular influenza, such as Influenza A or Influenza B. The disclosed vaccine can include a PNP that incorporates sequences from a particular strain of influenza. The disclosed vaccine can include a PNP that incorporates sequences from a subtype of influenza A. The disclosed vaccine can include a PNP that incorporates sequences from a subtype of influenza A HA, such as H1 HA, H3 HA, H5 HA, and others.

In one embodiment, the vaccine includes a single PNP that incorporates sequences from a particular influenza, such as Influenza A or Influenza B. The disclosed vaccine can include a single PNP that incorporates sequences from a particular strain of influenza. The disclosed vaccine can include a single PNP that incorporates sequences from a subtype of influenza A. The disclosed vaccine can include a single PNP that incorporates sequences from a subtype of influenza A HA, such as H1 HA, H3 HA, H5 HA, and others.

In one embodiment, the vaccine includes two PNP each of which incorporates sequences from particular influenzas, such as Influenza A or Influenza B. The disclosed vaccine can include two PNP each of which incorporates sequences from a particular strain of influenza. The disclosed vaccine can include two PNP each of which incorporates sequences from a subtype of influenza A. The disclosed vaccine can include two PNP each of which incorporates sequences from a subtype of influenza A HA, such as H1 HA, H3 HA, H5 HA, and others.

In one embodiment, the vaccine includes three or more PNP each of which incorporates sequences from particular influenzas, such as Influenza A or Influenza B. The disclosed vaccine can include three or more PNP each of which incorporates sequences from a particular strain of influenza. The disclosed vaccine can include three or more PNP each of which incorporates sequences from a subtype of influenza A. The disclosed vaccine can include three or more PNP each of which incorporates sequences from a subtype of influenza A HA, such as H1 HA, H3 HA, H5 HA, and others.

The disclosed vaccine can further include (or be administered in combination with) one or more of classes of antibiotics, steroids, analgesics, anti-inflammatory agents, anti-histaminic agents, or any combination thereof. Antibiotics include Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, and Vancomycin. Suitable steroids include andranes, such as testosterone. Narcotic and non-narcotic analgesics include morphine, codeine, heroin, hydromorphone, levorphanol, meperidine, methadone, oxydone, propoxyphene, fentanyl, methadone, naloxone, buprenorphine, butorphanol, nalbuphine, and pentazocine. Anti-inflammatory agents include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isofluprednone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium. Anti-histaminic agents include ethanolamines (e.g., diphenhydrmine carbinoxamine), Ethylenediamine (e.g., tripelennamine pyrilamine), Alkylamine (e.g., chlorpheniramine, dexchlorpheniramine, brompheniramine, triprolidine), other anti-histamines like astemizole, loratadine, fexofenadine, bropheniramine, clemastine, acetaminophen, pseudoephedrine, triprolidine).

Methods of Vaccinating a Subject

A method of vaccinating a subject for influenza is disclosed that involves administering the disclosed cross-protective influenza vaccine to a subject in need thereof. The disclosed vaccine may be administered in a number of ways. For example, the disclosed vaccine can be administered intramuscularly, intranasally, or by microneedle in the skin. The compositions may be administered orally, intravenously, subcutaneously, transdermally (e.g., by microneedle), intraperitoneally, ophthalmically, vaginally, rectally, sublingually, or by inhalation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical dosage of the disclosed vaccine used alone might range from about 1 µg/kg to up to 100 mg/kg of body weight or more per vaccination, such as 10 µg/kg to 50 mg/kg, or 50 µg/kg to 10 mg/kg, depending on the factors mentioned above. In addition to dosing by the ratio of mass-of-vaccine to mass-of-patient, standardized vaccine doses for demarcated demographics can also be used. A typical dose for an adult patient may be 1 µg to 1000 µg, or 10 µg to 150 µg, or 15 µg to 135 µg per subject. A typical dose for a child patient may be 1 µg to 1000 µg, or 10 µg to 150 µg, or 15 µg to 135 µg per subject. A typical dose for an elderly patient may be 1 µg to 1000 µg, or 10 µg to 150 µg, or 15 µg to 135 µg per subject.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Results

Design and Construction of Four Tandem Copies of M2e Linked to Tetramerization Motif GCN4

Tetrameric four tandem copies of M2e construct was stabilized by introducing a foreign tetramerization motif GCN4 at C-terminal end (4M2e-GCN4), a modified version of leucine zipper domain of a yeast transcription factor (De Filette M, et al. The Journal of biological chemistry 2008; 283(17): 11382-11387; Harbury P B, et al. Science 1993; 262(5138): 1401-1407) (FIG. 1A). A signal peptide encoding sequence from the honeybee melittin protein was added at N-terminal to facilitate protein expression in insect cells Spodoptera frugiperda Sf9 (Sf9, ATCC, CRL-1711) (Wang B Z, et al. Journal of virology 2007; 81(20): 10869-10878). Hexa-Histidine tag were added following GCN4 motif sequence. In four types of full length M2e, two site-mutations C175 and C195 were made, the order of modified M2e sequences from N- to C-terminal in 4M2e-GCN4 construct were: human consensus M2e, swine consensus M2e, avian consensus M2e, domestic fowl consensus M2e (Table 1). The consensus M2e sequences were made based on 11732 human, 5920 swine, 6267 avian and 3270 domestic fowl M2 sequences deposited in the National Center for Biotechnology Information (NCBI) databank, and the software molecular evolutionary genetics analysis version 6.0 (MEGA6) was used to align and analyze sequences (Tamura K, et al. Molecular biology and evolution 2013; 30(12): 2725-2729).

Design and Construction of Head-Removed HA Constructs

Conserved stalk region of HA offers a promising target to develop cross-protective influenza A vaccines (Yassine H M, et al. Nature medicine 2015; 21(9): 1065-1070; Impagliazzo A, et al. Science 2015; 349(6254): 1301-1306). It was previously reported that HA stalk domain is more conserved compared to the highly variable globular head domain (Mallajosyula V V, et al. Proc Natl Acad Sci USA 2014; 111(25): E2514-2523; Ellebedy A H, et al. Frontiers in immunology 2012; 3: 53). The goal is to design stable and soluble trimerized head-removed H1 (hrH1) and head-removed H3 (hrH3) proteins with part of receptor-binding polypeptide chain (termed HA1) at stalk region and ectodomain of membrane anchoring polypeptide chain of HA (termed HA2) (FIG. 1B, 1C; sequences in FIGS. 11A, 11B). Previous research demonstrated the metastable HA2 conformation in viral HA and also showed that the trimer HA2 polypeptide when expressed independently from HA1 subunit, adopted the low-pH conformation spontaneously (Chen J, et al. Proc Natl Acad Sci USA 1995; 92(26): 12205-12209). The influenza A subviral particles lacking the entire HA1 subunit of HA showed limited protection in mice model (Graves P N, et al. Virology 1983; 126(1): 106-116). To generate one hrHA representative from each phylogenetic group of influenza A virus will be essential to formulate a vaccine that can elicit the real universal response. Starting with the HA sequences of H1N1 A/Puerto Rico/8/1934 and H3N2 A/Aichi/2/1968, changes were introduced using a series of rational designs. According to previous results, trimerization motifs facilitate HA oligomerization in the absence of the HA transmembrane domain (Mallajosyula V V, et al. Proc Natl Acad Sci USA 2014; 111(25): E2514-2523; Yassine H M, et al. Nature medicine 2015; 21(9): 1065-1070; Kanekiyo M, et al. Nature 2013; 499(7456): 102-106; Stevens J, et al. Science 2006; 312(5772): 404-410). A C-terminal sequence containing G6S3 or PGS linker, tetramerization motif GCN4 and hexa-Histidine tag were added following hrH1 or hrH3 sequence for oligomerization and purification purposes. The globular head domain was removed at similar cutting off positions in three-dimensional structure as reported previously (Impagliazzo A, et al. Science 2015; 349(6254): 1301-1306). The coding sequence of the major head domain of H1 (amino acids S53-P320) and the major head domain of H3 (amino acids S61-P322) were replaced with a linker sequence encoding four glycines (G4) which is predicted to be a flexible linker and not disrupt the folding of the remainder of the molecule (Steel J, et al. mBio 2010; 1(1)). To interrupt the conformational transfer at low pH value, the residues between F61 and L89 in HA2 of H1 and the residues between F63 and T87 in HA2 of H3 were replaced with flexible non-hydrophobic G4S2 linker. The F63 and V73 hydrophobic residues in HA2 are largely responsible for stabilizing the coiled coil of the low pH structure (Bommakanti G, et al. Proc Natl Acad Sci USA 2010; 107(31): 13701-13706; Bajaj K, et al. Proc Natl Acad Sci USA 2005; 102(45): 16221-16226). In the neutral pH conformation, these residues form a part of loop B connecting helix A and helix C and are exposed in head removed HA structure. To further stabilize the hrH3 construct, a presumed intra-disulfide bond was introduced in H3 by site-mutagenesis at V325C in HA1 and S91C in HA2. Head removed HA constructs were made in the context of a H1 (representative of group 1) and a H3 (representative of group 2) HA, as the cross-reactivity of neutralizing antibodies targeting the stalk region appears to be limited to HA subtypes within the same major phylogenetic group (Wang T T, et al. PLoS pathogens 2010; 6(2): e1000796; Tan G S, et al. Journal of virology 2014; 88(23): 13580-13592; Okuno Y, et al. Journal of virology 1993; 67(5): 2552-2558; Krammer F, et al. Journal of virology 2013; 87(12): 6542-6550; Ekiert D C, et al. Science 2009; 324(5924): 246-251; Kashyap A K, et al. Proc Natl Acad Sci USA 2008; 105(16): 5986-5991; Sui J, et al. Nature structural & molecular biology 2009; 16(3): 265-273).

Characterization of Recombinant 4M2e-GCN4 and Head-Removed HA Proteins

Figure 2B:
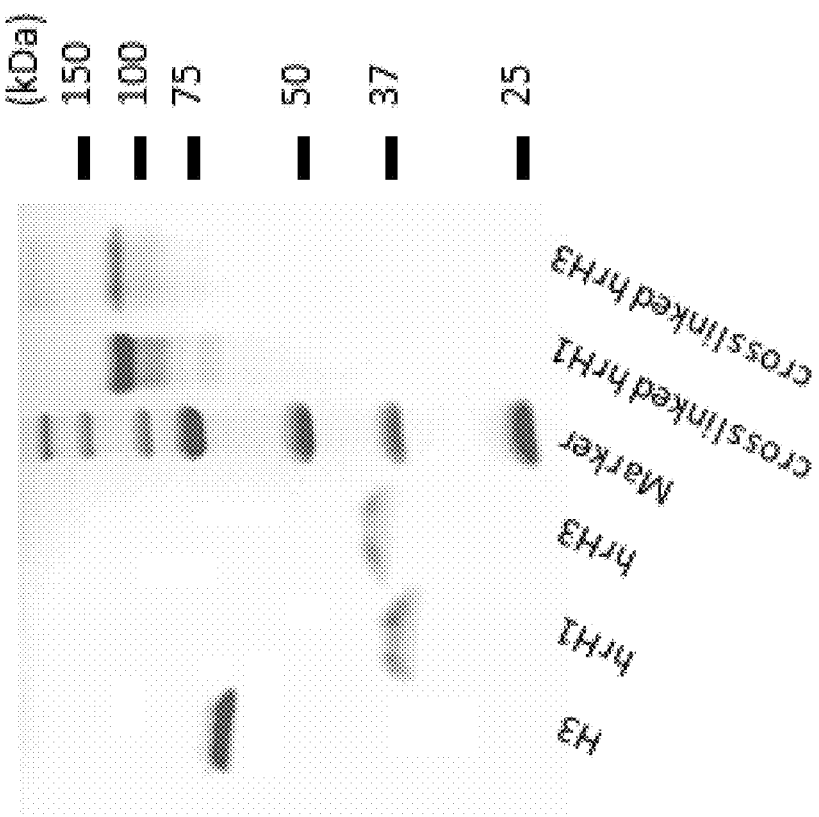
FIGS. 2A and 2B show western blot characterization of example crosslinked tetramer and monomer recombinant 4M2e-GCN4, head-removed H1 and head-removed H3.
Figure 2A:
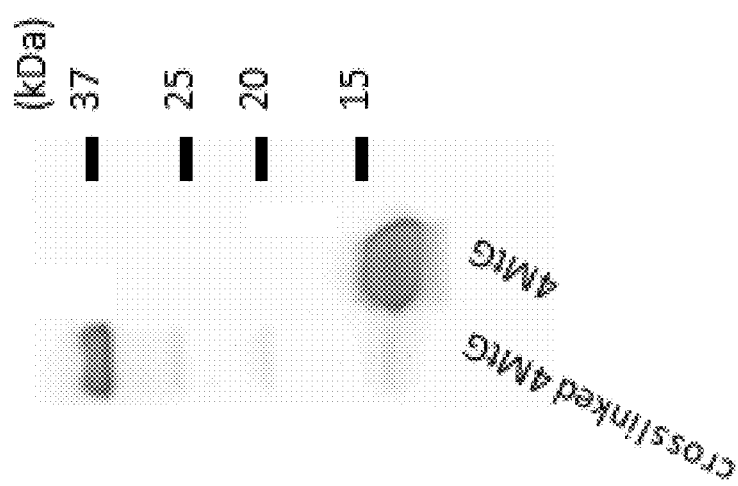
Figure 2C:
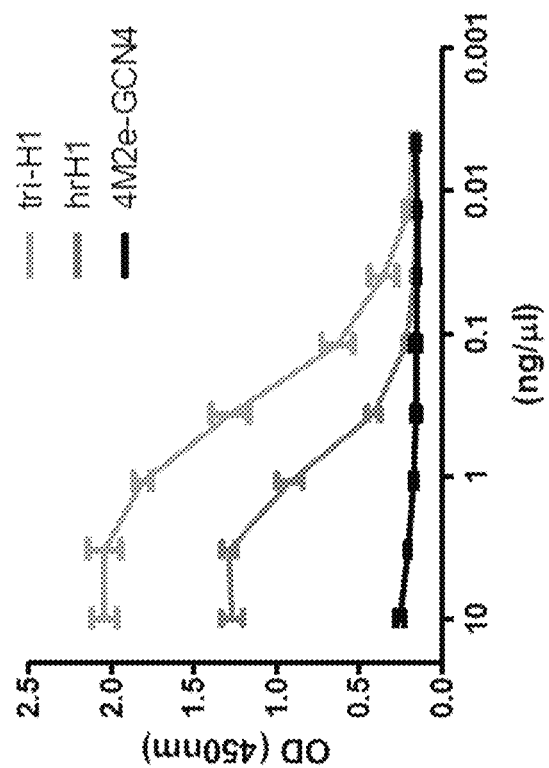
FIGS. 2C and 2D display sandwich ELISA data that indicate that the H3 and H1 hrHA proteins maintain well-preserved tertiary structural conformations compared to full-length HA proteins.
Figure 2D:
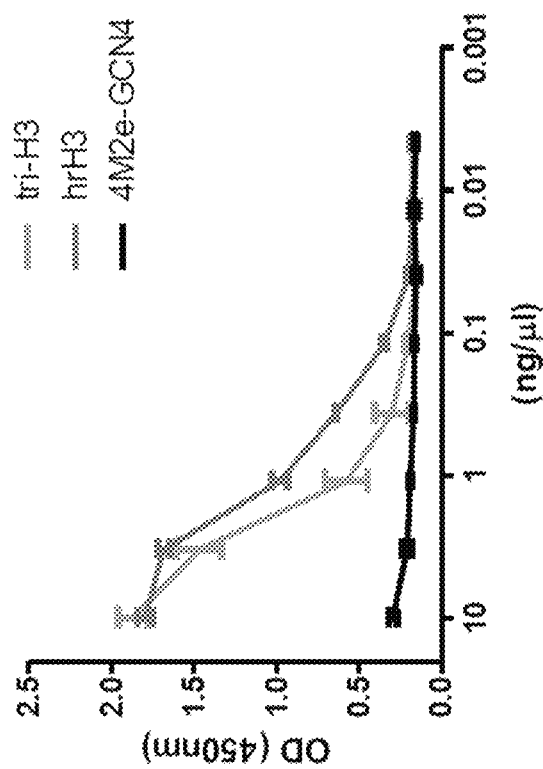

Recombinant 4M2e-GCN4 and head-removed HA proteins were expressed and purified from recombinant baculovirus protein expression system. BS3 crosslinked recombinant protein and uncrosslinked recombinant protein were run in SDS-PAGE and stained with Commassie blue. As shown in FIGS. 2A and 2B, the BS3 crosslinked 4M2e-GCN4 protein showed its tetramerization size, BS3 crosslinked hrHA protein showed its trimerization size. The antigenicity of hrH3 and hrH1 were analyzed using sandwich ELISA with monoclonal antibody 12D1 and C179, respectively. The data demonstrate that 12D1 recognizes a conformation epitope that is well presented on recombinant hrH3 protein and that the HA2 region in hrH3 is folded in a similar fashion to the corresponding region in the neutral pH structure of full length H3 protein (FIG. 2C). The data also show that recombinant hrH1 protein is recognized well by C179, as evidenced by the binding results in sandwich ELISA (FIG. 2D).

Characterization of Fabricated Protein Nanoparticles

Figure 3A:
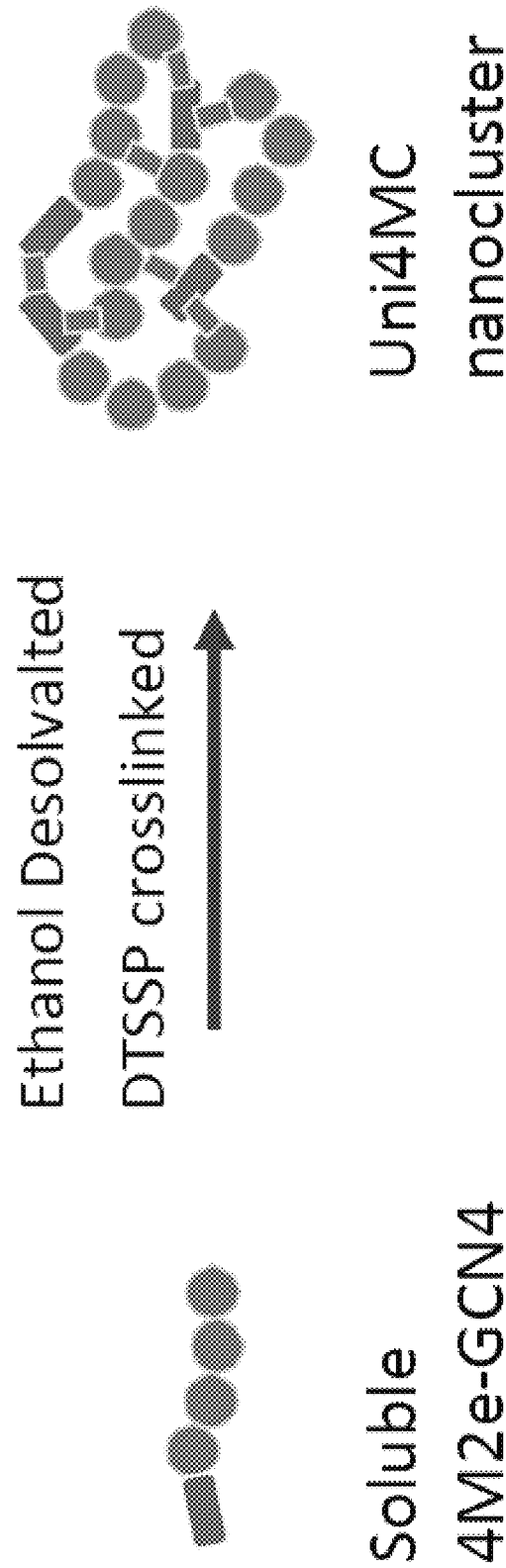
FIGS. 3A to 3E demonstrate the fabrication and characterization of PNP.
Figure 3C:
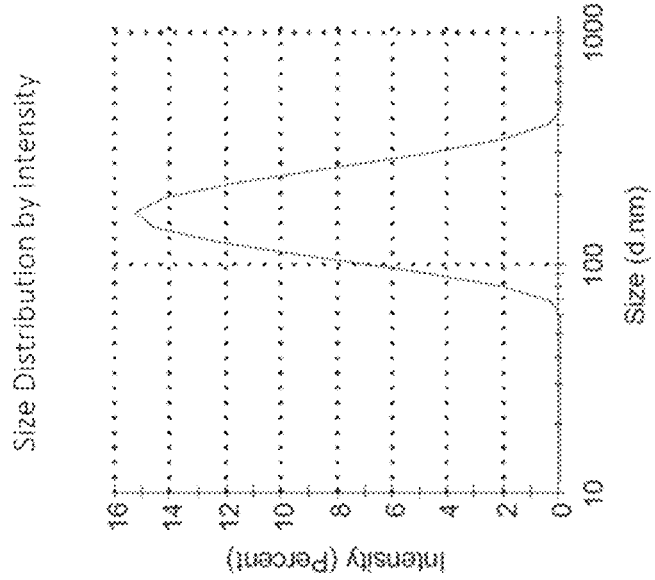
Figure 3B:
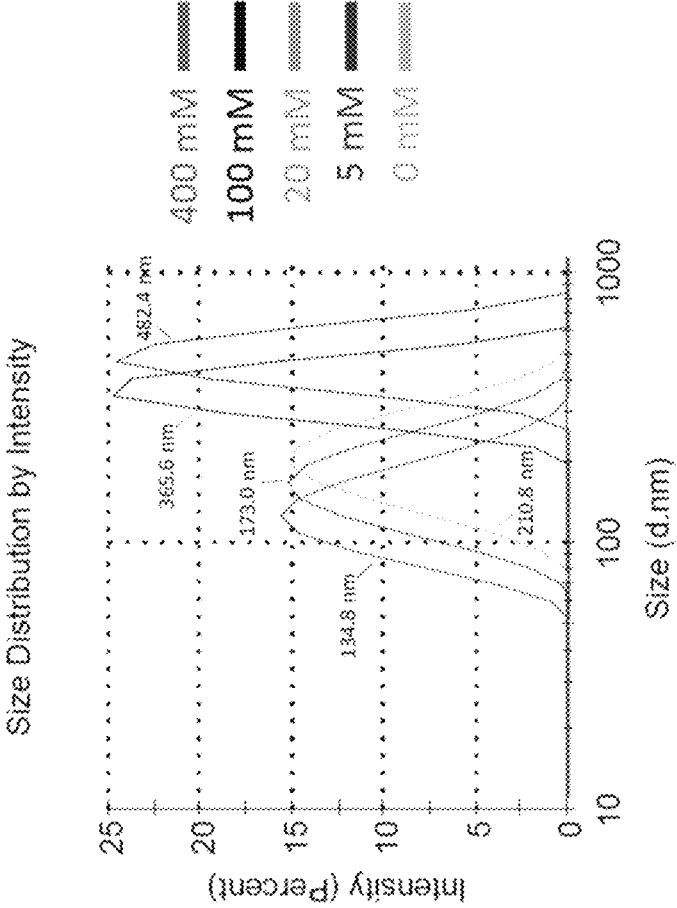
Figure 3E:
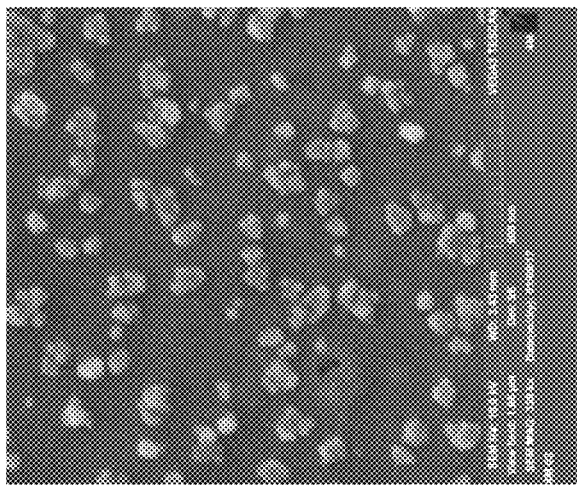
Figure 3D:
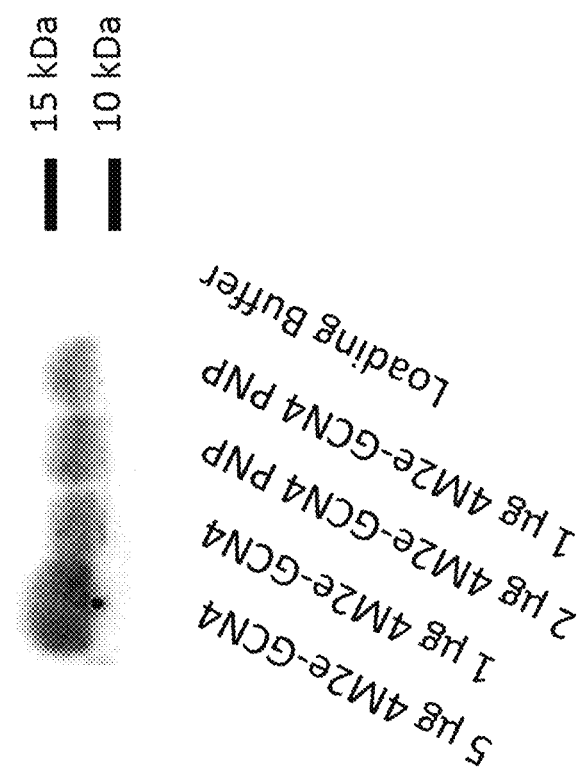

It was previously reported that protein nanoparticle vaccines were formed by a modified desolvation process (Wang L, et al. Nanomedicine: nanotechnology, biology, and medicine 2017; 13(1): 253-262; Wang L, et al. Nanomedicine: nanotechnology, biology, and medicine 2014; 10(2): 473-482; Chang T Z, et al. Biomaterials science 2017; 5(2): 223-233) and stabilized by DTSSP crosslinking. This approach generated protein nanoparticles entirely composing antigens of interest, and do not include any vehicles or vectors. We recently found that desolvated H7 PNP displayed low ability in hemagglutination of chicken red blood cells and long-time contact with solvent ethanol may result in partial loss of intact structure, however the surface coating of H7 protein played the major role in immunogenicity (Wang L, et al. Nanomedicine: nanotechnology, biology, and medicine 2017; 13(1): 253-262). M2e is regarded as a flexible linear epitope which is able to induce broadly protective immune responses. It is presumed that the conformational change of M2e does not dramatically alter its immunogenicity. To further improve the immunogenicity of hrHA, we generated 4M2e-GCN4 core PNPs by desolvation and coated core with hrHA. FIG. 3A showed the schematic diagram of 4M2e-GCN4 core PNP fabrication process. We found the use of DTSSP to stabilize the PNP while desolvation could vary the size of PNP by different DTSSP amounts. The size of PNP become larger by increasing DTSSP amounts (FIG. 3B). Therefore, to minimize the size of PNP, the core PNP were not crosslinked until the addition of hrHA in the system. The size distribution analysis using zeta-sizer showed the fabricated Uni4MC PNP peaked at 141 nm (FIG. 3C). The soluble 4M2e-GCN4 and Uni4MC PNP were analyzed in Western Blot using mouse anti-M2e antiserum. The PNP can be completely denatured into monomer and all samples can be blotted (FIG. 3D). Scanning electron microscopy (SEM) of dehydrated nanoparticles showed that particulates were relatively spherical (FIG. 3E).

Figure 4A:
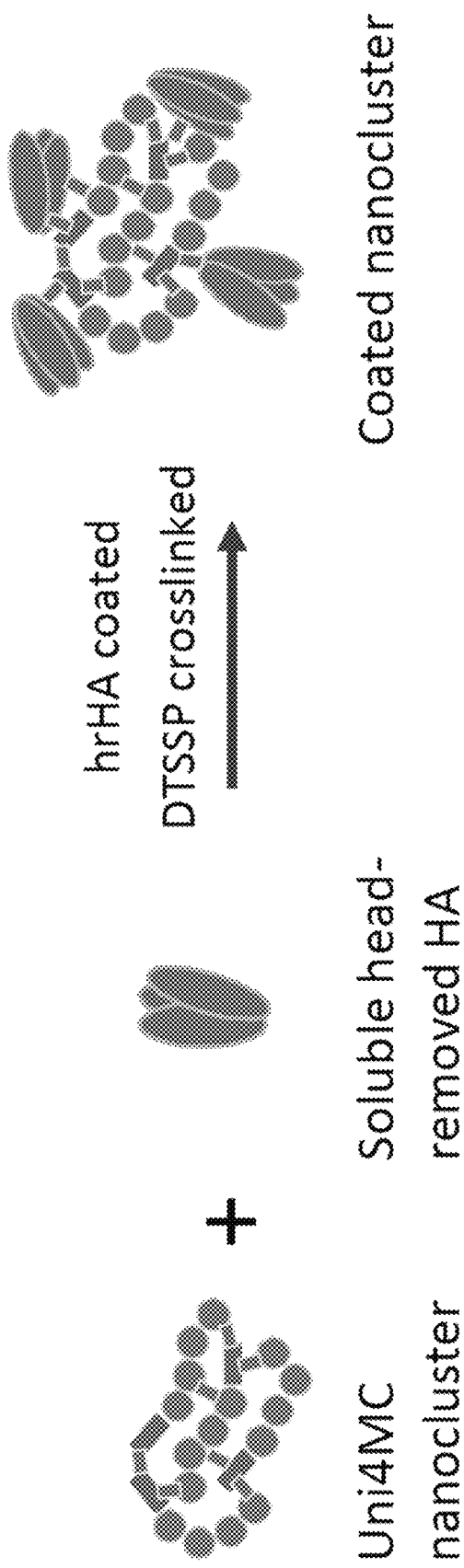
Figure 5B:
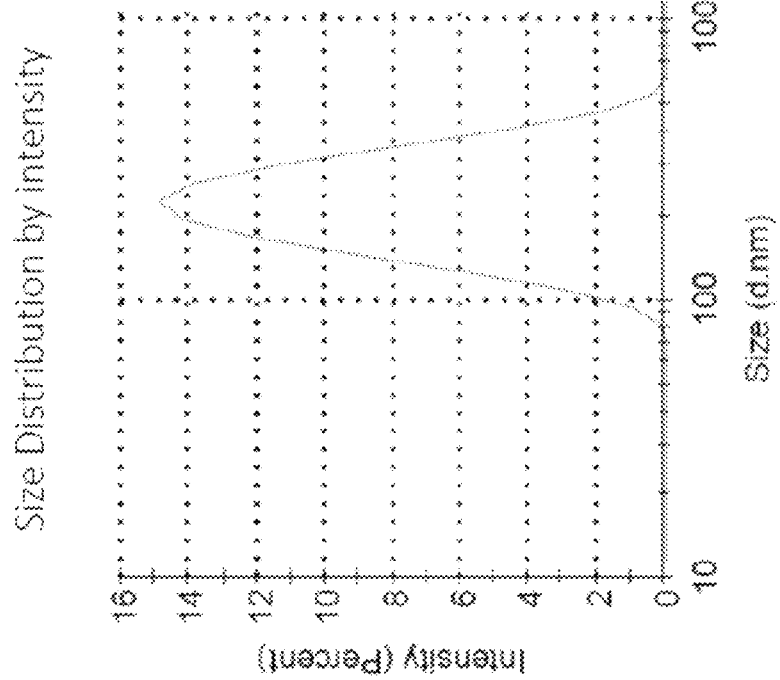
Figure 5A:
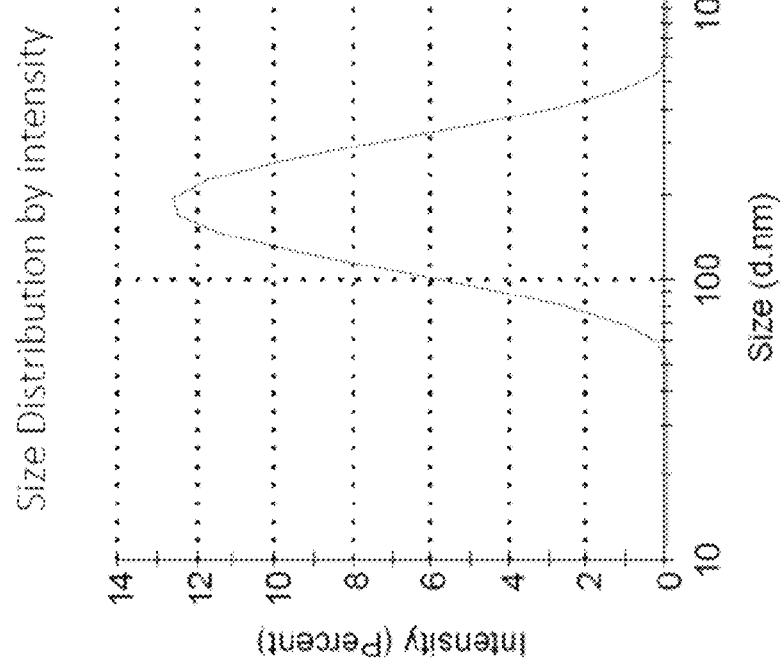
Figure 5C:
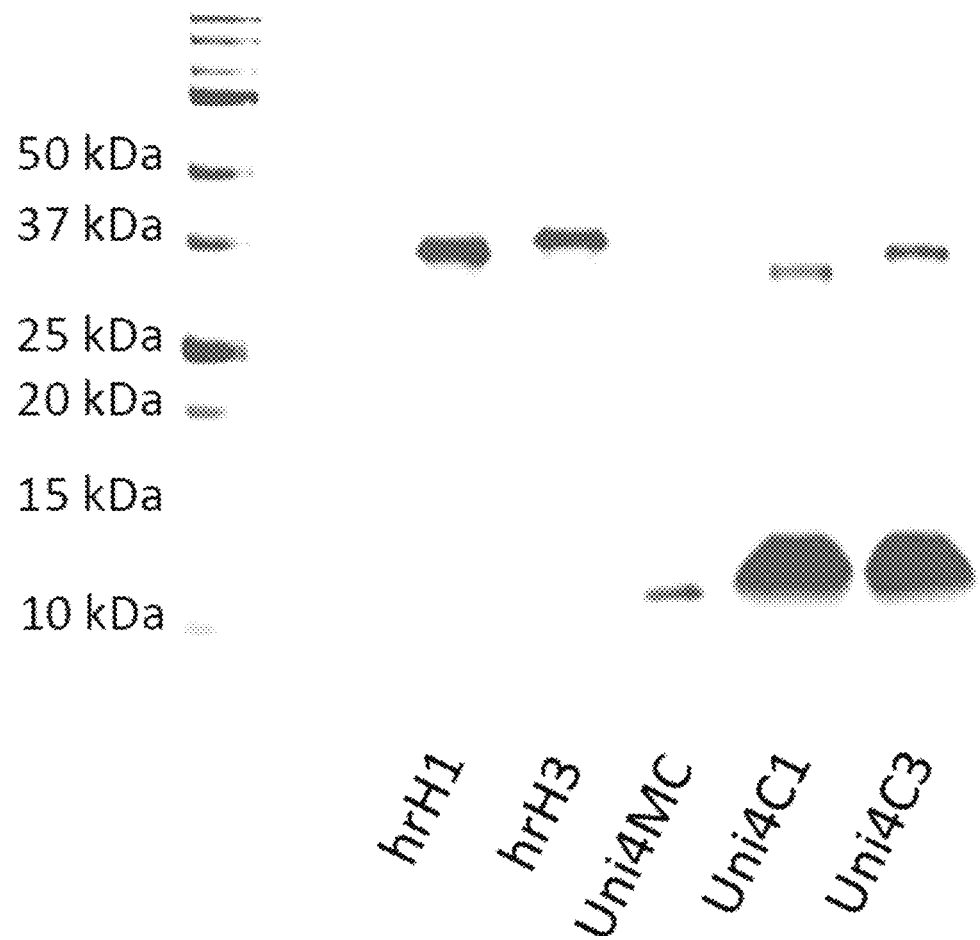

The coating process is showed in schematic diagram in FIG. 4A. As the binding is mainly mediated via hydrophobic residues interaction. The hydrophobic residues in hrH1 and hrH3 proteins were showed in red (FIG. 4B). The DTSSP crosslinker reacted mainly with primary amine in protein, the Lys residues with outwards primary amine group in hrH1 and hrH3 were labelled as spherical molecule in red (FIG. 4C). The analysis showed the theoretical feasibility in hrHA protein coating and stabilization by DTSSP crosslinking. Dynamic light scattering analysis indicated the presence of a single, reproducible population distribution with an average hydrodynamic diameter of 181 nm of hrH1 and 211 nm of hrH3 (FIGS. 5A and 5B). The Commassie blue staining showed that the Uni4MC core PNPs were successfully coated with hrH1 or hrH3 (FIG. 5C). The protein band intensity analysis of Uni4C1 and Uni4C3 using GelQuant software showed the content percentages of hrH1 and hrH3 are 11.5% and 14%, respectively. SEM analysis showed that coated nanoparticles have relative spherical shape with irregular rough surface (FIG. 5D).

Robust Seroconversion of Immunized Mice

Figure 6A:
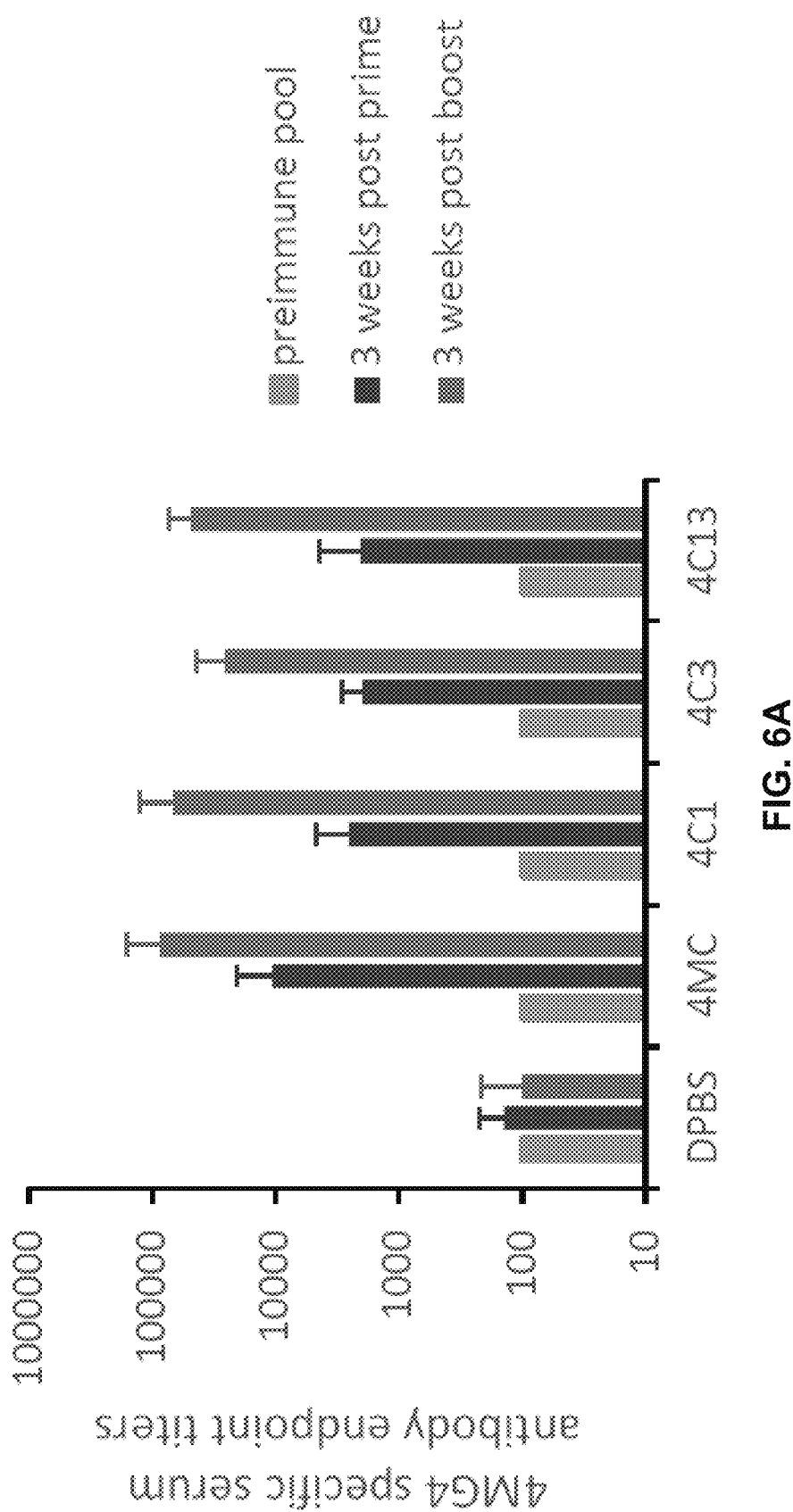
FIGS. 6A to 6G show humoral immune responses of mice immunized with PNPs as measured by serum antibody endpoint titers against the delineated target antigens.
Figure 6B:
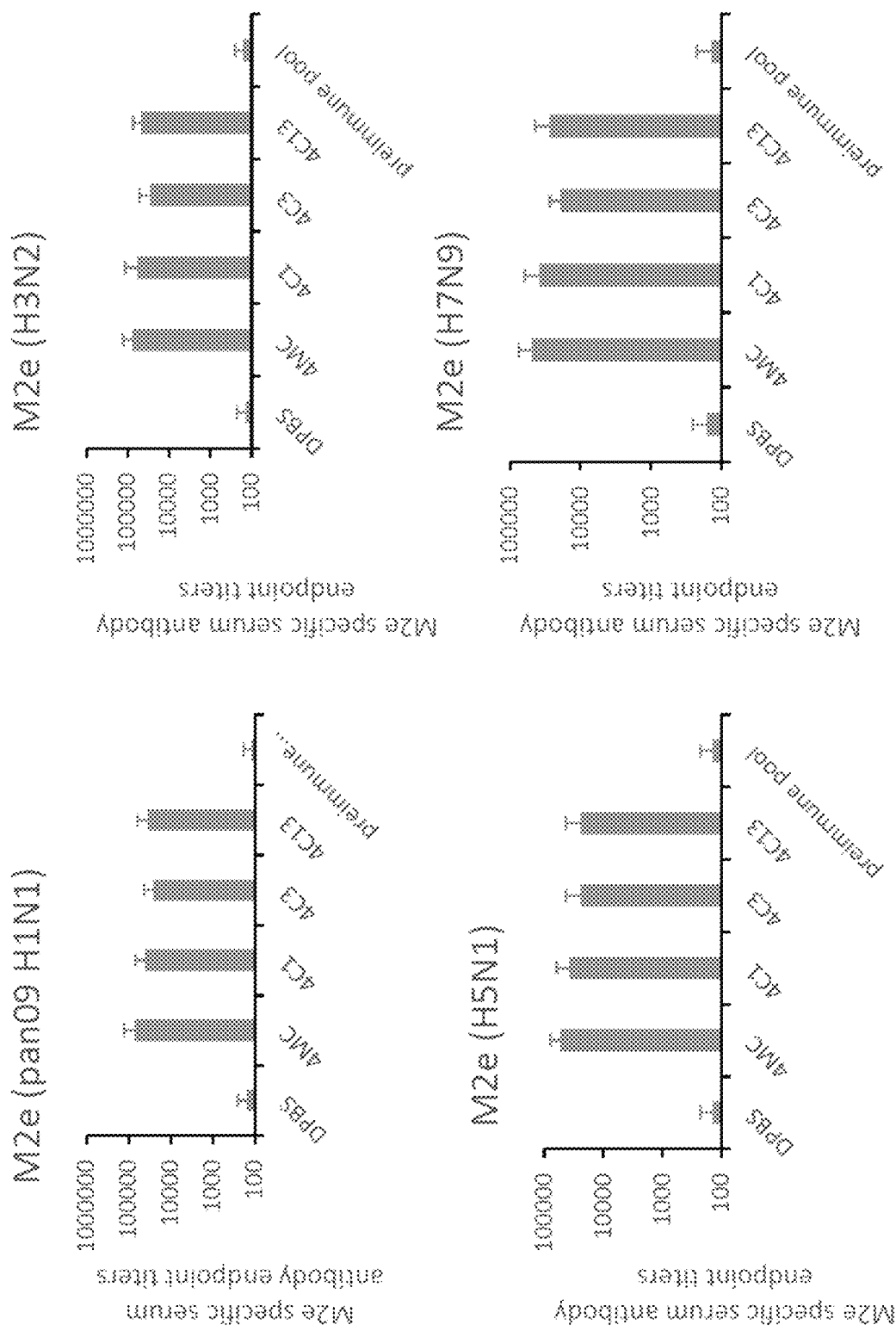
Figure 6C:
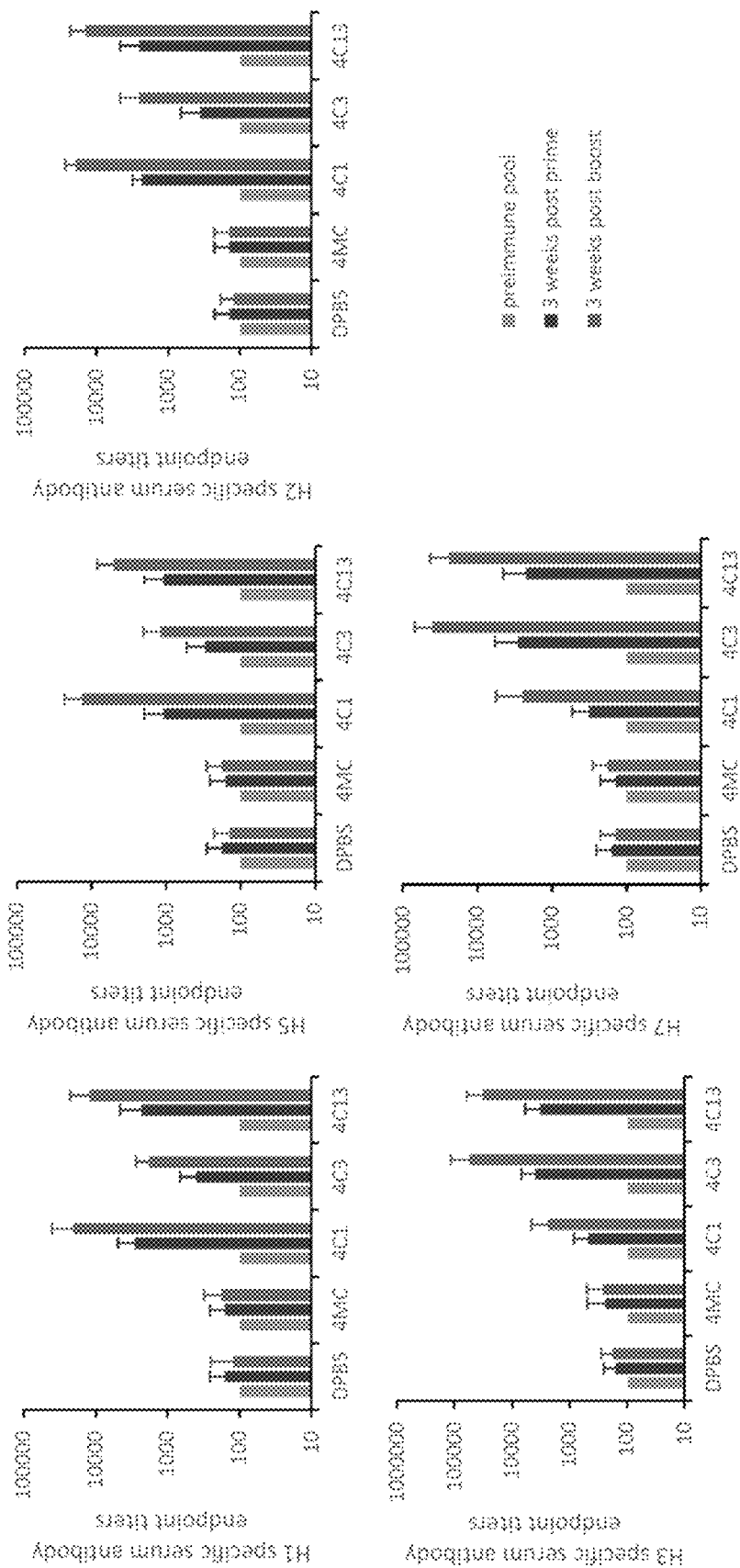
Figure 6D:
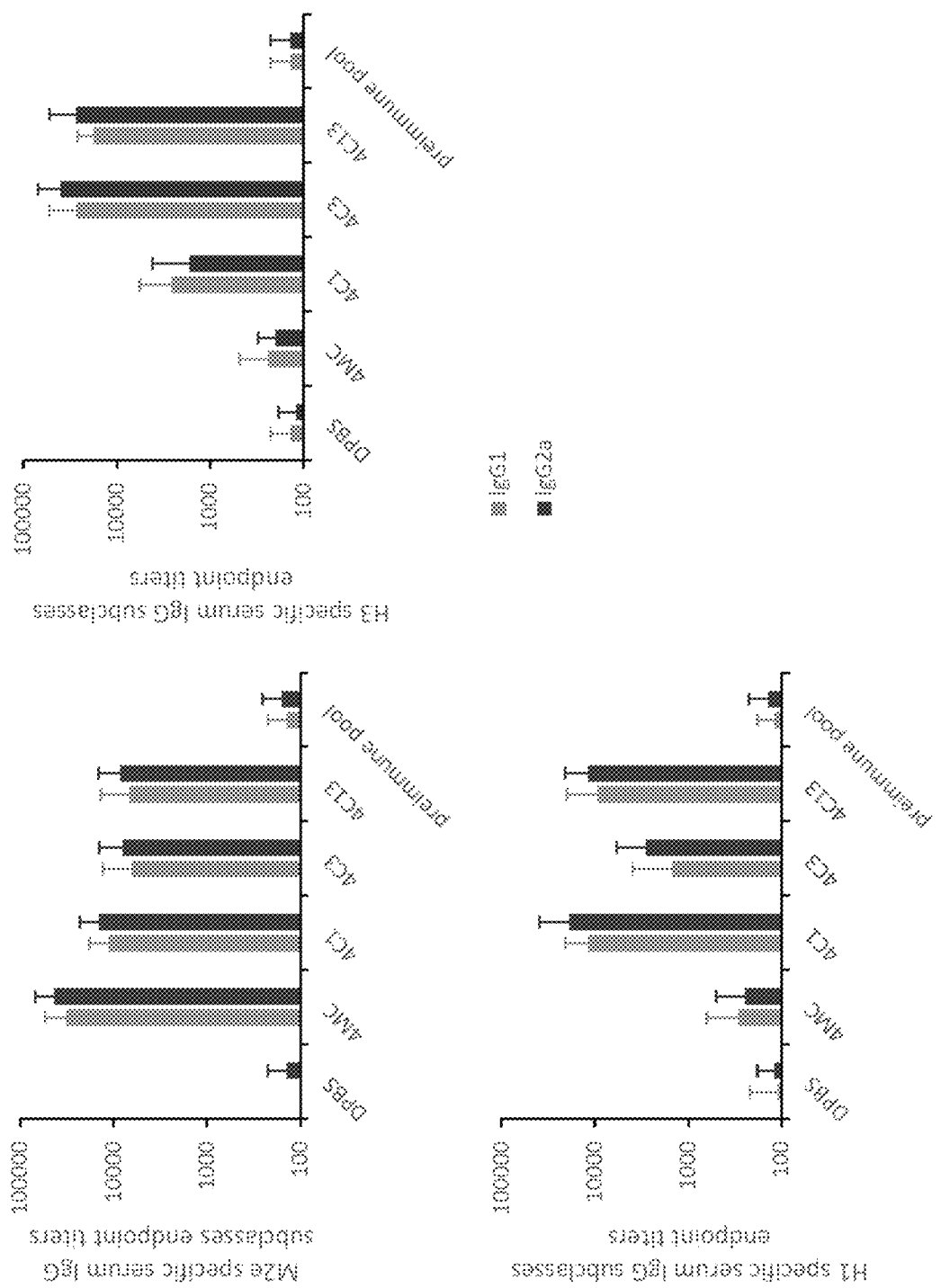
Figure 6E:
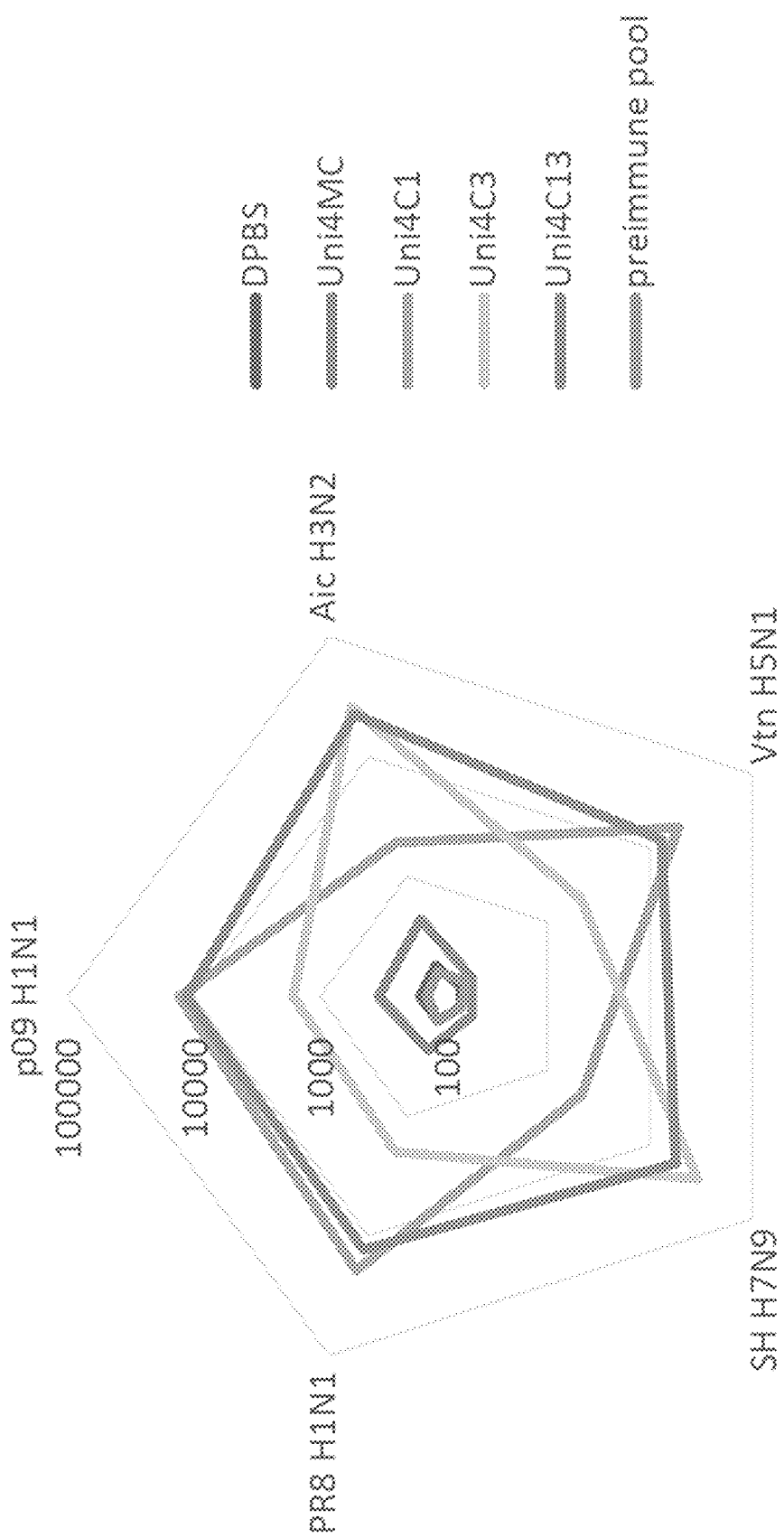
Figure 6F:
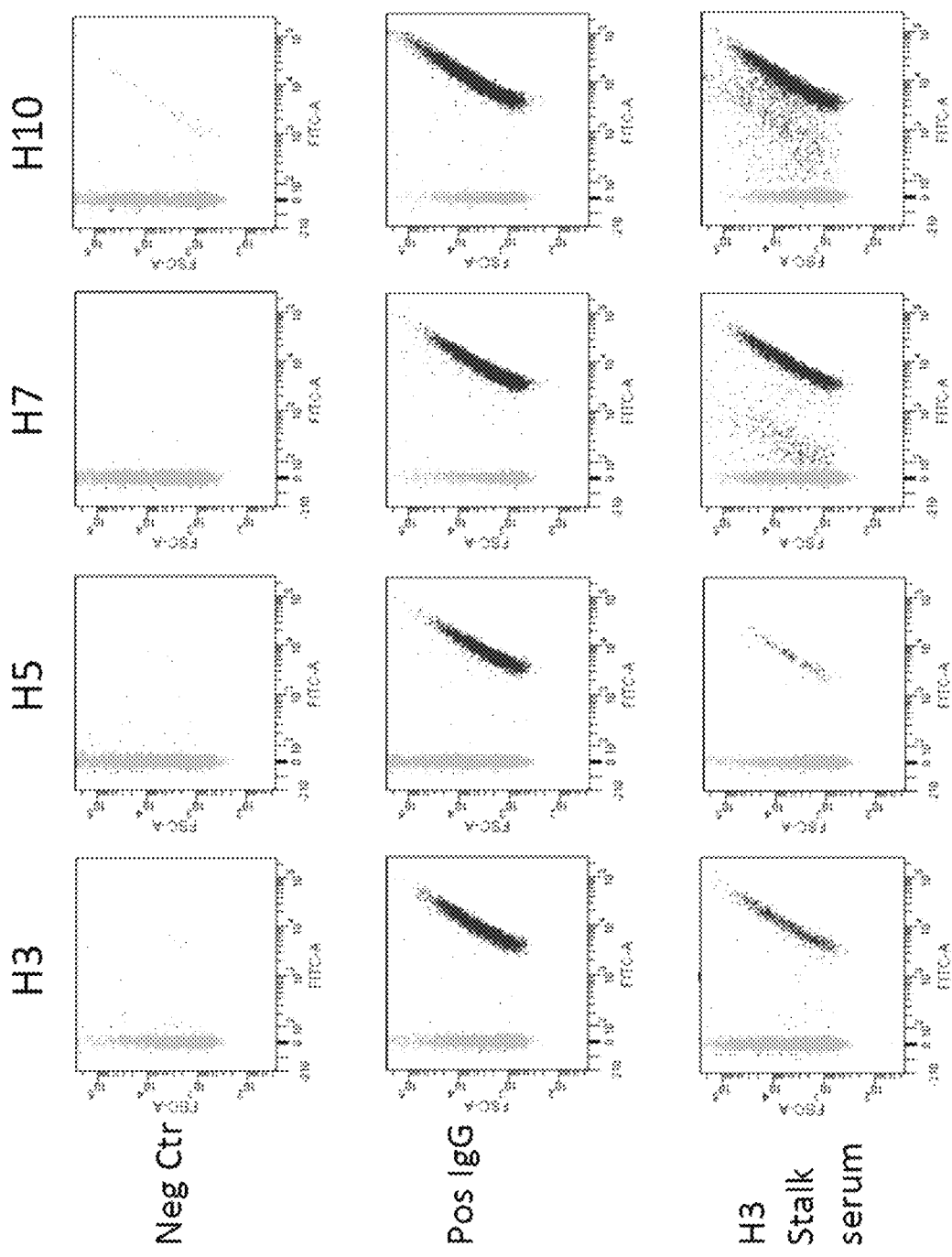
Figure 6G:
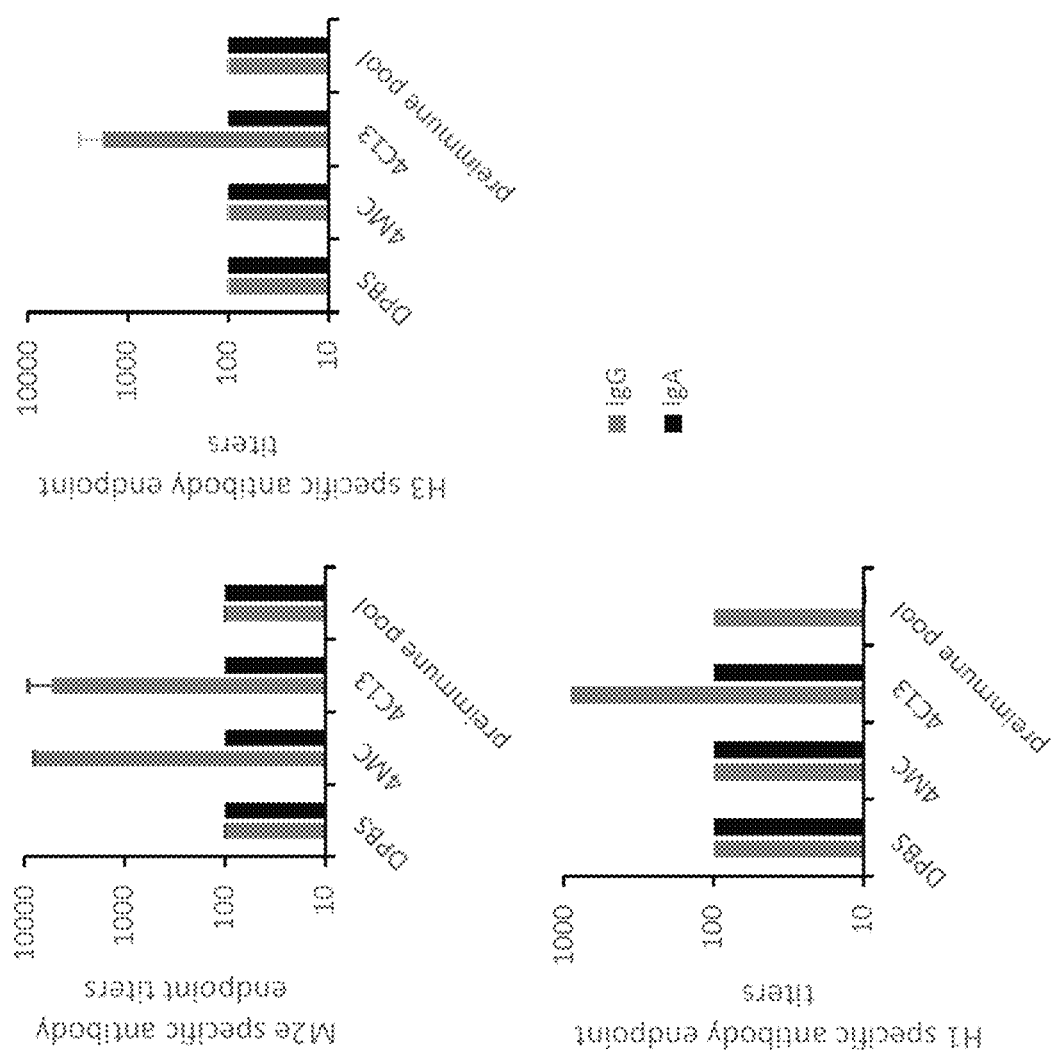

Except mock immunized group, all other immunized mice have strong seroconversion against 4M2e-GCN4 protein (FIG. 6A). The induced M2e antibodies have strong cross-reactivity to the diverse M2e peptides (FIG. 6B). Both Uni4C1 and Uni4C3 vaccines induced serum strongly bind to the HA from same phylogenetic group, and have weaker binding activity to the heterologous H3 and H1 respectively (FIG. 6C). The boosting immunization significantly enhanced the specific antibody titers (FIGS. 6A and 6C). The PNP vaccines induced a balanced Th1/Th2 responses, as evidenced by the similar levels of induced serum IgG1 and IgG2a titers (FIG. 6D). As shown in the radar diagram of inactivated influenza A virus coated ELISA results, Uni4C13 induced serum has broad binding activity to all subtypes of viruses, whereas the Uni4C1-induced and Uni4C3-induced antiserum have strong binding activity to phylogenetic group 1 and group 2 HA, respectively (FIG. 6E). The antiserum staining of HA transfected MDCK cells also showed that H3 stalk antiserum can bind to various subtypes of membrane anchored HA proteins, including H3, H7 and H10 but not H5 (FIG. 6F). Antibodies in sera that reacted specifically with M2e, H1 HA, and H3 HA were predominated by IgG over IgA (FIG. 6G).

Immunization and Challenge Study in Mice

Figure 7A:
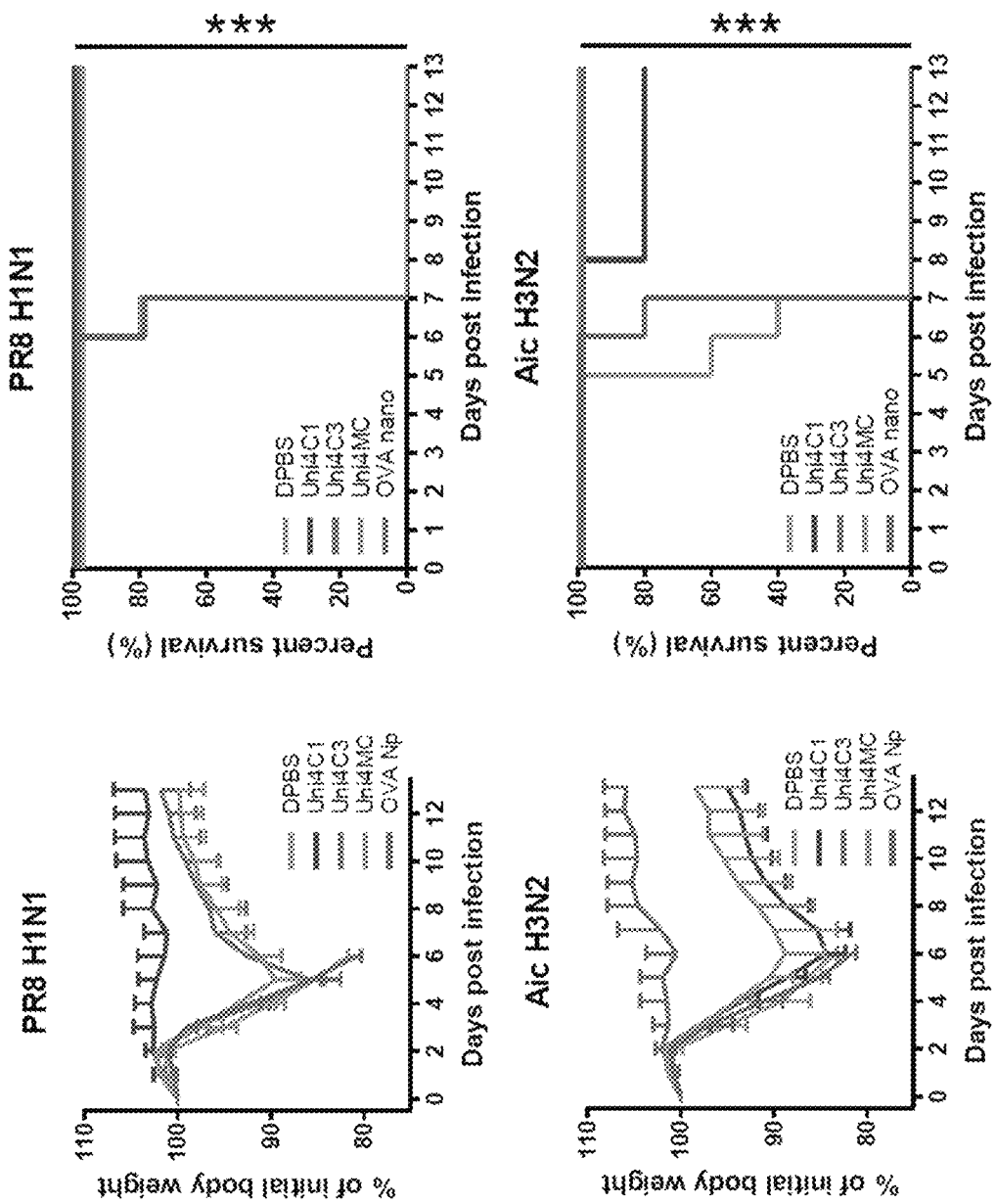
FIG. 7 shows immune protection conferred against lethal homologous and heterologous influenza virus challenge as demonstrated by maintenance of body weight and survival after challenge.
Figure 10:
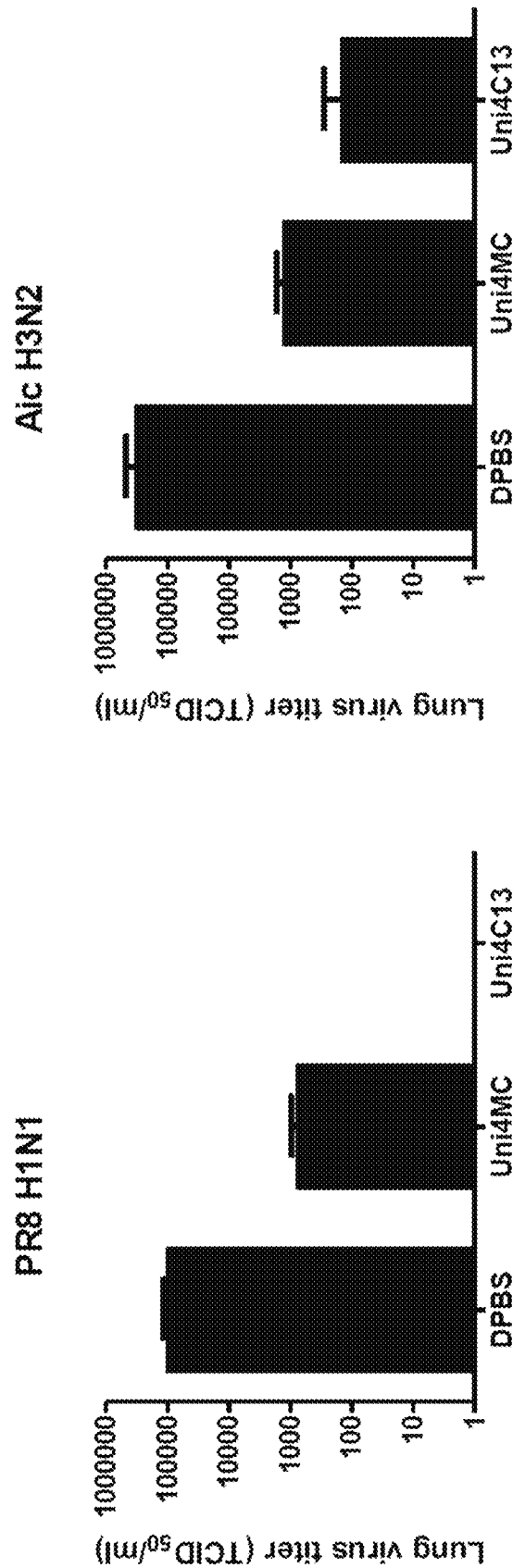
FIG. 10 shows virus titers in the lung 5 days after 1×mLD50 viral challenge.
Figure 11A:
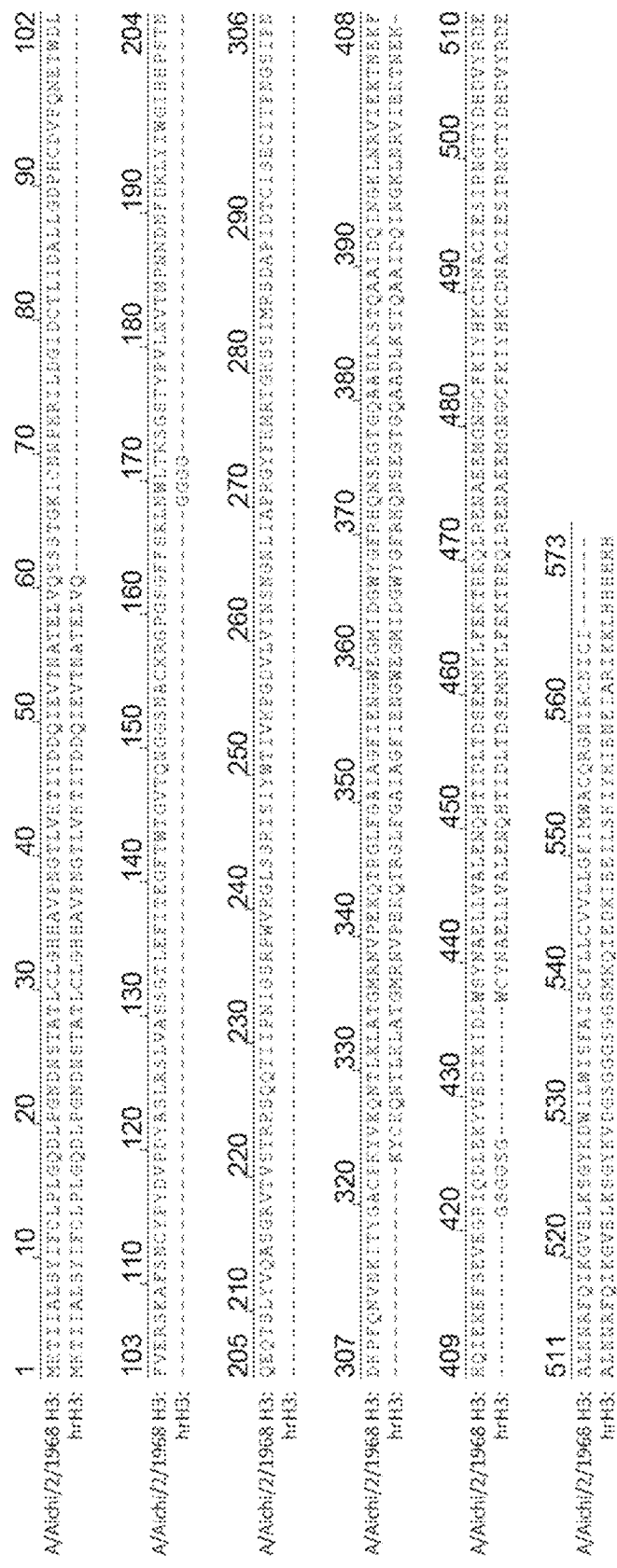
FIG. 11A shows sequence alignment of hrH3 (SEQ ID NO:41) with A/Aichi/2/1968 H3 (SEQ ID NO:42).

Six- to eight-week old female BALB/c mice were intramuscularly immunized for two times at 4-week interval in hind legs with 10.5 μg Uni4MC, 12 μg Uni4C1, 12 μg Uni4C3 or 12 μg Uni4C13. Four weeks after boosting immunization, mice were challenged intranasally with 5× mouse lethal dose 50 (mLD50) of mouse adapted (m.a.) influenza A viruses, PR8 H1N1, p09 H1N1, Aic H3N2, Phi H3N2, rVn H5N1 and rSH H7N9, respectively. Uni4C1 and Uni4C3 immunized mice were fully protected against influenza A viruses expressing HA from the same phylogenetic group as demonstrated by both weight retention and survival in the vaccinated conditions (FIG. 7A). Uni4C13 immunization conferred complete protection against lethal dose of heterologous influenza A virus challenge. Weight loss monitoring records showed that Uni4C13 immunized mice still experienced slightly weight loss after lethal dose of rVn H5N1 and rSH H7N9 challenge. All mock immunized mice died after lethal dose infection. Those mice received Uni4MC immunization were fully protected from lethal dose challenge with PR8 H1N1, p09 H1N1, Aic H3N2 and Phi H3N2 but partially protected from lethal dose infection with rVn H5N1 and rSH H7N9. Histological analysis showed that after sublethal dose infection, the lung immune cell infiltration from well protected Uni4C13 and Uni4MC groups of mice is much less than DPBS mock immunized mice (FIG. 8). The lung virus titers from Uni4C13 immunized mice are also significantly lower than the other groups. Uni4MC immunization also reduced lung viral load faster than DPBS group (FIG. 10).

In order to investigate the mechanism of protection conferred by PNPs, HAI assays were performed (FIG. 9). It was found that no HAI activities of induced serum were detected. The convalescent serum samples collected from mice challenged with diverse influenza A viruses were used as positive controls. This implies that other antibody mediated mechanism(s) such as neutralizing antibodies, antibody-dependent cellular cytotoxicity (ADCC) or complement dependent cellular cytotoxicity may contribute to the protection.

Materials and Methods

Ethics Statement

This study was carried out in strict accordance with the recommendations in the Guide for the Care and Use of Laboratory Animals of the National Institutes of Health. All mouse studies were approved by Georgia State University Institutional Animal Care and Use Committee (IACUC) under protocol number 2003060. Female BALB/c mice and female C57BL/6 mice (six to eight-week old) were purchased from the Jackson Laboratory and housed in the animal facility at Georgia State University. Bleeding, infecting and sampling were performed under anesthesia that was induced by inhalation of isoflurane to reduce mouse suffering.

Expression and Purification of Recombinant Proteins

Recombinant baculovirus expressing 4M2e-GCN4, hrH1 or hrH3 was generated using the Bac-to-Bac protein expression kit (Invitrogen, Grand Island, N.Y.) according to the manufacturer's instructions and soluble 4M2e-GCN4, hrH1 and hrH3 recombinant proteins were purified from the sf9 insect cell protein expression system as previously described (Weldon W C, et al. PloS one 2010 5(9)).

Bis [Sulfosuccinimidyl] (BS3) Crosslinking

The oligomeric status of purified 4M2e-GCN4, hrH1 and hrH3 proteins were determined using the soluble Bis [sulfosuccinimidyl] (BS3) crosslinker (Pierce-Rockford, Ill.) in a crosslinking reaction to fix the polymeric structures of proteins following with sodium dodecyl sulfate polyacrylamide gel electrophoresis (SDS-PAGE), as described previously (Weldon W C, et al. PloS one 2010 5(9)).

Protein Nanoparticles Fabrication

Protein nanoparticles (PNP) were made as previously described with modification (Wang L, et al. Nanomedicine: nanotechnology, biology, and medicine 2017; 13(1): 253-262; Wang L, et al. Nanomedicine: nanotechnology, biology, and medicine 2014; 10(2): 473-482; Chang T Z, et al. Biomaterials science 2017; 5(2): 223-233). To make the 4M2e-GCN4 core (4MC) PNP, the 4M2e-GCN4 protein solution in DPBS (Gibco) was desolvated with a 4:1 volume ratio of absolute ethanol to protein solution, herein 4.8 ml absolute ethanol was dripped at a constant rate at 1 ml/min to 1.2 ml 3.2 mg/ml 4M2e-GCN4 protein solution under constant stirring at 600 rpm at room temperature. The water-soluble thiol-cleavable primary amine-reactive crosslinker 3,3'-dithiobis[sulfosuccinimidylpropionate] (DTSSP; Cat No. 21578, Thermo Scientific) was used to stabilize the resulting PNP. PNPs were crosslinked with DTSSP at final concentration 5 mM while stirring at room temperature for one hour, followed by centrifugation at 15,000×g for 15 min at room temperature to pellet the PNP. PNPs were resuspended by sonication in either 1 ml 2.8 mg/ml hrH1 in DPBS, 1 ml 3.1 mg/ml hrH3 in DPBS or 1 ml DPBS for coating or non-coating respectively, to generate hrH1 coated 4MC PNP (vaccine code: Uni4C1), hrH3 coated 4MtG core PNP (vaccine code: Uni4C3) and 4MC PNP (vaccine code: Uni4MC). Coating reactions were performed in 5 mM DTSSP for 2 hours while stirring at 4° C. The coat crosslinking reactions were quenched with 30 mM Tris-HCl solution at pH 7.4 for 15 min. Following collection by centrifugation at 20,000×g for 30 min at 4° C., PNPs were resuspended by sonication in 1 ml DPBS.

PNP Characterization

Nanoparticle size distribution and zeta potential were assessed by dynamic light scattering (DLS) and electrophoretic light scattering (ELS) respectively with a Malvern Zetasizer Nano ZS (Malvern Instruments, Westborough, Mass.). Protein concentration in the PNP solution was assessed with a BCA assay according to the manufacturer's instructions (Thermo Scientific, Waltham, Mass.). PNP were resuspended in water, air-dried, and sputter-coated with carbon prior to visualization with a Zeiss LEO 1450vp scanning electron microscope (Carl Zeiss, Jena, Germany) at 5.0 kV.

Immunization and Influenza a Viruses Challenge

All animal experiments were approved and performed in accordance with local legislation on animal experiments. Mice (BALB/c strain, female, 6-8 weeks old, n=5 per group) received intramuscular (i.m.) immunizations for two times at 4 week interval in hind legs with 50 µl vaccine mixture in DPBS containing 10.5 µg Uni4MC, 12 µg Uni4C1, 12 µg Uni4C3 or 12 µg Uni4C13 (formulation comprising physical mixture of 6 µg Uni4C1 and 6 µg Uni4C3 in DPBS). Blood samples were collected at 1 day prior to priming and 3 weeks after priming and boosting. Four weeks after boosting immunization, mice were challenged intranasally with 5× mouse lethal dose 50 (mLD50) of mouse adapted (m.a.) influenza A virus in 50 µl DPBS, including PR8 H1N1 (A/Puerto Rico/08/1934), p09 H1N1 (A/California/07/2009), Aic H3N2 (A/Aichi/02/2968), Phi H3N2 (A/Philippines/02/1982), rVn H5N1 (reassortant A/Vietnam/1203/2004; HA and neuraminidase (NA) were derived from A/Vietnam/1203/2004, and the remaining backbone genes from A/Puerto Rico/08/1934) or rSH H7N9 (reassortant A/Shanghai/02/2013; HA and NA were derived from A/Shanghai/02/2013, and the remaining backbone genes from A/Puerto Rico/08/1934). Body weight loss and survival rates were monitored daily for 14 days post infection (dpi). Weight loss of 20% was used as the end point at which mice were euthanized according to IACUC guidelines.

Determination of Lung Virus Titers

Three mice per immunization group were euthanized at 5th day post 1×mLD50 m.a. H1N1 A/Puerto Rico/08/1934 or m.a. H3N2 A/Aichi/02/1968 infection. Lungs were excised and homogenized in 10% (w:v) DPBS. Lung homogenates were cleared from debris by centrifugation for 10 min at 16,000×g at 4° C. Madin Darby Canine Kidney (MDCK) cells were seeded in triplicate at 2×104 cells per well in a 96-well plate and infected with 50 µl of a 1/10-dilution series of the cleared lung homogenates. After 1 hour of incubation at 37° C., wash the culture with DPBS three times, then add fresh 100 µl serum-free medium containing DMEM (Gibco), 2 mM L-glutamine (Life technologies), 10 µg/ml streptomycin, 10 U/ml penicillin (Hyclone), 0.1 mM non-essential amino acid (Gibco) and 2 µg/ml TPCK-treated trypsin (Sigma-Aldrich). After five days of incubation at 37° C., the presence of virus in the supernatant was assayed by measuring the hemagglutinating activity in the supernatant and using the method of Reed and Muench for calculation (Reed L J, et al. Am J Epidemiol 1938; 27: 493-497).

Histological Analysis

Three mice per immunization group were euthanized at 5th day post 1×mLD50 m.a. H1N1 A/Puerto Rico/8/1934 or m.a. H3N2 A/Aichi/2/1968 infection. Lung tissues were isolated and fixed with 10% neutral buffered formalin. Fixed lung tissues were embedded in paraffin and processed for Haemotoxylin and Eosin (H&E) staining. Three sections with 10 µm thickness from three different parts of the lungs were stained with H&E and examined microscopically unbiased by three pathologists. The severity of the inflammation in the examined lung sections was scored on a scale of 0 to 5 (with 0.5 interval). Scores were given as absent (0), subtle (1), mild (2), moderate (3), severe (4), and massive (5).

Hemagglutination Inhibition (HAI) Assay

Mouse sera were pretreated with three volumes of receptor-destroying enzyme (Sigma-Aldrich, U.S.) and incubated overnight at 37° C. Five volumes of filter-sterilized 1.5% sodium citrate solution was added and the mixture was inactivated at 56° C. for 30 min. 1/20 volume of 5% turkey red blood cells were added to the sera followed by incubation overnight at 4° C. to pre-clear the sera. Samples were then centrifuged for 10 min at 1,500 g, and twofold serial dilutions of the supernatant were prepared and tested for HAI activity against 8HA in 50 µl of PR8 H1N1, p09 H1N1, Aic H3N2, Phi H3N2, Vtn H5N1 or SH H7N9.

Lung Virus Titer Determination

To determine lung viral load, PR8 H1N1 or Aic H3N2 infected mice from Uni4MC, Uni4C13 and DPBS immunization groups were sacrificed at the 5th day post infection. Their lungs were isolated and homogenized in DPBS at 10% (w/v) ratio. The lung homogenates were spun at 16,000×g for 15 min to pellet tissue debris, and the supernatants were collected. Samples were stored at −80° C. until titration using TCID50 measurement method.

TABLE 1

List of M2e sequences used in study

| Present in | Codes | Sequence | SEQ ID | Origin |
|---|---|---|---|---|
| Petide | huM2e | SLLTEVETPIRNEWGCRCNDSSD | SEQ ID NO: 1 | Human consensus |
| | p09M2e | SLLTEVETPTRSEWECRCSDSSD | SEQ ID NO: 2 | A/California/07/2009 (H1N1) |
| | VtnM2e | SLLTEVETPTRNEWECRCSDSSD | SEQ ID NO: 3 | A/Vietnam/1203/2004 (H5N1) |
| | SHM2e | SLLTEVETPTRTGWECNCSGSSE | SEQ ID NO: 4 | A/Shanghai/02/2013 (H7N9) |
| Influenza A virus | PR8M2e | SLLTEVETPIRNEWGCRCNGSSD | SEQ ID NO: 5 | A/Puerto Rico/08/1934 (H1N1) |
| | AicM2e | SLLTEVETPIRNEWGCRCNDSSD | SEQ ID NO: 6 | A/Aichi/02/1968 (H3N2) |
| | p09M2e | SLLTEVETPTRSEWECRCSDSSD | SEQ ID NO: 7 | A/California/07/2009 (H1N1) |
| | PhiM2e | SLLTEVETPIRNEWGCRCNDSSD | SEQ ID NO: 8 | A/Philippines/02/1982 (H3N2) |
| | rVnM2e | SLLTEVETPIRNEWGCRCNGSSD | SEQ ID NO: 9 | A/Vietnam/1203/2004 (rgH5N1) |
| | rSHM2e | SLLTEVETPIRNEWGCRCNGSSD | SEQ ID NO: 10 | A/Shanghai/2/2013 (rgH7N9) |
| 4MtG | huM2e | SLLTEVETPIRNEWGSRSNDSSD | SEQ ID NO: 11 | Human consensus |
| | swnM2e | SLLTEVETPTRSEWESRSSDSSD | SEQ ID NO: 12 | Swine consensus |
| | aviM2e | SLLTEVETPTRNGWESKSSGSSD | SEQ ID NO: 13 | Avian consensus |
| | fwlM2e | SLLTEVETPTRNGWESNSSDSSD | SEQ ID NO: 14 | Domestic fowl consensus |

Example 2

The following is an Influenza A H3 stalk ectodomain sequence:

(SEQ ID NO: 15)
MKTIIALSYIFCLPLGQDLPGNDNSTATLCLGHHAVPNGTLVKTITDDQI

EVTNATELVQSSSTGKICNNPHRILDGIDCTLIDALLGDPHCDVFQNETW

DLFVERSKAFSNCYPYDVPDYASLRSLVASSGTLEFITEGFTWTGVTQNG

GSNACKRGPGSGFFSRLNWLTKSGSTYPVLNVTMPNNDNFDKLYIWGIHH

PSTNQEQTSLYVQASGRVTVSTRRSQQTIIPNIGSRPWVRGLSSRISIYW

TIVKPGDVLVINSNGNLIAPRGYFKMRTGKSSIMRSDAPIDTCISECITP

NGSIPNDKPFQNVNKITYGACPKYVKQNTLKLATGMRNVPEKQTRGLFGA

IAGFIENGWEGMIDGWYGFRHQNSEGTGQAADLKSTQAAIDQINGKLNRV

IEKTNEKFHQIEKEFSEVEGRIQDLEKYVEDTKIDLWSYNAELLVALENQ

HTIDLTDSEMNKLFEKTRRQLRENAEEMGNGCFKIYHKCDNACIESIRNG

TYDHDVYRDEALNNRFQIKGVELKSGYK

Figure 12:
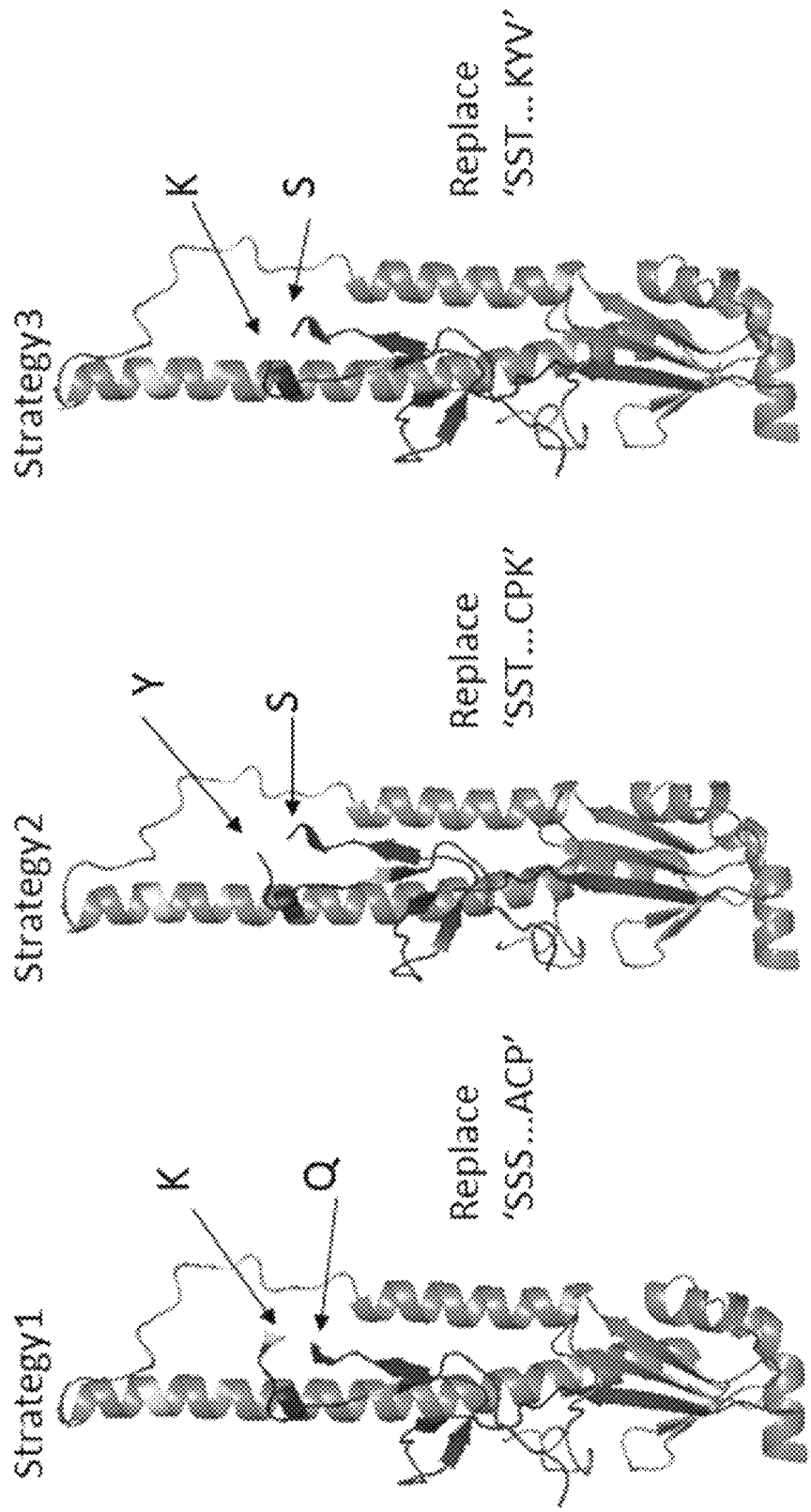
FIG. 12 shows protein structures for three different strategies of HA head-removal.
Figure 13:
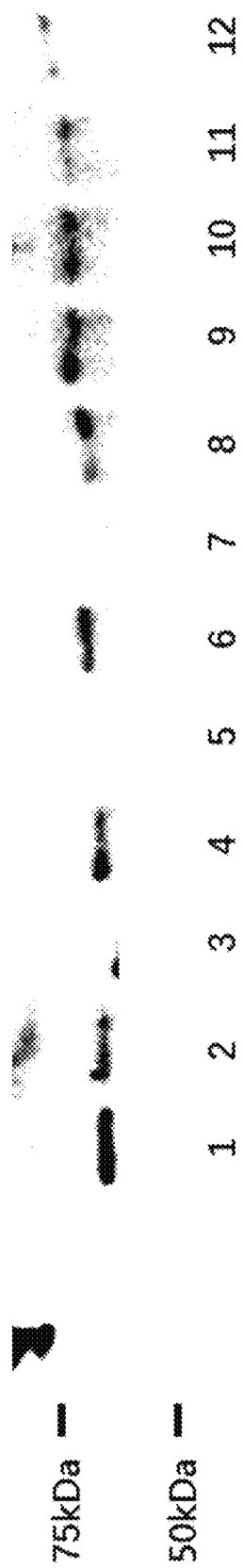
FIG. 13 shows Western blot analysis of expressed hrH3 that were constructed by different strategies. One lane of the gel was used for each strategy, as follows: (Lane 1), strategy 1 (Str1) combines with 4 Glycine linker (4G), Str1-4G; (Lane 2), Str2-4G; (Lane 3), Str3-4G; (Lane 4), Str1-3G; (Lane 5), Str2-3G; (Lane 6), Str3-3G; (Lane 7), Str1-5G; (Lane 8), Str2-5G; (Lane 9), Str3-5G; (Lane 10), Str1-4GC; (Lane 11), Str2-4GC; (Lane 12), Str3-4GC.

Head-removed H3 HA were generated by replacing head domain (amino acids S61-P322), (amino acids S62-K323) or (amino acids S62-V325) with 3G, 4G, 5G or 4GC linker (FIG. 12). The protein expression of these candidates was not largely affected by different mutation sites as evidenced by the similar intensity of bands in Western blot (FIG. 13). Too much truncation and retaining will lead to failure in protein expression and misfolding. Therefore, an truncation range with 3 amino acids distance from S61 and K323 may be optimal.

Figure 14:
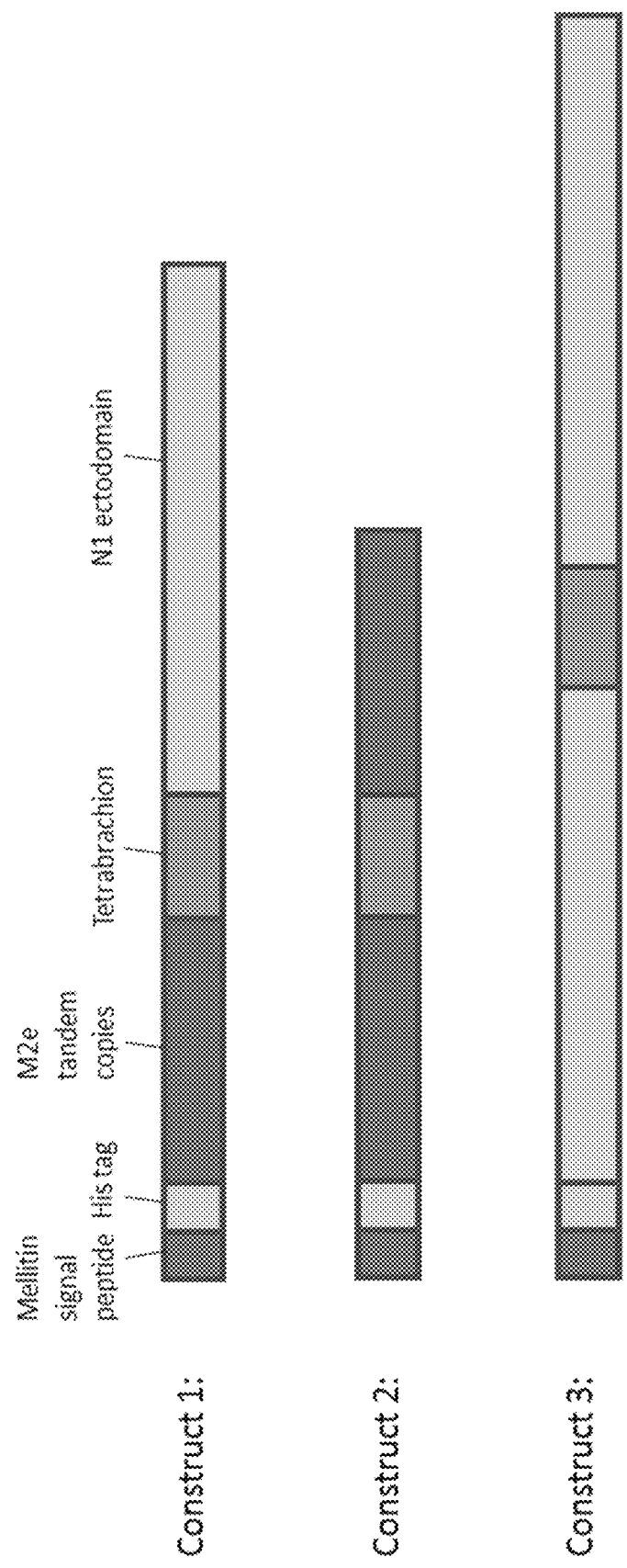
FIG. 14 shows a schematic diagram of tetrabrachion motif screwed tetramer protein construct.

The tetrabrachion motif screwed tetramer protein retains native functions and can be stably expressed. In our study, tetrabrachion motif was fused with tandem copies of M2e at N-terminal and followed by N1 ectodomain including stalk and head (FIG. 14). Construct 2 and 3 are simulated tetrabrachion motif screwed tetramer constructs (FIG. 14). With flanked tandem copies of M2e or flanked N1 ectodomain at both sides of tetrabrachion motif, it is speculated that the tetramer proteins can be expressed and retains native protein function.

Example 3

Coated M2e-Neuraminidase fusion protein nanoclusters display neuraminidase activity. FIGS. 15A and 15B shows example structure of 4M2e-NA nanoparticles. FIG. 15A shows combination of 4M2e and 4M2e-NA fusion proteins. GS linker: glycine and serine GGSGGG (SEQ ID NO:20); M2e: combined M2e sequence from human, swine, wild bird, and domestic fowl with tetrabrachion together; M2e+ NA: combined stalk and head of neuraminidase 1 (from A/Vietnam/1203/2004/) with M2e above. FIG. 15B shows schematic formation of M2e-NA nano-particle. 4M2e-NA was covered on the 4M2e core.

Figure 16A:
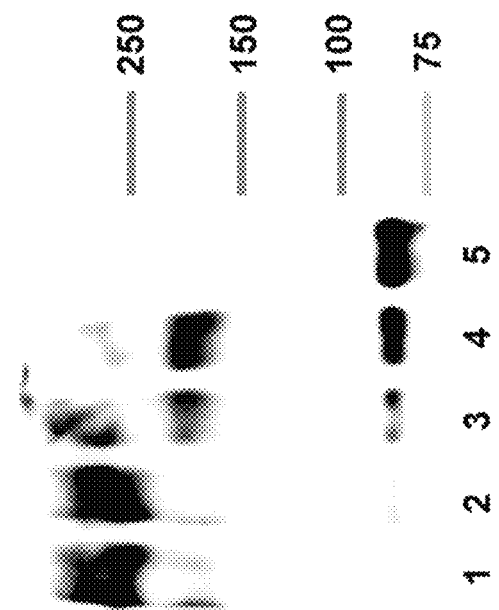
Figure 16B:
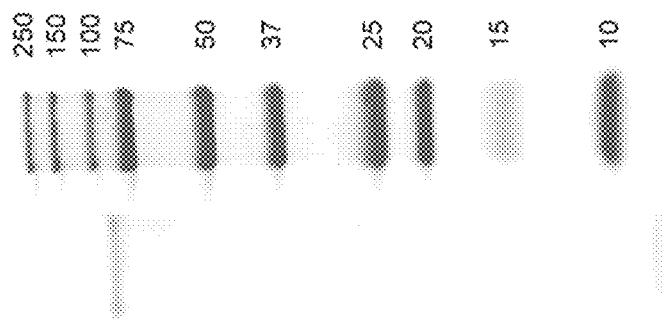
Figure 16C:
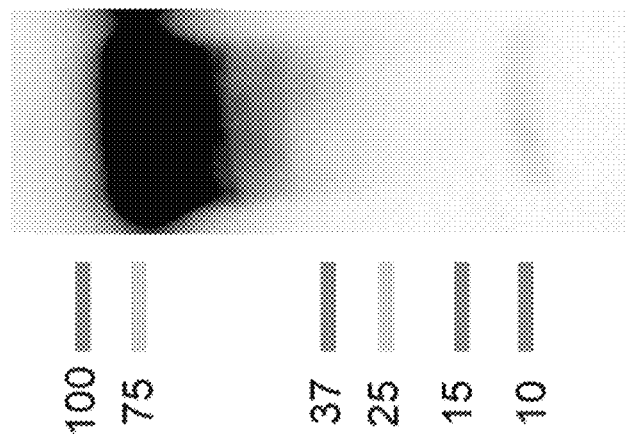
Figure 16D:
Figure 16E:
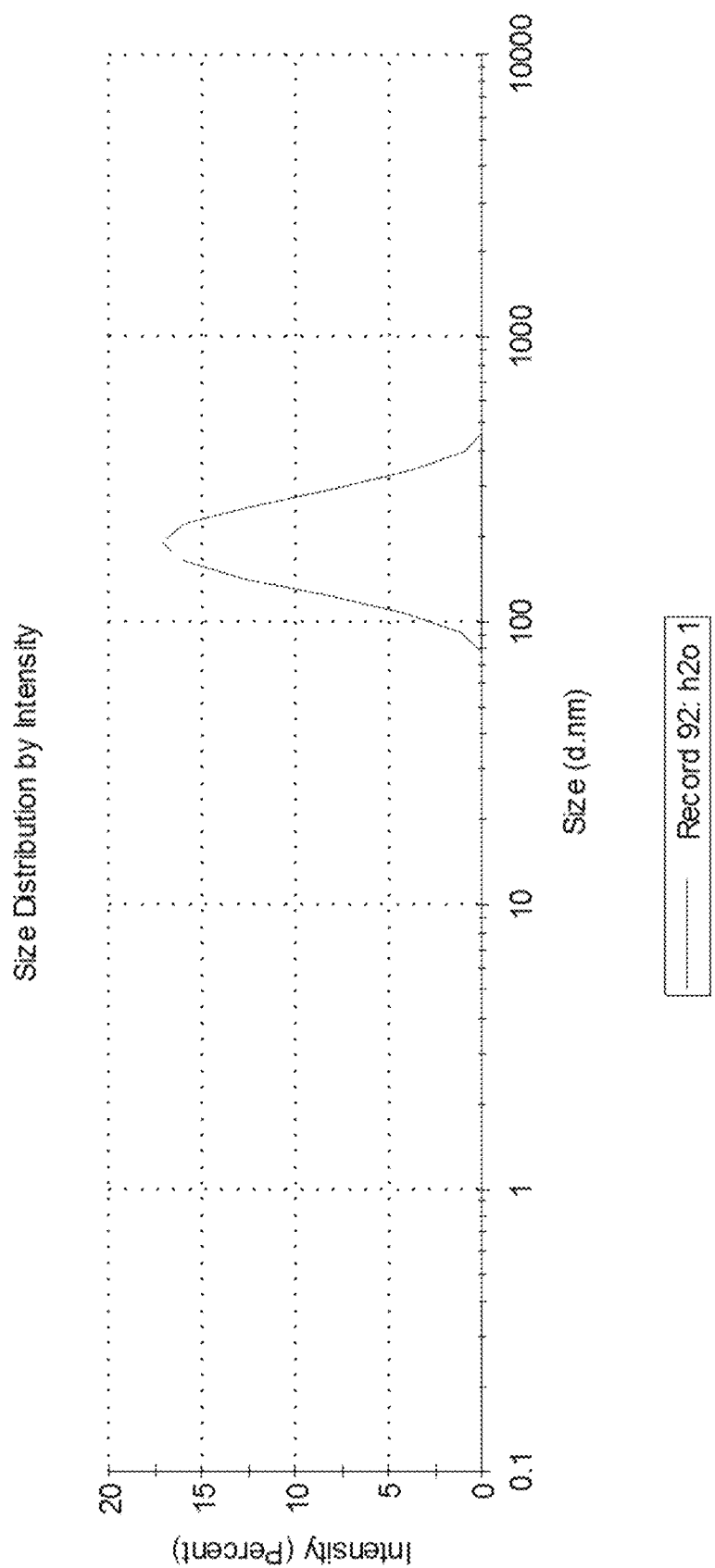

FIGS. 16A to 16F show the formation of M2e-NA nanoparticle. FIG. 16A shows M2e-NA fusion protein cross-linked by 12.5, 7.5, 2.5, and 1 mM of BS3, as in line 1, 2, 3, 4, respectively. Line 5: soluble M2e+NA fusion protein. FIG. 16B shows Coomassie blue staining of M2e-NA nanoparticle. FIGS. 16C and 16D show Western blot assay of M2e-NA nanoparticle. C: M2e antibody; D: NA antibody. FIG. 16E shows the size of formed M2e+NA nanoparticle: 198.2+/−62.41 nm. FIG. 16F shows results of a neuraminidase activity test. The concentration of each protein: M2e+ NA nano particle: 1 mg/ml; soluble M2e+NA: 1 mg/ml; H5N1 virus: 2.5 mg/ml; BSA: 2 mg/ml.

Figure 17:
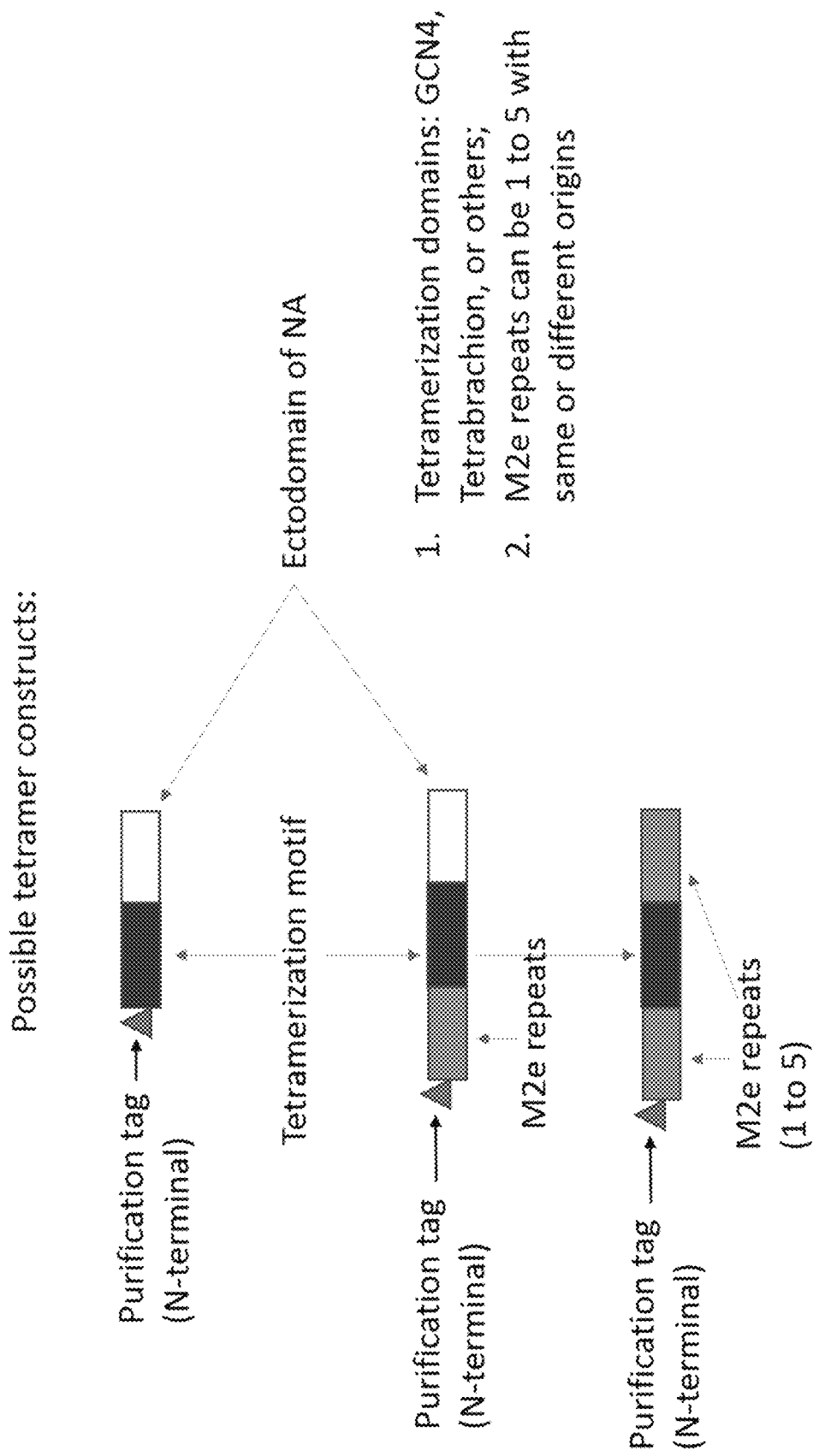
FIG. 17 shows example tetramer constructs.

FIG. 17 shows example tetramer constructs.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

Example 4

The following is an Influenza B HA stalk ectodomain sequence:

(SEQ ID NO: 36)
MKFLVNVALVFMVVYISYIYAAADRICTGITSSNSPHVVKTATQGEVNVT

GVIPLTTTGGGCVKTPLKLANGTKYRPPAKLLTEQGFFGAIAGFLEGGW

-continued

EGMIAGWHGYTSHGAHGVAVAADLKSTQEAINKITKNLNSLSELEGGGSS

ADTICSQIELAVLLSNEGIINSEDEHLLALERKLKKMLGPSAVEIGNGCF

ETKHKCNQTCLDRIAAGTFDAGEFSLPTPGSSGGSSGMKQIEDKIEEILS

KIYHIENEIARIKKLDDDDKHHHHHH

Figure 19A:
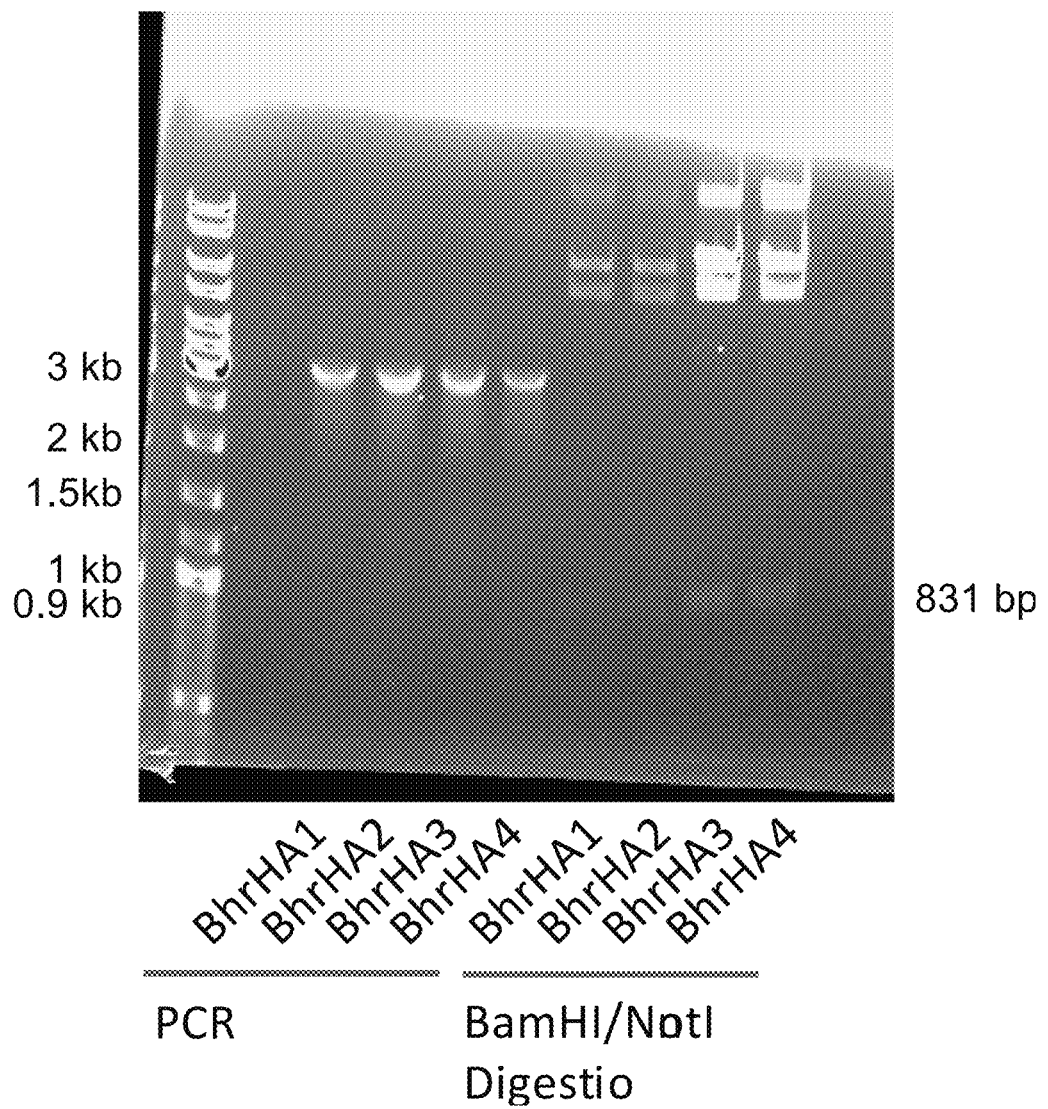
FIG. 19A shows PCR and restriction digest data from construction of the plasmid for expression of B/hrHA.

This head-removed influenza B HA (B/hrHA) was designed by replacing head domain (amino acids P33-W321 and V404-R432) with a GGGGC (SEQ ID NO:18) or GGGSS (SEQ ID NO:19) linker (FIG. 18). Sequences at the N-terminal and C-terminal were also added for expression and functionalization of the protein. The DNA sequence encoding this construct (SEQ ID NO:37) was cloned into a pFastBac1 expression vector using NotI and BamHI restriction sites. This vector permits expression of the protein in Sf9 insect cells using a PH promoter. After ligation of the insert into the plasmid, the insert could be identified by PCR and by restriction digest analysis (FIG. 19A). To generate this data, 3 µg of the bacmid was digested using BamHI and NotI restriction enzymes to cut. For PCR, 0.1 µL of the bacmid was used as template combined with the M13 forward and reverse primers for amplification.

Figure 19B:
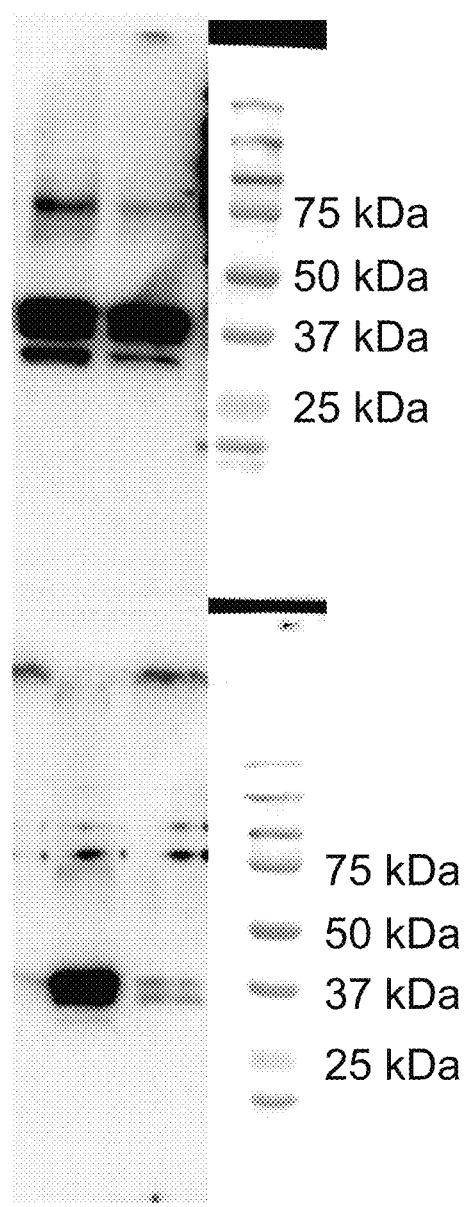
FIG. 19B displays Western blot data evidence of productive expression of B/hrHA into the supernatant of Sf9 cells that have been transfected with the plasmid encoding B/hrHA.

The hrHA protein was efficiently expressed by Sf9 cells as evidenced by the robust mass of protein of correct size that is clear in Western blot analysis of the supernatant from transfected cells (FIG. 19B). Inappropriate modification and truncation leading to protein misfolding would result in retention of the protein in the cells with a clear failure in secrete protein into the supernatant. To generate this data 2 µg of the B/hrHA bacmid (in 100 µl) was combined with 10 µL Cellfectin II (in 100 µl) for 40 min at RT. Attached Sf9 cells were transfected in 6 well plate by adding 200 µL of the liposome mixture. Transfection was incubated for 5 days at 28° C. A 20 µL sample of supernatant was taken for analysis, separated by SDS-PAGE gel, and analyzed by Western.

What is claimed is:

1. A nanoparticle formed by crosslinking a fusion protein with a crosslinking agent and/or desolvating the fusion protein with a desolvating agent, wherein the fusion protein comprises a series of 2 to 8 influenza virus matrix protein 2 extracellular (M2e) domains, wherein the series of 2 to 8 influenza virus M2e domains is linked to a multimerization domain, wherein the fusion protein further comprises influenza neuraminidase (NA) protein linked to the multimerization domain.

2. The nanoparticle of claim 1, wherein the multimerization domain comprises a tetramerization domain.

3. The nanoparticle of claim 2, wherein the tetramerization domain comprises a GCN4 or tetrabrachion protein.

4. The nanoparticle of claim 1, wherein the M2e domains are linked to each other by a flexible linker comprising 3 to 9 amino acids selected from glycine, alanine, and serine.

5. The nanoparticle of claim 1, wherein the fusion protein comprises a series of 2 to 8 M2e domains linked to the N-terminus of the multimerization domain and series of 2 to 8 M2e domains linked to the C-terminus of the multimerization domain.

6. The nanoparticle of claim 1, wherein the series of 2 to 8 M2e domains are linked to the N-terminus of the multimerization domain and the NA protein is linked to the C-terminus of the multimerization domain.

7. The nanoparticle of claim 1, comprising four M2e (4M2e) domains in each series.

8. The nanoparticle of claim 1, comprising two or more heterologous M2e domains.

9. The nanoparticle of claim 8, wherein the fusion protein comprises one or more M2e domains from a human influenza, one or more M2e domains from a swine influenza, and one or more M2e domains from an avian influenza.

10. The nanoparticle of claim 1, wherein the fusion protein further comprises a signal peptide at the N-terminus.

11. The nanoparticle of claim 1, wherein the nanoparticle is coated with an influenza antigen.

12. The nanoparticle of claim 11, wherein the antigen comprises a truncated influenza hemagglutin (HA) protein lacking a head domain.

\* \* \* \* \*

SEQUENCE LISTING

```
<160> NUMBER OF SEQ ID NOS: 44

<210> SEQ ID NO 1
<211> LENGTH: 23
<212> TYPE: PRT
<213> ORGANISM: Artificial Sequence
<220> FEATURE:
<223> OTHER INFORMATION: Synthetic Construct

<400> SEQUENCE: 1

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic Construct

<400> SEQUENCE: 2

Ser Leu Leu Thr Glu Val Glu Thr Pro Thr Arg Ser Glu Trp Glu Cys
1               5                   10                  15

Arg Cys Ser Asp Ser Ser Asp
            20

<210> SEQ ID NO 3
<211> LENGTH: 23
<212> TYPE: PRT
<213> ORGANISM: Artificial Sequence
<220> FEATURE:
<223> OTHER INFORMATION: Synthetic Construct

<400> SEQUENCE: 3

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 4
<211> LENGTH: 23
<212> TYPE: PRT
<213> ORGANISM: Artificial Sequence
```

```
<220> FEATURE:
<223> OTHER INFORMATION: Synthetic Construct

<400> SEQUENCE: 4

Ser Leu Leu Thr Glu Val Glu Thr Pro Thr Arg Thr Gly Trp Glu Cys
1               5                   10                  15

Asn Cys Ser Gly Ser Ser Glu
            20

<210> SEQ ID NO 5
<211> LENGTH: 23
<212> TYPE: PRT
<213> ORGANISM: Artificial Sequence
<220> FEATURE:
<223> OTHER INFORMATION: Synthetic Construct

<400> SEQUENCE: 5

Ser Leu Leu Thr Glu Val Glu Thr Pro Ile Arg Asn Glu Trp Gly Cys
1               5                   10                  15

Arg Cys Asn Gly Ser Ser Asp
            20

<210> SEQ ID NO 6
<211> LENGTH: 23
<212> TYPE: PRT
<213> ORGANISM: Artificial Sequence
<220> FEATURE:
<223> OTHER INFORMATION: Synthetic Construct

<400> SEQUENCE: 6

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 7
<211> LENGTH: 23
<212> TYPE: PRT
<213> ORGANISM: Artificial Sequence
<220> FEATURE:
<223> OTHER INFORMATION: Synthetic Construct

<400> SEQUENCE: 7

Ser Leu Leu Thr Glu Val Glu Thr Pro Thr Arg Ser Glu Trp Glu Cys
1               5                   10                  15

Arg Cys Ser Asp Ser Ser Asp
            20

<210> SEQ ID NO 8
<211> LENGTH: 23
<212> TYPE: PRT
<213> ORGANISM: Artificial Sequence
<220> FEATURE:
<223> OTHER INFORMATION: Synthetic Construct

<400> SEQUENCE: 8

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 9
<211> LENGTH: 23
<212> TYPE: PRT
```

<213> ORGANISM: Artificial Sequence
<220> FEATURE:
<223> OTHER INFORMATION: Synthetic Construct

<400> SEQUENCE: 9

Ser Leu Leu Thr Glu Val Glu Thr Pro Ile Arg Asn Glu Trp Gly Cys
1               5                   10                  15

Arg Cys Asn Gly Ser Ser Asp
            20

<210> SEQ ID NO 10
<211> LENGTH: 23
<212> TYPE: PRT
<213> ORGANISM: Artificial Sequence
<220> FEATURE:
<223> OTHER INFORMATION: Synthetic Construct

<400> SEQUENCE: 10

Ser Leu Leu Thr Glu Val Glu Thr Pro Ile Arg Asn Glu Trp Gly Cys
1               5                   10                  15

Arg Cys Asn Gly Ser Ser Asp
            20

<210> SEQ ID NO 11
<211> LENGTH: 23
<212> TYPE: PRT
<213> ORGANISM: Artificial Sequence
<220> FEATURE:
<223> OTHER INFORMATION: Synthetic Construct

<400> SEQUENCE: 11

Ser Leu Leu Thr Glu Val Glu Thr Pro Ile Arg Asn Glu Trp Gly Ser
1               5                   10                  15

Arg Ser Asn Asp Ser Ser Asp
            20

<210> SEQ ID NO 12
<211> LENGTH: 23
<212> TYPE: PRT
<213> ORGANISM: Artificial Sequence
<220> FEATURE:
<223> OTHER INFORMATION: Synthetic Construct

<400> SEQUENCE: 12

Ser Leu Leu Thr Glu Val Glu Thr Pro Thr Arg Ser Glu Trp Glu Ser
1               5                   10                  15

Arg Ser Ser Asp Ser Ser Asp
            20

<210> SEQ ID NO 13
<211> LENGTH: 23
<212> TYPE: PRT
<213> ORGANISM: Artificial Sequence
<220> FEATURE:
<223> OTHER INFORMATION: Synthetic Construct

<400> SEQUENCE: 13

Ser Leu Leu Thr Glu Val Glu Thr Pro Thr Arg Asn Gly Trp Glu Ser
1               5                   10                  15

Lys Ser Ser Gly Ser Ser Asp
            20

<210> SEQ ID NO 14
<211> LENGTH: 23

```
<212> TYPE: PRT
<213> ORGANISM: Artificial Sequence
<220> FEATURE:
<223> OTHER INFORMATION: Synthetic Construct

<400> SEQUENCE: 14

Ser Leu Leu Thr Glu Val Glu Thr Pro Thr Arg Asn Gly Trp Glu Ser
1               5                   10                  15

Asn Ser Ser Asp Ser Ser Asp
            20

<210> SEQ ID NO 15
<211> LENGTH: 528
<212> TYPE: PRT
<213> ORGANISM: Artificial Sequence
<220> FEATURE:
<223> OTHER INFORMATION: Synthetic Construct

<400> SEQUENCE: 15

Met Lys Thr Ile Ile Ala Leu Ser Tyr Ile Phe Cys Leu Pro Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Ile His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300
```

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
            325                 330                 335

Arg Asn Val Pro Glu Lys Gln Thr Arg Gly Leu Phe Gly Ala Ile Ala
        340                 345                 350

Gly Phe Ile Glu Asn Gly Trp Glu Gly Met Ile Asp Gly Trp Tyr Gly
    355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Glu Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

<210> SEQ ID NO 16
<211> LENGTH: 4
<212> TYPE: PRT
<213> ORGANISM: Artificial Sequence
<220> FEATURE:
<223> OTHER INFORMATION: Synthetic Construct

<400> SEQUENCE: 16

Gly Gly Gly Gly
1

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Gly Gly Gly Gly Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

```
Gly Gly Gly Gly Cys
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Gly Gly Gly Ser Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

Gly Gly Ser Gly Gly Gly
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Ile Arg Asn Glu Trp Gly Ser Arg Ser Asn
1               5                   10

<210> SEQ ID NO 22
<211> LENGTH: 23
<212> TYPE: PRT
<213> ORGANISM: Artificial Sequence
<220> FEATURE:
<223> OTHER INFORMATION: Synthetic Construct

<400> SEQUENCE: 22

Ser Leu Leu Thr Glu Val Glu Thr Pro Ile Arg Asn Glu Trp Gly Ser
1               5                   10                  15

Arg Ser Asn Asp Ser Ser Asp
            20

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

Pro Thr Arg Ser Glu Trp Glu Ser Arg Ser Ser
1               5                   10

<210> SEQ ID NO 24
<211> LENGTH: 23
<212> TYPE: PRT
<213> ORGANISM: Artificial Sequence
<220> FEATURE:
<223> OTHER INFORMATION: Synthetic Construct
```

<400> SEQUENCE: 24

Ser Leu Leu Thr Glu Val Glu Thr Pro Thr Arg Ser Glu Trp Glu Ser
1               5                   10                  15

Arg Ser Ser Asp Ser Ser Asp
            20

<210> SEQ ID NO 25
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Asn, His, or Lys
<220> FEATURE:
<221> NAME/KEY: MISC_FEATURE
<222> LOCATION: (5)..(5)
<223> OTHER INFORMATION: Xaa is Glu or Gly

<400> SEQUENCE: 25

Pro Thr Arg Xaa Xaa Trp Glu Ser Arg Ser Ser
1               5                   10

<210> SEQ ID NO 26
<211> LENGTH: 21
<212> TYPE: PRT
<213> ORGANISM: Artificial Sequence
<220> FEATURE:
<223> OTHER INFORMATION: Synthetic Construct

<400> SEQUENCE: 26

Ser Leu Leu Thr Glu Val Glu Thr Pro Thr Arg Asn Glu Trp Glu Ser
1               5                   10                  15

Arg Ser Ser Asp Ser
            20

<210> SEQ ID NO 27
<211> LENGTH: 21
<212> TYPE: PRT
<213> ORGANISM: Artificial Sequence
<220> FEATURE:
<223> OTHER INFORMATION: Synthetic Construct

<400> SEQUENCE: 27

Ser Leu Leu Thr Glu Val Glu Thr Pro Thr Arg Asn Gly Trp Glu Cys
1               5                   10                  15

Arg Cys Ser Asp Ser
            20

<210> SEQ ID NO 28
<211> LENGTH: 23
<212> TYPE: PRT
<213> ORGANISM: Artificial Sequence
<220> FEATURE:
<223> OTHER INFORMATION: Synthetic Construct

<400> SEQUENCE: 28

Ser Leu Leu Thr Glu Val Glu Thr Pro Thr Arg His Glu Trp Glu Cys
1               5                   10                  15

Arg Cys Ser Asp Ser Ser Asp
            20

<210> SEQ ID NO 29

<211> LENGTH: 22
<212> TYPE: PRT
<213> ORGANISM: Artificial Sequence
<220> FEATURE:
<223> OTHER INFORMATION: Synthetic Construct

<400> SEQUENCE: 29

Ser Leu Leu Thr Glu Val Glu Thr Pro Thr Arg Lys Glu Trp Glu Cys
1               5                   10                  15

Arg Cys Ser Asp Ser Ser
            20

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Leu Thr Arg Asn Gly Trp Gly Cys Arg Cys Ser
1               5                   10

<210> SEQ ID NO 31
<211> LENGTH: 23
<212> TYPE: PRT
<213> ORGANISM: Artificial Sequence
<220> FEATURE:
<223> OTHER INFORMATION: Synthetic Construct

<400> SEQUENCE: 31

Ser Leu Leu Thr Glu Val Glu Thr Leu Thr Arg Asn Gly Trp Gly Cys
1               5                   10                  15

Arg Cys Ser Asp Ser Ser Asp
            20

<210> SEQ ID NO 32
<211> LENGTH: 27
<212> TYPE: PRT
<213> ORGANISM: Artificial Sequence
<220> FEATURE:
<223> OTHER INFORMATION: Synthetic Construct

<400> SEQUENCE: 32

Met Lys Phe Leu Val Asn Val Ala Leu Val Phe Met Val Val Tyr Ile
1               5                   10                  15

Ser Tyr Ile Tyr Ala Asp Pro Ile Asn Met Thr
            20                  25

<210> SEQ ID NO 33
<211> LENGTH: 20
<212> TYPE: PRT
<213> ORGANISM: Artificial Sequence
<220> FEATURE:
<223> OTHER INFORMATION: Synthetic Construct

<400> SEQUENCE: 33

Met Val Ser Ala Ile Val Leu Tyr Val Leu Leu Ala Ala Ala Ala His
1               5                   10                  15

Ser Ala Phe Ala
            20

<210> SEQ ID NO 34
<211> LENGTH: 20
<212> TYPE: PRT

<213> ORGANISM: Artificial Sequence
<220> FEATURE:
<223> OTHER INFORMATION: Synthetic Construct

<400> SEQUENCE: 34

```
Met Pro Leu Tyr Lys Leu Leu Asn Val Leu Trp Leu Val Ala Val Ser
1               5                   10                  15

Asn Ala Ile Pro
            20
```

<210> SEQ ID NO 35
<211> LENGTH: 33
<212> TYPE: PRT
<213> ORGANISM: Artificial Sequence
<220> FEATURE:
<223> OTHER INFORMATION: Synthetic Construct

<400> SEQUENCE: 35

```
Gly Gly Leu Lys Gln Ile Glu Asp Lys Leu Glu Glu Ile Leu Ser Lys
1               5                   10                  15

Leu Tyr His Ile Glu Asn Glu Leu Ala Arg Ile Lys Lys Leu Leu Gly
            20                  25                  30

Glu
```

<210> SEQ ID NO 36
<211> LENGTH: 276
<212> TYPE: PRT
<213> ORGANISM: Artificial Sequence
<220> FEATURE:
<223> OTHER INFORMATION: Synthetic Construct

<400> SEQUENCE: 36

```
Met Lys Phe Leu Val Asn Val Ala Leu Val Phe Met Val Val Tyr Ile
1               5                   10                  15

Ser Tyr Ile Tyr Ala Ala Ala Asp Arg Ile Cys Thr Gly Ile Thr Ser
            20                  25                  30

Ser Asn Ser Pro His Val Val Lys Thr Ala Thr Gln Gly Glu Val Asn
        35                  40                  45

Val Thr Gly Val Ile Pro Leu Thr Thr Thr Gly Gly Gly Gly Cys Val
    50                  55                  60

Lys Thr Pro Leu Lys Leu Ala Asn Gly Thr Lys Tyr Arg Pro Pro Ala
65                  70                  75                  80

Lys Leu Leu Thr Glu Gln Gly Phe Phe Gly Ala Ile Ala Gly Phe Leu
                85                  90                  95

Glu Gly Gly Trp Glu Gly Met Ile Ala Gly Trp His Gly Tyr Thr Ser
            100                 105                 110

His Gly Ala His Gly Val Ala Val Ala Ala Asp Leu Lys Ser Thr Gln
        115                 120                 125

Glu Ala Ile Asn Lys Ile Thr Lys Asn Leu Asn Ser Leu Ser Glu Leu
    130                 135                 140

Glu Gly Gly Gly Ser Ser Ala Asp Thr Ile Cys Ser Gln Ile Glu Leu
145                 150                 155                 160

Ala Val Leu Leu Ser Asn Glu Gly Ile Ile Asn Ser Glu Asp Glu His
                165                 170                 175

Leu Leu Ala Leu Glu Arg Lys Leu Lys Lys Met Leu Gly Pro Ser Ala
            180                 185                 190

Val Glu Ile Gly Asn Gly Cys Phe Glu Thr Lys His Lys Cys Asn Gln
        195                 200                 205
```

```
Thr Cys Leu Asp Arg Ile Ala Ala Gly Thr Phe Asp Ala Gly Glu Phe
            210                 215                 220

Ser Leu Pro Thr Pro Gly Ser Ser Gly Gly Ser Ser Gly Met Lys Gln
225                 230                 235                 240

Ile Glu Asp Lys Ile Glu Glu Ile Leu Ser Lys Ile Tyr His Ile Glu
                245                 250                 255

Asn Glu Ile Ala Arg Ile Lys Lys Leu Asp Asp Asp Lys His His
            260                 265                 270

His His His His
        275

<210> SEQ ID NO 37
<211> LENGTH: 851
<212> TYPE: DNA
<213> ORGANISM: Artificial Sequence
<220> FEATURE:
<223> OTHER INFORMATION: Synthetic Construct

<400> SEQUENCE: 37
ggatccatga tgaagtttct ggtcaacgta gcgttggtct tcatggtcgt ctacataagt      60
tacatttatg ccgcggcgga tcgcatctgc acaggaatca cgagtagcaa ttccccacat    120
gtcgttaaga ctgctaccca gggcgaagta acgtcacag gtgtcattcc actgaccacc     180
accggaggcg gaggctgcgt caagactccg cttaagctcg cgaacggaac taaatacaga    240
ccgcccgcga agctgctgac cgaacaaggt tttttcggag ccatagcagg tttccttgaa    300
ggaggatggg aaggaatgat agcaggatgg cacggttata catctcatgg tgctcatggt    360
gtggcagtag ctgccgatct caagagcaca caagaggcaa tcaataagat cacgaagaac    420
ctgaactcgc ttagcgagtt ggagggtggt ggctcgtcag cagatacgat atgctctcag    480
attgaactcg ctgtgctgct ctcaaatgag ggcatcataa attccgaaga tgaacatctt    540
ctggcgcttg agcgtaaatt gaagaagatg ctcggtccat cggcagtgga aattggaaac    600
ggttgttttg aaacaaaaca caaatgcaac cagacgtgct tggacagaat agctgctggc    660
actttcgacg caggagagtt ttcgcttcct acgcctggtt caagtggtgg ttccagtgga    720
atgaaacaaa ttgaagacaa aatagaagag atcctttcaa agatatatca tatcgaaaac    780
gaaatcgctc gcatcaaaaa attggatgac gatgataagc accaccatca tcatcattga    840
taagcggccg c                                                          851

<210> SEQ ID NO 38
<211> LENGTH: 162
<212> TYPE: PRT
<213> ORGANISM: Artificial Sequence
<220> FEATURE:
<223> OTHER INFORMATION: Synthetic Construct

<400> SEQUENCE: 38

Met Ser Leu Leu Thr Glu Val Glu Thr Pro Ile Arg Asn Glu Trp Gly
1               5                   10                  15

Ser Arg Ser Asn Asp Ser Ser Asp Pro Gly Gly Ser Ser Gly Gly Ser
            20                  25                  30

Ser Ser Leu Leu Thr Glu Val Glu Thr Pro Thr Arg Ser Glu Trp Glu
        35                  40                  45

Ser Arg Ser Ser Asp Ser Ser Asp Pro Gly Gly Ser Ser Gly Gly Ser
    50                  55                  60

Ser Ser Leu Leu Thr Glu Val Glu Thr Pro Thr Arg Asn Gly Trp Glu
65                  70                  75                  80
```

Ser Lys Ser Ser Gly Ser Ser Asp Pro Gly Ser Gly Ser Gly
                85                  90                  95

Ser Ser Leu Leu Thr Glu Val Glu Thr Pro Thr Arg Asn Gly Trp Glu
            100                 105                 110

Ser Asn Ser Ser Asp Ser Ser Asp Pro Gly Gly Gly Ser Ser Ser
        115                 120                 125

Ser Leu Glu Leu Lys Gln Ile Glu Asp Lys Leu Glu Glu Ile Leu Ser
    130                 135                 140

Lys Leu Tyr His Ile Glu Asn Glu Leu Ala Arg Ile Lys Lys Leu Leu
145                 150                 155                 160

Gly Glu

<210> SEQ ID NO 39
<211> LENGTH: 541
<212> TYPE: PRT
<213> ORGANISM: Artificial Sequence
<220> FEATURE:
<223> OTHER INFORMATION: Synthetic Construct

<400> SEQUENCE: 39

Cys Thr Gly Ile Thr Ser Ser Asn Ser Pro His Val Val Lys Thr Ala
1               5                   10                  15

Thr Gln Gly Glu Val Asn Val Thr Gly Val Ile Pro Leu Thr Thr Thr
            20                  25                  30

Pro Thr Lys Ser His Phe Ala Asn Leu Lys Gly Thr Glu Thr Arg Gly
        35                  40                  45

Lys Leu Cys Pro Lys Cys Leu Asn Cys Thr Asp Leu Asp Val Ala Leu
    50                  55                  60

Gly Arg Pro Lys Cys Thr Gly Lys Ile Pro Ser Ala Arg Val Ser Ile
65                  70                  75                  80

Leu His Glu Val Arg Pro Val Thr Ser Gly Cys Phe Pro Ile Met His
                85                  90                  95

Asp Arg Thr Lys Ile Arg Gln Leu Pro Asn Leu Leu Arg Gly Tyr Glu
            100                 105                 110

His Ile Arg Leu Ser Thr His Asn Val Ile Asn Ala Glu Asn Ala Pro
        115                 120                 125

Gly Gly Pro Tyr Lys Ile Gly Thr Ser Gly Ser Cys Pro Asn Ile Thr
    130                 135                 140

Asn Gly Asn Gly Phe Phe Ala Thr Met Ala Trp Ala Val Pro Lys Asn
145                 150                 155                 160

Asp Lys Asn Lys Thr Ala Thr Asn Pro Leu Thr Ile Glu Val Pro Tyr
                165                 170                 175

Ile Cys Thr Glu Gly Glu Asp Gln Ile Thr Val Trp Gly Phe His Ser
            180                 185                 190

Asp Asn Glu Thr Gln Met Ala Lys Leu Tyr Gly Asp Ser Lys Pro Gln
        195                 200                 205

Lys Phe Thr Ser Ser Ala Asn Gly Val Thr Thr His Tyr Val Ser Gln
    210                 215                 220

Ile Gly Gly Phe Pro Asn Gln Thr Glu Asp Gly Gly Leu Pro Gln Ser
225                 230                 235                 240

Gly Arg Ile Val Val Asp Tyr Met Val Gln Lys Ser Gly Lys Thr Gly
                245                 250                 255

Thr Ile Thr Tyr Gln Arg Gly Ile Leu Leu Pro Gln Lys Val Trp Cys
            260                 265                 270

```
Ala Ser Gly Arg Ser Lys Val Ile Lys Gly Ser Leu Pro Leu Ile Gly
            275                 280                 285

Glu Ala Asp Cys Leu His Glu Lys Tyr Gly Gly Leu Asn Lys Ser Lys
        290                 295                 300

Pro Tyr Tyr Thr Gly Glu His Ala Lys Ala Ile Gly Asn Cys Pro Ile
305                 310                 315                 320

Trp Val Lys Thr Pro Leu Lys Leu Ala Asn Gly Thr Lys Tyr Arg Pro
                325                 330                 335

Pro Ala Lys Leu Leu Lys Glu Arg Gly Phe Phe Gly Ala Ile Ala Gly
            340                 345                 350

Phe Leu Glu Gly Gly Trp Glu Gly Met Ile Ala Gly Trp His Gly Tyr
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Glu Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asp Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

His Thr Ile Leu Leu Tyr Tyr Ser Thr Ala Ala Ser Ser
    530                 535                 540

<210> SEQ ID NO 40
<211> LENGTH: 239
<212> TYPE: PRT
<213> ORGANISM: Artificial Sequence
<220> FEATURE:
<223> OTHER INFORMATION: Synthetic Construct

<400> SEQUENCE: 40

Cys Thr Gly Ile Thr Ser Ser Asn Ser Pro His Val Val Lys Thr Ala
1               5                   10                  15

Thr Gln Gly Glu Val Asn Val Thr Gly Val Ile Pro Leu Thr Thr Thr
            20                  25                  30

Gly Gly Gly Gly Cys Val Lys Thr Pro Leu Lys Leu Ala Asn Gly Thr
        35                  40                  45

Lys Tyr Arg Pro Pro Ala Lys Leu Leu Thr Glu Gln Gly Phe Phe Gly
    50                  55                  60

Ala Ile Ala Gly Phe Leu Glu Gly Gly Trp Glu Gly Met Ile Ala Gly
65                  70                  75                  80

Trp His Gly Tyr Thr Ser His Gly Ala His Gly Val Ala Val Ala Ala
                85                  90                  95
```

```
Asp Leu Lys Ser Thr Gln Glu Ala Ile Asn Lys Ile Thr Lys Asn Leu
            100                 105                 110

Asn Ser Leu Ser Glu Leu Glu Gly Gly Ser Ser Ala Asp Thr Ile
        115                 120                 125

Cys Ser Gln Ile Glu Leu Ala Val Leu Leu Ser Asn Glu Gly Ile Ile
130                 135                 140

Asn Ser Glu Asp Glu His Leu Leu Ala Leu Glu Arg Lys Leu Lys Lys
145                 150                 155                 160

Met Leu Gly Pro Ser Ala Val Glu Ile Gly Asn Gly Cys Phe Glu Thr
                165                 170                 175

Lys His Lys Cys Asn Gln Thr Cys Leu Asp Arg Ile Ala Ala Gly Thr
            180                 185                 190

Phe Asp Ala Gly Glu Phe Ser Leu Pro Thr Pro Gly Ser Ser Gly Gly
        195                 200                 205

Ser Ser Gly Met Lys Gln Ile Glu Asp Lys Ile Glu Glu Ile Leu Ser
210                 215                 220

Lys Ile Tyr His Ile Glu Asn Glu Ile Ala Arg Ile Lys Lys Leu
225                 230                 235

<210> SEQ ID NO 41
<211> LENGTH: 291
<212> TYPE: PRT
<213> ORGANISM: Artificial Sequence
<220> FEATURE:
<223> OTHER INFORMATION: Synthetic Construct

<400> SEQUENCE: 41

Met Lys Thr Ile Ile Ala Leu Ser Tyr Ile Phe Cys Leu Pro Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Gly Gly Gly Gly
    50                  55                  60

Lys Tyr Cys Lys Gln Asn Thr Leu Lys Leu Ala Thr Gly Met Arg Asn
65                  70                  75                  80

Val Pro Glu Lys Gln Thr Arg Gly Leu Phe Gly Ala Ile Gly Phe Ile
                85                  90                  95

Glu Asn Gly Trp Glu Gly Met Ile Asp Gly Trp Tyr Gly Phe Arg His
            100                 105                 110

Gln Asn Ser Glu Gly Thr Gly Gln Ala Ala Asp Leu Lys Ser Thr Gln
        115                 120                 125

Ala Ala Ile Asp Gln Ile Asn Gly Lys Leu Asn Arg Val Ile Glu Lys
130                 135                 140

Thr Asn Glu Lys Gly Ser Gly Gly Ser Gly Trp Cys Tyr Asn Ala Glu
145                 150                 155                 160

Leu Leu Val Ala Leu Glu Asn Gln His Thr Ile Asp Leu Thr Asp Ser
                165                 170                 175

Glu Met Asn Lys Leu Phe Glu Lys Thr Arg Arg Gln Leu Arg Glu Asn
            180                 185                 190

Ala Glu Glu Met Gly Asn Gly Cys Phe Lys Ile Tyr His Lys Cys Asp
        195                 200                 205

Asn Ala Cys Ile Glu Ser Ile Arg Asn Gly Thr Tyr Asp His Asp Val
210                 215                 220
```

-continued

```
Tyr Arg Asp Glu Ala Leu Asn Asn Arg Phe Gln Ile Lys Gly Val Glu
225                 230                 235                 240

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
            325                 330                 335

Arg Asn Val Pro Glu Lys Gln Thr Arg Gly Leu Phe Gly Ala Ile Gly
            340                 345                 350

Phe Ile Glu Asn Gly Trp Glu Gly Met Ile Asp Gly Trp Tyr Gly Phe
            355                 360                 365

Arg His Gln Asn Ser Glu Gly Thr Gly Gln Ala Ala Asp Leu Lys Ser
            370                 375                 380

Thr Gln Ala Ala Ile Asp Gln Ile Asn Gly Lys Leu Asn Arg Val Ile
385                 390                 395                 400

Glu Lys Thr Asn Glu Lys Phe His Gln Ile Glu Lys Glu Phe Ser Glu
            405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
            435                 440                 445

Gln His Thr Ile Asp Leu Thr Asp Ser Glu Met Asn Lys Leu Phe Glu
            450                 455                 460

Lys Thr Arg Arg Gln Leu Arg Glu Asn Ala Glu Glu Met Gly Asn Gly
465                 470                 475                 480

Cys Phe Lys Ile Tyr His Lys Cys Asp Asn Ala Cys Ile Glu Ser Ile
            485                 490                 495

Arg Asn Gly Thr Tyr Asp His Asp Val Tyr Arg Asp Glu Ala Leu Asn
            500                 505                 510

Asn Arg Phe Gln Ile Lys Gly Val Glu Leu Lys Ser Gly Tyr Lys Asp
            515                 520                 525

Trp Ile Leu Trp Ile Ser Phe Ala Ile Ser Cys Phe Leu Leu Cys Val
            530                 535                 540

Val Leu Leu Gly Phe Ile Met Trp Ala Cys Gln Arg Gly Asn Ile Arg
545                 550                 555                 560

Cys Asn Ile Cys Ile
            565

<210> SEQ ID NO 43
<211> LENGTH: 283
<212> TYPE: PRT
<213> ORGANISM: Artificial Sequence
<220> FEATURE:
<223> OTHER INFORMATION: Synthetic Construct

<400> SEQUENCE: 43

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Gly Gly Gly Lys Tyr Val Arg Ser Ala Lys Leu
50                  55                  60

Arg Met Val Thr Gly Leu Arg Asn Ile Pro Ser Ile Gln Ser Arg Gly
65                  70                  75                  80

Leu Phe Gly Ala Ile Ala Gly Phe Ile Glu Gly Gly Trp Thr Gly Met
            85                  90                  95

-continued

Ile Asp Gly Trp Tyr Gly Tyr His His Gln Asn Glu Gln Gly Ser Gly
                100                 105                 110

Tyr Ala Ala Asp Gln Lys Ser Thr Gln Asn Ala Ile Asn Gly Ile Thr
            115                 120                 125

Asn Lys Val Asn Thr Val Ile Glu Lys Met Asn Ile Gln Gly Ser Gly
        130                 135                 140

Gly Ser Gly Tyr Asn Ala Glu Leu Leu Val Leu Leu Glu Asn Glu Arg
145                 150                 155                 160

Thr Leu Asp Phe His Asp Ser Asn Val Lys Asn Leu Tyr Glu Lys Val
                165                 170                 175

Lys Ser Gln Leu Lys Asn Asn Ala Lys Glu Ile Gly Asn Gly Cys Phe
            180                 185                 190

Glu Phe Tyr His Lys Cys Asp Asn Glu Cys Met Glu Ser Val Arg Asn
        195                 200                 205

Gly Thr Tyr Asp Tyr Pro Lys Tyr Ser Glu Glu Ser Lys Leu Asn Arg
210                 215                 220

Glu Lys Val Asp Gly Val Lys Leu Glu Ser Met Gly Ile Tyr Val Asp
225                 230                 235                 240

Pro Gly Ser Met Lys Gln Ile Glu Asp Lys Ile Glu Glu Ile Leu Ser
                245                 250                 255

Lys Ile Tyr His Ile Glu Asn Glu Ile Ala Arg Ile Lys Lys Leu Ile
            260                 265                 270

Ala Ala Ala Leu Glu His His His His His His
        275                 280

<210> SEQ ID NO 44
<211> LENGTH: 562
<212> TYPE: PRT
<213> ORGANISM: Influenza A Virus

<400> SEQUENCE: 44

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Lys Leu Cys Arg Leu Lys Gly Ile Ala Pro Leu
    50                  55                  60

Gln Leu Gly Lys Cys Asn Ile Ala Gly Trp Leu Leu Gly Asn Pro Glu
65                  70                  75                  80

Cys Asp Pro Leu Leu Pro Val Arg Ser Trp Ser Tyr Ile Val Glu Thr
                85                  90                  95

Pro Asn Ser Glu Asn Gly Ile Cys Tyr Pro Gly Asp Phe Ile Asp Tyr
            100                 105                 110

Glu Glu Leu Arg Glu Gln Leu Ser Ser Val Ser Ser Phe Glu Arg Phe
        115                 120                 125

Glu Ile Phe Pro Lys Glu Ser Ser Trp Pro Asn His Asn Thr Asn Gly
    130                 135                 140

Val Thr Ala Ala Cys Ser His Glu Gly Lys Ser Ser Phe Tyr Arg Asn
145                 150                 155                 160

Leu Leu Trp Leu Thr Glu Lys Glu Gly Ser Tyr Pro Lys Leu Lys Asn
                165                 170                 175

Ser Tyr Val Asn Lys Lys Gly Lys Glu Val Leu Val Leu Trp Gly Ile

```
                    180                 185                 190
His His Pro Pro Asn Ser Lys Glu Gln Gln Asn Leu Tyr Gln Asn Glu
            195                 200                 205

Asn Ala Tyr Val Ser Val Val Thr Ser Asn Tyr Asn Arg Arg Phe Thr
        210                 215                 220

Pro Glu Ile Ala Glu Arg Pro Lys Val Arg Asp Gln Ala Gly Arg Met
225                 230                 235                 240

Asn Tyr Tyr Trp Thr Leu Leu Lys Pro Gly Asp Thr Ile Ile Phe Glu
                245                 250                 255

Ala Asn Gly Asn Leu Ile Ala Pro Met Tyr Ala Phe Ala Leu Ser Arg
            260                 265                 270

Gly Phe Gly Ser Gly Ile Ile Thr Ser Asn Ala Ser Met His Glu Cys
        275                 280                 285

Asn Thr Lys Cys Gln Thr Pro Leu Gly Ala Ile Asn Ser Ser Leu Pro
        290                 295                 300

Tyr Gln Asn Ile His Pro Val Thr Ile Gly Glu Cys Pro Lys Tyr Val
305                 310                 315                 320

Arg Ser Ala Lys Leu Arg Met Val Thr Gly Leu Arg Asn Ile Pro Ser
                325                 330                 335

Ile Gln Ser Arg Gly Leu Phe Gly Ala Ile Ala Gly Phe Ile Glu Gly
            340                 345                 350

Gly Trp Thr Gly Met Ile Asp Gly Trp Tyr Gly Tyr His His Gln Asn
            355                 360                 365

Glu Gln Gly Ser Gly Tyr Ala Ala Asp Gln Lys Ser Thr Gln Asn Ala
        370                 375                 380

Ile Asn Gly Ile Thr Asn Lys Val Asn Thr Val Ile Glu Lys Met Asn
385                 390                 395                 400

Ile Gln Phe Thr Ala Val Gly Lys Glu Phe Asn Lys Leu Glu Lys Arg
                405                 410                 415

Met Glu Asn Leu Asn Lys Lys Val Asp Asp Gly Phe Leu Asp Ile Trp
            420                 425                 430

Thr Tyr Asn Ala Glu Leu Leu Val Leu Leu Glu Asn Glu Arg Thr Leu
            435                 440                 445

Asp Phe His Asp Ser Asn Val Lys Asn Leu Tyr Glu Lys Val Lys Ser
        450                 455                 460

Gln Leu Lys Asn Asn Ala Lys Glu Ile Gly Asn Gly Cys Phe Glu Phe
465                 470                 475                 480

Tyr His Lys Cys Asp Asn Glu Cys Met Glu Ser Val Arg Asn Gly Thr
                485                 490                 495

Tyr Asp Tyr Pro Lys Tyr Ser Glu Glu Ser Lys Leu Asn Arg Glu Lys
            500                 505                 510

Val Asp Gly Val Lys Leu Glu Ser Met Gly Ile Tyr Gln Ile Leu Ala
            515                 520                 525

Ile Tyr Ser Thr Val Ala Ser Ser Leu Val Leu Leu Val Ser Leu Gly
        530                 535                 540

Ala Ile Ser Phe Trp Met Cys Ser Asn Gly Ser Leu Gln Cys Arg Ile
545                 550                 555                 560

Cys Ile
```